(12) United States Patent
Peters et al.

(10) Patent No.: US 8,882,905 B1
(45) Date of Patent: *Nov. 11, 2014

(54) RECYCLED COMPOSITIONS FOR CONSTRUCTION, AND METHODS OF UTILIZING AND PRODUCING THE SAME

(75) Inventors: Stanley R. Peters, Castle Rock, CO (US); Henry J. Karam, Floresville, TX (US); John M. Suter, Littleton, CO (US)

(73) Assignee: Flashfill Services, LLC, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/149,542

(22) Filed: May 31, 2011

Related U.S. Application Data

(63) Continuation-in-part of application No. 13/112,793, filed on May 20, 2011, now Pat. No. 8,747,547.

(60) Provisional application No. 61/395,956, filed on May 20, 2010, provisional application No. 61/395,930, filed on May 20, 2010, provisional application No. 61/455,604, filed on Oct. 25, 2010, provisional application No. 61/396,482, filed on May 28, 2010, provisional application No. 61/458,630, filed on Nov. 29, 2010, provisional application No. 61/458,861, filed on Dec. 3, 2010, provisional application No. 61/464,547, filed on Mar. 7, 2011, provisional application No. 61/462,978, filed on Feb. 11, 2011, provisional application No. 61/464,546, filed on Mar. 7, 2011.

(51) Int. Cl.
*C04B 18/06* (2006.01)
*C04B 18/08* (2006.01)

(52) U.S. Cl.
USPC ............................. 106/705; 106/DIG. 1

(58) Field of Classification Search
USPC ............................ 106/705, DIG. 1
See application file for complete search history.

(56) References Cited

U.S. PATENT DOCUMENTS

| | | |
|---|---|---|
| 3,625,723 A | 12/1971 | Sicka |
| 4,624,711 A | 11/1986 | Styron |
| 4,659,385 A * | 4/1987 | Costopoulos et al. ........ 588/257 |
| 4,741,782 A | 5/1988 | Styron |
| 4,900,359 A | 2/1990 | Gelbman |
| 5,106,422 A | 4/1992 | Bennett et al. |
| 5,183,505 A | 2/1993 | Spinney |
| 5,419,632 A | 5/1995 | Stephens |
| 5,494,514 A | 2/1996 | Goodson et al. |

(Continued)

OTHER PUBLICATIONS

Hennis et al., "A New Era in Control Density Fill", No Date, pp. 53-1 to 53-12, American Electric Power, Columbus, OH, USA.

(Continued)

*Primary Examiner* — Paul Marcantoni

(57) ABSTRACT

A low density annular grout composition for filling voids. The composition may consist of cementitious fly ash, water, set retarder and cellular foam. The composition may have a compressive strength of between 100 and 600 psi at seven days and less than 1500 psi at 28 days. The composition may have a density between 20 and 75 pcf. Also disclosed is a method of filling a void with a low density annular grout composition. The method can include determining the time necessary to fill the void, adding water and set retarder to a cementitious fly ash to make a wet mixture, adding air to the wet mixture, and adding the composition to the void.

19 Claims, 16 Drawing Sheets

(56) References Cited

U.S. PATENT DOCUMENTS

| | | | |
|---|---|---|---|
| 5,921,707 | A | 7/1999 | Owen |
| 6,485,561 | B1 | 11/2002 | Dattel |
| 7,413,014 | B2 | 8/2008 | Chatterji et al. |
| 7,468,154 | B2 | 12/2008 | Dubey |

OTHER PUBLICATIONS

American Electric Power, "Flash Fill", No Date, 5 pgs., American Electric Power, Columbus, OH, USA.

Lautzenheiser, Robert, Letter Dated Sep. 12, 1996 Regarding Flash Fill Product, 1 pg.

Sheets, Dana M., Letter Dated Sep. 10, 1996 Regarding Leachate Test Results, 2 pgs.

Behlen, Thomas P., Letter Dated Apr. 6, 1992 Regarding Flash Fill Technical Review, 3 pgs.

Turner, Andrew, Letter Dated Feb. 8, 1991, 1 pg.

Sheets, Dana M., Letter Dated Jan. 24, 1991 Regarding Flowable Fly Ash Backfill Material, 2 pgs.

Letter Dated Sep. 17, 1990 Regarding Use of Fly Ash as a Backfill Material, 1 pg.

Peters, Stan, "Flowable Fill Using Spray Dryer Ash", Ash at Work, 2011, pp. 40-41, Issue 1.

Allen, Marilyn H., "Pacific International Grout Co.", AUA News Magazine, 2000, 4 pgs., Transcontinental Publishing, Inc., Phoenix, AZ, USA.

Stephens, Pat, "Pacific Grout Rescues TBM and Backfills Tunnels", Trenchless Technology, Oct. 1996, 2 pgs.

Glysson et al., "Guide for Cast-in-Place Low-Density Cellular Concrete", Reported by ACI Committee 523, ACI Committee Report, No Date, pp. 523.1R-1 to 523.1R-13, ACI 523.1R-06.

Duran, Darin R., Letter Report Dated Aug. 18, 2010 Regarding Flashfill Frost Heave Study, Project No. D10.035, 25 pgs.

Cross et al., "Sustainable Construction Contributions from the Treasure State", Concrete International, May 2010, pp. 41-46, vol. 32, No. 5.

American Coal Ash Association, "Fly Ash Facts for Highway Engineers", Technical Report, Jun. 13, 2003, 81 pgs.

Cellular Concrete LLC, "Synthetic Concrete Foam", Material Safety Data Sheet, Jul. 24, 2008, pp. 1-5.

Ramme et al., "Controlled Low-Strength Materials", Reported by ACI Committee 229, Manual of Concrete Practice, 2005, pp. 229R-1 to 229R-15, American Concrete Institute, Farmington Hills, MI, USA.

Cross et al., "Evaluation of the Durability of 100 Percent Fly Ash Concrete", Jun. 2008, 46 pgs., Project No. 05-CBRC-W08, Western Transportation Institute, Bozeman, MT, USA.

Cross et al., "Field Trials of 100% Fly Ash Concrete", Concrete International, Sep. 2005, 3 pgs., obtained online at: http://findarticles.com/p/articles/mi_qa5363/is_200509/ai_n21386494/.

Cross et al., "A Green Gem in the Treasure State", Ash at Work, 2009, pp. 13-19, Issue 1.

Folliard et al., "Development of a Recommended Practice for Use of Controlled Low-Strength Material in Highway Construction", NCHRP Report 597, 2008, p. 29, Transportation Research Board, Washington, D.C., USA.

Cross et al., "Structural Applications of 100 Percent Fly Ash Concrete", No Date, pp. 1-19.

\* cited by examiner

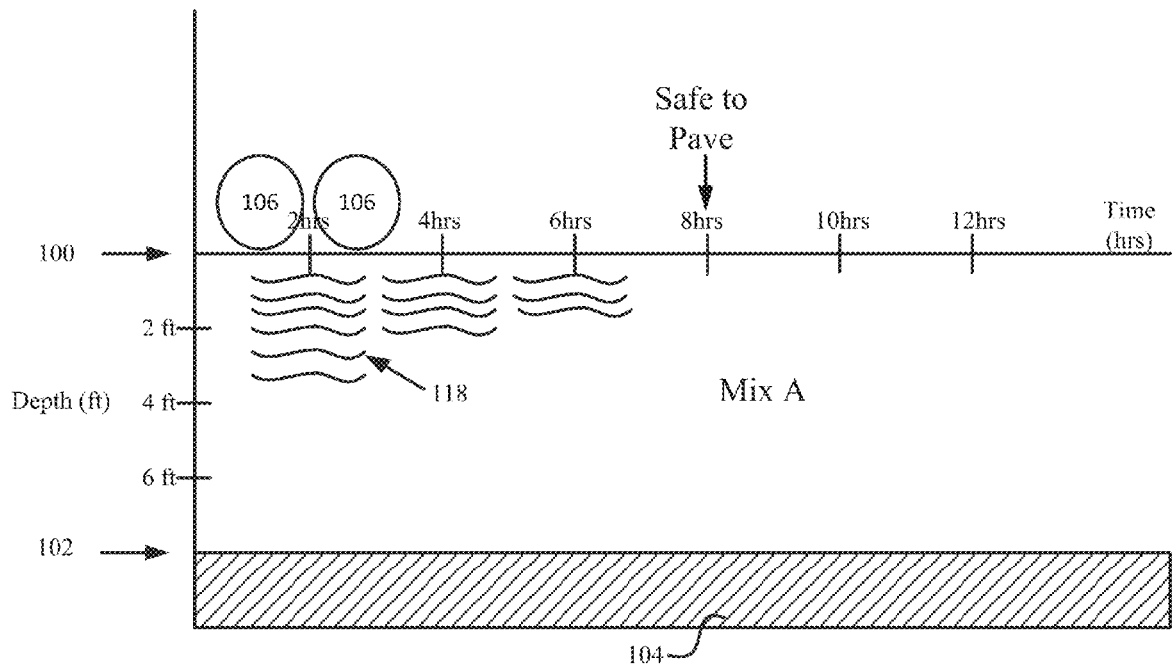
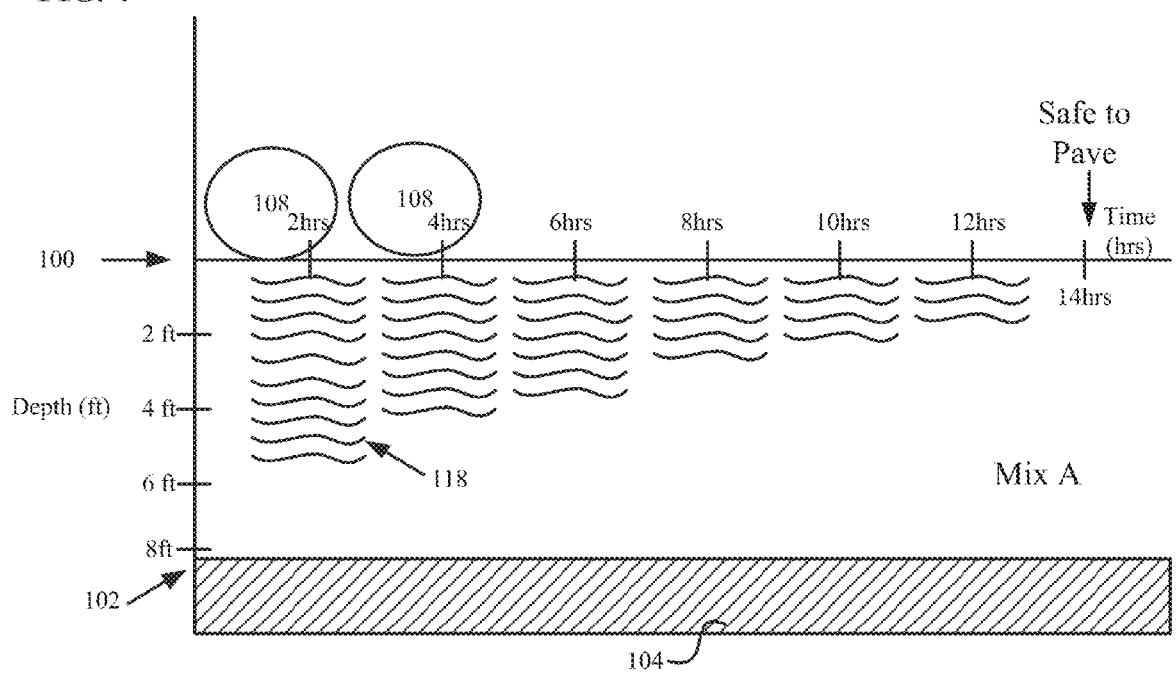

FIG. 11

Gentleman C Ash: 0.28 at 10 Inch Spread

Valmont C Ash: 0.49 at 10 Inch Spread

| Ratio | Gentleman | Valmont | Estimated Water/Fly Ash | Estimated Strength |
|---|---|---|---|---|
| 1:0 | 100% | 0% | 0.28 | 320 PSI |
| 2:1 | 67% | 33% | 0.35 | 200 PSI |
| 1:1 | 50% | 50% | 0.39 | 120 PSI |
| 1:2 | 33% | 67% | 0.42 | 60 PSI |
| 1:3 | 25% | 75% | 0.44 | 20 PSI |

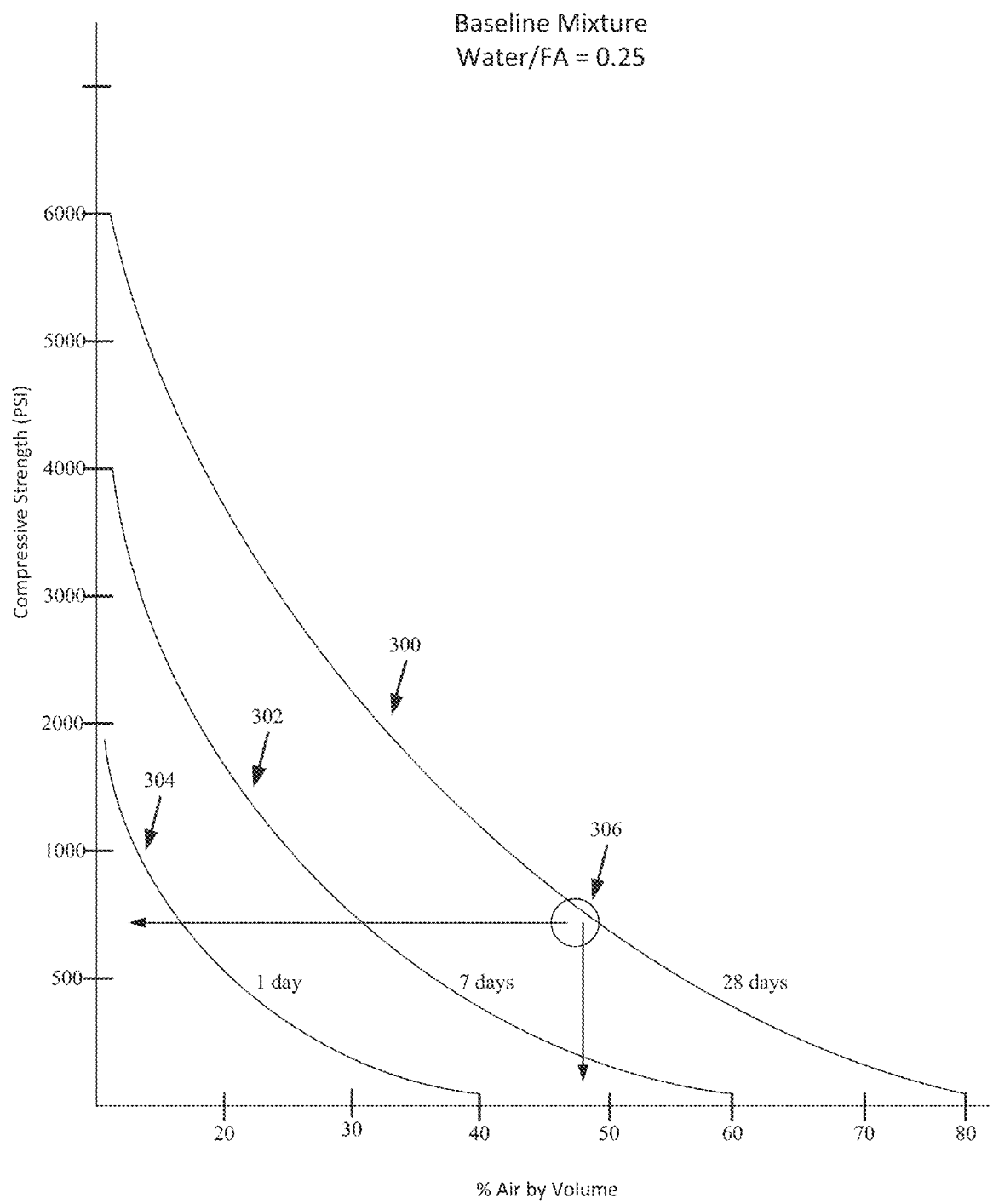

RECYCLED COMPOSITIONS FOR CONSTRUCTION, AND METHODS OF UTILIZING AND PRODUCING THE SAME

RELATED APPLICATIONS

This application claims priority to and is a continuation-in-part of U.S. patent application Ser. No. 13/112,793, filed on May 20, 2011. This application claims priority to U.S. Provisional Patent Application Ser. No. 61/396,482, filed May 28, 2010, U.S. Provisional Patent Application Ser. No. 61/458,630, filed on Nov. 29, 2010, U.S. Provisional Patent Application Ser. No. 61/458,861, filed on Dec. 3, 2010, U.S. Provisional Patent Application Ser. No. 61/464,547, filed on Mar. 7, 2011, U.S. Provisional Patent Application Ser. No. 61/462,978, filed on Feb. 11, 2011, and U.S. Provisional Patent Application Ser. No. 61/464,546, filed on Mar. 7, 2011.

INTRODUCTION

The present disclosure generally relates to using fly ash as a cementitious ingredient in compositions. Using fly ash, a by-product of coal-fired electric power production as a substitute for Portland cement has many social benefits for sustainability as fly ash is a 100% recycled, post-consumer product. Further, no additional carbon dioxide is produced, no additional natural resources are mined and no additional fossil fuels are used. By contrast, the use of Portland cement requires approximately 3500 lbs of mined resources and fossil fuels to produce each ton of cement. In addition, the avoidance of carbon dioxide generation by using fly ash creates carbon credits, which adds economic value to any given project.

The present disclosure provides compositions and methods for filling surface and subsurface voids with cellular, annular grout comprising cementitious fly ash. Annular grout is historically a Portland cement composition for use in filling subterranean voids, i.e., areas around an underground pipe. Typically, access to the void is restricted, such that, the composition for filling the void must be pumped into the void without direct access to the entire void. For example, annular grout is typically used when replacing an older underground pipe with a new pipe by slip-lining the old pipe with a new pipe.

Compositions for use as an annular grout must have sufficient fluidity for pumping and subsequently filling voids without requiring any compaction. Compositions for use as annular grout must also have a delayed set time to allow the grout to flow the length or width of the void without setting. Compositions of the present disclosure exhibit sufficient fluidity for pumping, set-times for extended durations of installation, yet sufficiently high strengths at the required low densities.

In another embodiment, compositions of the present disclosure alleviate the frost-heave typically associated with backfill composition and reduces ice lens formation. Generally, to manipulate underground utilities or for equivalent reasons, an operator must excavate the area on top of and surrounding the work site to gain access to the underground area of interest. Following manipulation of the area of interest, e.g., water pipe or sink hole, the excavated area will be backfilled with a composition that promotes subsequent use of the surface as quickly as possible. For example, when the area of interest lies beneath a road surface crucial for a city's traffic pattern, the time from excavation to reopening of the road is critical. The downtime following repair is directly correlated to when the backfilled surface will support the anticipated use, i.e., vertical loads from routine traffic or compression from pavement structures which withstand substantial loads.

In addition to the downtime associated with said repair, one must also consider the longevity and integrity of the backfilled area. Often, even when downtime is minimized using specific compositions, the same compositions are subject to facture cracking during compaction of the asphalt allowing subsequent ice lens formation during freeze thaw cycles. The ice lens formation within the backfill drives the backfill—and surface pavement covering said backfill—up as the ice lenses freeze and expand. This results in an uneven surface and the need for further repair to the backfilled site. The resulting uneven surface also damages the shovels of city snowplows and causes general damage to vehicles subjected to the uneven road surface.

U.S. Pat. No. 5,106,422 (the "'422 patent") discloses a backfill composition including a minor amount of cementitious Class C fly ash and other filler materials in a major amount. When such materials are combined with water, they produce a backfilling material. The backfilling composition of the '422 patent ranges in amount from about 2 to 10 parts by weight filler material to about 1 part by weight Class C fly ash with sufficient water to react with both Class C fly ash and filler material. Problems have been encountered with the formulations of the '422 patent, and new compositions are necessary to solve these problems.

For example, freeze-thaw vertical heave of pavement patches is a common issue with current '442 patent backfill compositions. Several investigations in regions having freeze-thaw temperature zones have discovered the freeze-thaw vertical heave of pavement patches is due to the formation of ice lenses in the horizontal cracks of current backfill compositions. The creation of these horizontal cracks results from the compacting of asphalt patches overlying the backfilled void and/or post placement excavating and patch installation. The compacting of asphalt patches is necessary to achieve the correct density.

Most agencies require the type of pavement repair material be the same type and thickness as the original pavement, to achieve compatibility with the trench repair. In some cases, agencies also require a T-patch where the surface area of the patch is larger than the trench backfill surface area. Some installers and municipalities have stopped using compositions of the '422 patent because of frost heave problems. Most roadways are constructed of asphalt paving materials; hence most trenches are repaired with asphalt paving materials. To achieve long-term durability of the trench patch, the asphalt must be similarly compacted to normal specifications (often to 92% to 96% of the theoretical maximum density). To achieve these densities, most contractors utilize their steel-wheeled compactors in vibratory mode, not static-mode.

However, typically, the strength of the backfill material near the surface is not sufficiently strong enough to resist the horizontal shear stresses caused by the compactive mechanism, e.g., rollers, resulting in horizontal compaction fractures.

When water infiltrates these horizontal cracks and freezes in cold weather climates, the entrapped water expands vertically by around 11% of its volume/thickness. Thawing allows more water to infiltrate the new crack volume, which then expands around 11% during the next freezing cycle. Repeated freeze-thaw cycles during a winter can create individual ice lenses up to ⅜ of an inch or more. The heave of the pavement patch at the surface is the sum of the thickness of these ice lenses formed above the local frost depth, and can be up to 3-inches above the original pavement surface or more.

The compositions and methods of the present disclosure alleviate the encountered problems. Namely, the present disclosure alleviates the frost-heave typically associated with previous backfill and reduces ice lens formation. The compositions and methods of the present disclosure also provide a more homogenous mixture, e.g., the high air content contributes to fluidity and reduces gravity segregation; thereby preventing the flotation of carbon particles to the surface and resulting in weakened planes for early freezing or compactive cracking.

The compositions and methods of the present disclosure also provide a composition with a lower modulus of elasticity that is more forgiving & less-brittle during compaction; thereby decreasing the likelihood of horizontal crack development. In addition, the present disclosure identifies methods for determining and using compositions that reach a critical compression strength quicker, maintain a lower removability modulus ("RE"), prevent water from becoming trapped within the backfilled composition, expedite backfill mixture optimization, and provide more predictable and repeatable laboratory procedures, mix designs and testing methods.

The present disclosure further provides a composition that reduces the backfill composition setting time; thereby reducing the time to pave or patch and resulting in a total reduction in time from the start of backfilling to a return to normal use.

In addition, the present disclosure also discloses a high-performance composition, generating high strengths, suitable for replacement of traditional concrete in specific applications of building construction, and methods of using the same. The present disclosure further includes compositions made of 100% recycled materials that will achieve normal structural requirements normally achieved with Portland-cement, and methods of using the same.

The present disclosure further provides a masonry grout composition for filling cores or cavities in traditional masonry construction, and methods of using the same. The present disclosure additionally provides an economical, easy-to-install composition for use as wicking layer under concrete slabs, instead of the general industry recommended layer of compacted crusher fines, and method of using the same. The present disclosure also further discloses a composition for use as a more durable temporary pavement patch than traditional "cold-mix" asphalt products currently in wide use, and methods of using the same.

SUMMARY

The present disclosure identifies a low density annular grout composition for filling surface or subsurface voids comprising between 30%-85% air by volume; between 50%-90% cementitious fly ash by weight; between 10% and 45% water by weight; and between 0.01% and 2% set retarder by weight, wherein the composition has compressive strength of between 100 and 600 psi at seven days, a compressive strength of less than 1500 psi at 28 days, and a density of between 25 and 75 pcf. In some embodiments the composition my further comprise a filler.

The present disclosure includes a method of determining a low density annular grout composition for filling a void comprising identifying at least one fly ash for use in the composition; determining a water demand of each fly ash within the composition; calculating a water demand for the composition; determining a compressive strength for the composition; determining the amount of air content necessary for the composition to have a compressive strength of between 100 and 600 psi at seven days, a compressive strength of less than 1500 psi at 28 days, and a density of between 20 and 75 pcf; determining the time necessary to fill the void; and determining the concentration of set retarder necessary to delay the composition from setting before the void is completely filled.

The present disclosure includes a method of filling a void with a low density annular grout composition comprising determining the time necessary to fill the void; adding water and set retarder to a cementitious fly ash to make a wet mixture; adding air to the wet mixture, wherein the composition has a compressive strength of between 100 and 600 psi at seven days, a compressive strength of less than 1500 psi at 28 days, and a density of between 20 and 75 pcf; and adding the composition to the void.

The present disclosure also reveals a high-performance backfill composition, generating higher early strengths yet still sufficiently low ultimate strengths, at the same time improving freeze-thaw durability and reducing the occurrence of frost-heaved trench patches. In an embodiment, the present disclosure achieves these goals by purposely including air content for a new and improved cementitious fly ash composition for backfilling voids. In an embodiment, the amount of air content created by varying cellular foam additions can be optimized for the ultimate strength gain desired, the performance of specific fly ashes used, and the ambient temperature during the backfilling process.

In an embodiment, compositions and methods of the present disclosure generally solve problems with frost-heave in backfilled voids resulting, mostly, from ice lens formation. Compositions and methods of the present disclosure prevent problematic compaction fractures, which allow frost-heave, by determining the strength needed to resist compaction fractures to depths of local frost penetration. Once this strength level is determined for specific equipment & procedures, various compositions can be utilized to achieve this strength level in time frames desired to patch and open the roadway to traffic. Different strength levels can be used below the depth of frost-penetration and/or influence of compaction equipment, thus optimizing the overall economics of trench backfill, subject to the desired time constraints.

Interestingly, testing shows that time to set is a function of the free lime concentration in a blend of cementitious and non-cementitious fly ashes or other fillers, and the water/fly ash ratio, but essentially independent of the amount of air content, e.g., from cellular foam. Hence a faster set time can be achieved with more blends using more cementitious fly ash and lower water/fly ash ratios, while the ultimate strength can be limited with higher amounts of air content.

In an embodiment, a composition of the present disclosure includes a composition for preventing ice lens formation comprising from 5% to 70% air; from 5% to 90% cementitious fly ash; and from 5% to 70% water, wherein the composition has a compressive strength of between 10 and 60 PSI after 4 hours and a removability modulus of less than 1.8 after 28 days. Additional compositions can include a filler from 5% to 80%. Unless otherwise stated, all percentages of compositions are weight percent based on the final weight of the composition including the weight of water and air. The exception is that all percentages of air are based on volume of the final composition as defined in the Detailed Description.

In an embodiment, a method of the present disclosure includes a method of determining a composition to prevent ice lens formation comprising determining the water demand of each fly ash within the composition to achieve a desired fluidity; calculating the water demand for a combination of fly ashes; determining the compressive strength for the combination of fly ashes; and determining the amount of air content necessary for the composition to have a compressive strength of between 10 and 60 PSI after 4 hours and a removability modulus of less than 1.8 after 28 days.

An alternative method of the present disclosure comprises a method of backfilling a void to prevent ice lens formation comprising mixing cementitious fly ash and filler to a predetermined ratio; adding water to the mix of cementitious fly ash and filler to make a wet mixture; adding air to the wet mixture, wherein the predetermined mix of cementitious fly ash and filler, the addition of water and the addition of air makes a composition having a compressive strength of between 10 and 60 PSI within 4 hours and a removability modulus of less than 1.8 after 28 days; and adding the composition to a void.

The present disclosure also further comprises in an embodiment, a composition for caisson construction comprising between 0.0001% and 10% air by volume: between 60%-95% cementitious fly ash by weight; between 5%-30% water by weight; and between 0.01% and 2% set retarder by weight, wherein the composition has compressive strength of between 3000 and 5000 psi at seven days, a compressive strength of between 4000 and 8000 psi at 28 days, and a density of between 100 and 150 pcf. Additional methods of utilizing and designing compositions for caisson construction are also disclosed.

In an embodiment, the present disclosure further comprises a composition for construction comprising between 0.0001% and 10% air by volume; between 60%-95% cementitious fly ash by weight: between 5%-30% water by weight; and between 0.01% and 2% set retarder by weight, wherein the composition has compressive strength of between 3500 psi and 6000 psi at seven days, between 5000 psi and 10,000 psi at 28 days, and a density of between 100 and 150 pcf. Methods of utilizing and designing compositions for construction are also disclosed.

In an additional embodiment, the present disclosure further discloses a recycled composition comprising between 0.0001% and 10% air by volume; between 15%-35% cementitious fly ash by weight: between 5%-15% water by weight; between 50%-80% recycled filler and between 0.01% and 2% set retarder by weight, wherein the composition sets in less than 4 hours and has a density of between 115 and 150 pcf. Methods of utilizing and designing recycled compositions are also disclosed.

In an embodiment, the present disclosure further discloses a masonry grout composition comprising between 0.0001% and 15% air by volume; between 70%-95% cementitious fly ash by weight; between 10%-30% water by weight, wherein the composition sets in less than 40 minutes and has a compressive strength of between 100 and 500 psi after 1 hour and 2500 and 6000 psi after 24 hours. Methods of utilizing and designing masonry grout compositions are also disclosed.

The present disclosure further provides a wicking composition comprising between 45% and 80% air by volume; between 70%-90% cementitious fly ash by weight; and between 10%-30% water by weight, wherein the composition sets in less than 4 hours, has a compressive strength of between 100 and 600 psi after 7 days and has a density of between 20 and 60 pcf. Methods of utilizing and designing wicking compositions are also disclosed.

In an embodiment, the present disclosure further discloses a composition for patching a trench comprising between 70%-95% cementitious fly ash by weight; between 10% and 30% water by weight; and between 0.01% and 2% set retarder by weight, wherein the composition has compressive strength of between 150 and 450 psi in 1 hour, a compressive strength of between 600 and 1800 psi in 4 hours, and a set time of less than 40 minutes. Methods of utilizing and designing compositions for trench patching are also disclosed.

While the disclosure will be described with respect to preferred embodiment configurations and with respect to particular compositions or methods used therein, it will be understood that the disclosure is not to be construed as limited in any manner by either such configuration or components described herein. Also, while the particular types of equipment, compositions and uses are described herein, it will be understood that such particular compositions, equipment or uses are not to be construed in a limiting manner. Instead, the functionality of those compositions and methods should be appreciated. These and other variations of the disclosure will become apparent to those skilled in the art upon a more detailed description of the disclosure.

The advantages and features which characterize the disclosure are pointed out with particularity in the claims annexed hereto and forming a part hereof. For a better understanding of the disclosure, however, reference should be had to the drawing which forms a part hereof and to the accompanying descriptive matter, in which there is illustrated and described an embodiment of the disclosure.

BRIEF DESCRIPTION OF THE DRAWINGS

Referring to the drawing, wherein like numerals represent like parts throughout the several views.

FIG. 3 illustrates the creation of horizontal cracks by the same small compactor as FIG. 1 but with a new backfill composition (Mix A) that develops strength faster than the backfill composition used in FIG. 1 (Mix B).

FIG. 4 illustrates the creation of horizontal cracks by the same large compactor as FIG. 2 but with a new backfill composition (Mix A) that develops strength faster than the backfill composition used in FIG. 2 (Mix B).

FIG. 11 illustrates how using the previously tested water demand for several fly ashes, including cementitious and non-cementitious fly ashes, can help develop the correct ratios and water content for a desired strength.

FIG. 19 illustrates a strength versus air content graph for an annular grout composition of an embodiment in the present disclosure.

DETAILED DESCRIPTION

Figure 1:
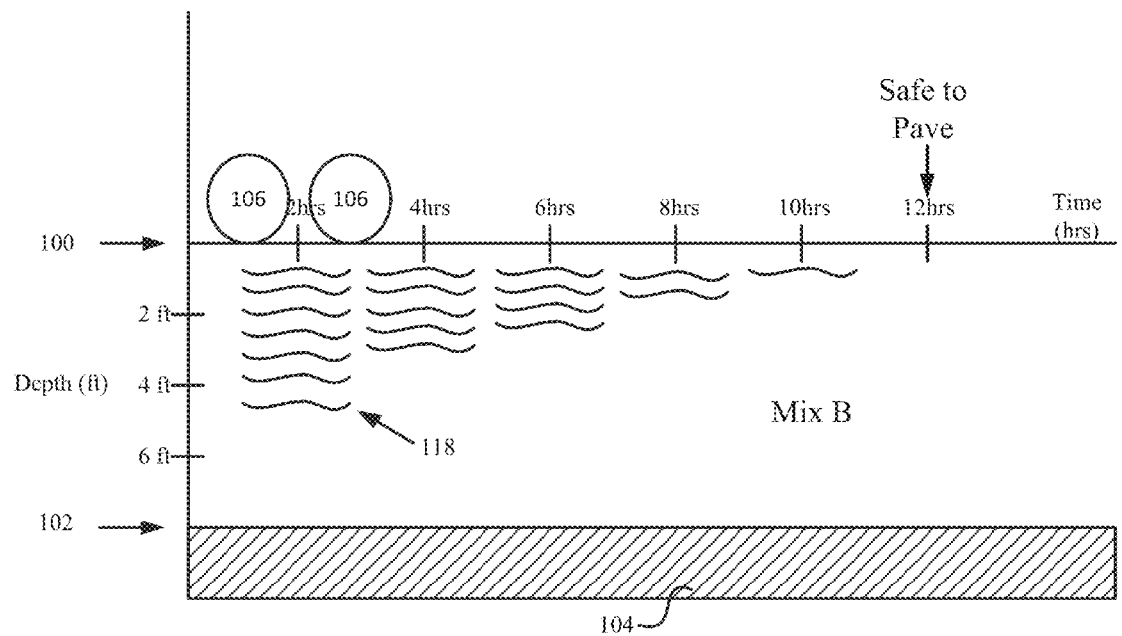
FIG. 1 illustrates the creation of horizontal cracks by a small compactor on a backfilled trench as a function of time.

Foamed Backfill Compositions and Methods of Utilizing the Same

The present disclosure provides compositions and methods for reducing freeze-thaw heave risk over flowable-filled voids; and, more particularly, to a composition for reducing horizontal cracks and the subsequent formation of ice lenses, and methods of producing and utilizing the same.

Generally, one must consider several factors when determining an appropriate composition for backfilling a trench or void in the middle of a public roadway or street. These factors include the flowability or spread of the backfill, the setting time of the backfill, the air content of the backfill, the final compressive strength of the backfill and the removability of the backfill.

For example, strength development in backfilling compositions is directly related to the amount of cementitious material and water content. In an embodiment of this disclosure, the primary cementitious material is cementitious fly ash. Water content of the composition also influences strength development as the addition of water controls flowability or slump. While it is desirable to support the intended use, e.g., traffic loading, the final strength of the composition must still allow later excavation. In certain embodiments, a composition should be less than 300 psi for ease of later excavation.

In addition, considering the flowability of the compositions will assume the advantage of the self-compacting and self-leveling qualities of composition. In some embodiments of the present disclosure, the flowability may be determined using ASTM D6103, e.g., utilizing a moistened 3 inch diameter by 6 inch high open-ended cylinder filled with a composition. Along with strength development and flowability, setting time is an additional factor to consider when determining a suitable composition. The faster the composition sets and gains strength after filling the void, the sooner the backfilled surface may be paved or patched and returned to normal use.

The present disclosure reveals a high-performance backfill composition, generating higher early strengths yet still sufficiently low ultimate strengths, at the same time improving freeze-thaw durability and reducing the occurrence frost-heaved trench patches. In an embodiment, the present disclosure achieves these goals using increased air content for a new and improved cementitious fly ash composition for backfilling voids. In an embodiment, the amount of air content created by varying foam additions can be optimized for the strength gain desired, the performance of specific fly ashes used, and the ambient temperature during the backfilling process.

An embodiment of the present invention includes a composition for preventing ice lens formation comprising between 5% and 60% air; between 5% and 90% cementitious fly ash; and between 5% and 70% water, wherein the composition has a time to set of less than 40 minutes, a compressive strength of between 10 and 60 PSI after 4 hours and a removability modulus of less than 1.8 after 28 days. In additional embodiments, a composition of the present disclosure may contain a filler.

The air content of the compositions of the present disclosure will vary depending on the desired properties of the composition. For example, the amount of air within the composition helps control the final strength of the backfill. Therefore, a faster set time can be achieved with blends using more cementitious fly ash and lower water/fly ash ratios, while the ultimate strength can be limited with higher amounts of air content.

In some embodiments, the air content may be determined by the following formula using wet densities before and after the addition of air:

$$\text{Air content} = \frac{(\text{Unit Weights}_{no\ air} - \text{Unit Weight}_{air}) \times 100\%}{\text{Unit Weight}_{no\ air}}$$

In other embodiments, the air content can be determined using ASTM C231.

In certain embodiments, the air content is achieved by mixing an air entraining agent, i.e., a dry surfactant or liquid admixture into the cementitious fly ash and/or filler prior to addition of water. In these embodiments, the air content may by uniformly distributed by mixing directly in a truck or by mixing in a commonly used agitation/mixing device. The mixing process can occur with prior to addition of water, after addition of water or simultaneously with the addition of water.

In another embodiment, the air content is achieved by addition of an air entraining agent after mixture of the dry ingredients (cementitious fly ash and possible filler) with water but prior to applying the composition to the void.

In specific embodiments, the air content may be achieved by adding a pre-formed cellular foam, e.g., GEOFOAM SNP foam liquid concentrate available from Cellular Concrete. LLC., 7020 Snowdrift Road, Suite 102, Allentown, Pa. 18106 or 5916 McIntyre St, Golden, Colo. 80403. The cellular foam may be pervious or non-pervious, and pre-foamed thereby reducing or alleviating the need to vigorously agitate the composition to activate the air entraining agent. Any suitable foaming agent may be used that achieves the desired end properties as described herein, e.g., an anionic foaming agent, a cationic foaming agent or a non-ionic foaming agent. An example of a pervious foam is GEOFOAM SP. An example of a non-pervious foam is GEOFOAM SNP. When water penetration is not desired, a non-pervious cellular foam is preferred. Suitable cellular foam is available from a variety of sources, e.g., Cellular Concrete, LLC; Provoton Foam Concrete, 28 East Larkspur Lane, Bristol, Ill. 60512; Allied Foam Tech Corp., 146 Keystone Dr. Montgomeryville, Pa. 18936; and Vermillion LLC and Associates, 2176 Sargent Daly Dr., Chattanooga, Tenn. 37421. The choice of an appropriate cellular foam is within one of skill in the art and may be dictated by cost, environmental concerns, or the need to meet the requirements of local or national agencies. In some embodiments, the foaming agent will conform to ASTM C869 and C796, in other embodiments the air entraining agent conforms to ASTM C260.

In some embodiments, the addition of cellular foam or similar air entraining agent may occur after the addition of water to the cementitious fly ash and/or filler immediately prior to the cementitious mixture leaving a mixing truck, as the cementitious mixture leaves the mixing truck (simultaneously) or after the cementitious mixture leaves the mixing truck.

The amount of air entraining agent necessary for a given composition will vary with the desired air content, e.g., the desired final compressive strength. In some embodiments, the final air content of the composition will be between about 10% and about 75%, between about 11% and about 65%, between about 12% and about 60%, between about 13% and about 55%, between about 14% and about 50%, between about 15% and about 45%, between about 16% and about 40%, between about 17% and about 35%, between about 18% and about 30%, between about 19% and 25%, between about 15% and about 25%, between about 15% and about 30%, or between about 50% and about 70%.

In alternative embodiments, the final air content of the composition will be between about 10% and about 30%, between about 11% and about 26%, between about 12% and about 22%, between about 13% and about 20%, between about 20% and about 30% or between about 14% and 19%.

In some embodiments, the final air content will be greater than 10%, greater than 12%, greater than 14%, greater than 16%, greater than 18%, greater than 20%, greater than 22%, greater than 24%, greater than 26%, greater than 28%, greater than 30%, greater than 35%, greater than 40%, greater than 50%, or greater than about 60% final air content.

In other embodiments, the final air content of the composition will be less than 40%, less than 35%, less than 30%, less than 28%, less than 26%, less than 24%, less, than 22%, less than 20%, less than 18%, less than 16%, or less than 14%.

Fly ash can be referred to as either cementitious or pozzolanic. A cementitious material is one that hardens when mixed with water. A pozzolanic material will also harden with water but only after activation with an alkaline substance such as lime.

Two major classes of fly ash are specified in ASTM C618 on the basis of their chemical composition resulting from the type of coal burned; these are designated Class F and Class C. Class F is fly ash normally produced from burning anthracite or bituminous coal, and Class C is normally produced from the burning of subbituminous coal or lignite. Class C fly ash usually has cementitious properties in addition to pozzolanic properties due to free lime, whereas Class F is rarely cementitious when mixed with water alone.

Some relevant characteristics of fly ash are loss on ignition (LOI), fineness, chemical composition and uniformity. LOI is a measurement of unburned carbon (coal) remaining in the ash. High carbon levels, the type of carbon (i.e., activated), the interaction of soluble ions in fly ash, and the variability of carbon content are all factors affecting the performance of fly ashes.

Fineness of fly ash is most closely related to the operating condition of the coal crushers and the grindability of the coal itself. Fineness is generally defined as the percent by weight of the material retained on the 0.044 mm (No. 325) sieve. A coarser gradation can result in a less reactive ash and could contain higher carbon contents.

Chemical composition of fly ash relates directly to the mineral chemistry of the parent coal and any additional fuels or additives used in the combustion or post-combustion processes.

Uniformity of fly ash characteristics from shipment to shipment is another factor to consider when selecting fly ash or using fly ash. Some guidance documents used for fly ash quality assurance include ACI 229R (Controlled Low Strength Material), ASTM C311 (Sampling and Testing Fly Ash or Natural Pozzulans for Use as Mineral Admixture in Portland Cement Concrete), AASHTO M 295 and ASTM C618 (Fly Ash and Raw or Calcined Natural Pozzolan for Use as a Mineral Admixture in Portland Cement Concrete), ASTM C593 (Fly Ash and Other Pozzolans for Use with Lime), ASTM D5239 (Standard Practice for Characterizing Fly Ash for Use in Soil Stabilization), and ASTM E1861 (Guide for the Use of Coal Combustion by-products in Structural Fills).

In an embodiment of the present disclosure, the cementitious fly ash is Class C fly ash as defined by ASTM C618 or the standards of a local agency. In other embodiments of the present disclosure, the cementitious fly ash can have cementitious properties without qualifying as Class C fly ash under ASTM C618 or an equivalent standard. A cementitious fly ash of the present disclosure is a fly ash that sets (e.g., solidifies to 4 psi) within about thirty minutes at a water content of 30% by weight when water and cementitious fly ash are the only ingredients. The cementitious fly ash of the present disclosure can be obtained from a variety of sources based on economics, location, chemical properties, or additional criteria. For example, cementitious fly ash can be obtained from a coal-fired power plant local to the area of eventual use. In some embodiments, the cementitious fly ash is supplemented with additional calcium carbonate, free lime or equivalent to provide cementitious properties.

In an embodiment of the present disclosure, a composition has between about 5% and about 90% cementitious fly ash, between about 15% and about 70% cementitious fly ash, between about 20% and about 60% cementitious fly ash, between about 20% cementitious fly ash and about 50% cementitious fly ash, between about 35% and about 50% cementitious fly ash, and between about 40% and about 47%.

In some embodiments of the present disclosure, a composition has less than about 80% cementitious fly ash, less than about 70% cementitious fly ash, less than about 60% cementitious fly ash, less than about 50% cementitious fly ash, less than about 40% cementitious fly ash, less than about 20% cementitious fly ash, or less than about 10% cementitious fly ash. In additional embodiments of the present disclosure, the composition has greater than about 10% cementitious fly ash, greater than about 20% cementitious fly ash, cementitious fly ash, greater than about 30% cementitious fly ash, greater than about 40% cementitious fly ash, greater than about 50% cementitious fly ash, greater than about 60% cementitious fly ash, greater than about 70% cementitious fly ash, greater than about 80% cementitious fly ash, or a greater than about 90% cementitious fly ash.

In an embodiment of the presently disclosed composition, the water is standard city potable water. In another embodiment, the water used in the composition is substantially purified of additional minerals or other impurities. In still another embodiment of the present disclosure, the water is non-potable water. In additional embodiments, the water is selected based on its natural impurities, i.e., specific mineral content like calcium, magnesium, iron, or similar water minerals.

The water content of the presently disclosed composition may vary depending on desired flowability, setting time and final compressive strength. In an embodiment, of the present disclosure, a composition has a the water content of between about 5% and about 70%, between about 15% and about 60%, between about 25% and about 50%, between about 35% and about 45%, between about 10% and about 35%, between about 25% and about 35%. In additional embodiments, a composition has greater than about 10% water, greater than about 20% water, greater than about 30% water, greater than about 40% water, greater than about 50% water or greater than about 60% water. In other embodiments, a composition has less than about 55% water, less than about 45% water, less than about 35% water, less than about 24% water, less than about 20% water, less than about 15% water, or less than about 10% water. Any water included with additional ingredients, e.g, aqueous water retarders, foaming agents, etc. under the circumstances encountered in the field by the inventors has been negligible in comparison to the primary batch water and therefore has not been included in the above calculations. Depending on the actual water content of the additional ingredients used it may be necessary to consider the additional water in the final water concentrations.

In some embodiments of the present disclosure, a composition will include at least one filler. In additional embodiments, a composition will include only one filler, while in other embodiments, a composition will contain only two fillers. In still additional embodiments, a composition will contain less than 3 fillers or less than 4 fillers. A filler in the present disclosure can be additional fly ash, e.g., type F fly ash as determined by ASTM C618 or equivalent standard. A filler can also be non-specification grade non-cementitious fly ash, e.g., a fly ash that does not meet the specifications determined by ASTM C618. In certain embodiments a filler can be sand, bottom ash, quarry fines, soil, gravel and Portland cement, aggregate, or recycled version thereof. Determination of the filler material can be based on economics, availability, city, county and/or state specifications, or on the desired properties of the composition, e.g., desired setting time, flowability, or final compressive strength.

In an embodiment, a composition of the present disclosure will have between about 5% and about 80% filler, between about 15% and about 70% filler, between about 25% and about 60% filler, between about 35% and about 50% filler. In certain embodiments, a composition of the present disclosure will have less than about 80% filler, less than about 70% filler, less than about 60% filler, less than about 50% filler, less than about 40% filler, less than about 30% filler, less than about 20% filler, or less than about 10% filler. In still other embodiments, a composition of the present disclosure will have greater than about 10% filler, greater than about 20% filler, greater than about 30% filler, greater than about 40% filler, greater than about 50% filler, greater than about 60% filler, or greater than about 70% filler.

Compositions of the present disclosure will have a range of possible set times based on the desired application. For example, when backfilling trenches in roadway a quick set time is desired providing the set time allows sufficient time to complete filling of the void with the composition. Despite the desire for a quick set time, the ultimate final compressive strength must not exceed the local agency standards, i.e., maintain good removability modulus numbers. In some embodiments, the set time of the composition is determined by measuring penetration resistance with a pocket penetrometer (e.g., with a resistance of 4 psi as typically used in standard ASTM WK 27337) or cement setting time standard ASTM C403. In an embodiment of the present disclosure, the set time for a composition can be between about 8 minutes and about 40 minutes, between about 9 minutes and about 35 minutes, between about 10 minutes and about 30 minutes, between about 11 minutes and about 25 minutes, between about 12 minutes and about 20 minutes, or between about 13 minutes and about 17 minutes. In additional embodiments, a composition has a set time of less than 45 minutes, of less than about 40 minutes, of less than about 35 minutes, of less than about 30 minutes, of less than about 25 minutes, of less than about 20 minutes, of less than about 18 minutes, of less than about 16 minutes, of less than about 14 minutes. In other embodiments, a composition has a set time of greater than about 5 minutes, of greater than about 10 minutes, of greater than about 15 minutes, of greater than about 20 minutes, of greater than about 25 minutes, or of greater than about 30 minutes.

Compositions of the present disclosure will have a range of compressive strengths at various times after the addition of a composition to a void depending on the desired properties of the composition. For example, and similar to set time, a higher earlier compressive strength is advantageous when working when backfilling trenches in a roadway or other highly traveled area. The higher, earlier compressive strength allows for the backfilled void to be patched and reopened to use at an earlier time. Again, despite the desire for a high earlier compressive strength the final compressive strength must not exceed the local agency standards, i.e., maintain good removability modulus numbers.

In certain embodiments, the compressive strength is measured at 1 hour, 2 hours, 4 hours, 1 day, 3 days, 7 days and 28 days where the 28 day measurement is considered the final compressive strength. In other embodiments, the compressive strength is measured more often at smaller intervals. In some embodiments, the compressive strength is measured at 90 days. In an embodiment, the compressive strength or bearing capacity or penetration resistance of a composition is measured at 1 hour. 2 hours, 4 hours, 7 days, and 28 days after backfilling using ASTM WK 27337 or C403.

In an embodiment, the compressive strength of a composition of the present disclosure at 1 hour will be between about 3 psi and about 40 psi, between about 5 psi and about 35 psi, between about 7 psi and about 30 psi. In additional embodiments, the compressive strength of the composition at 1 hour will be greater than about 3 psi, will be greater than about 5 psi, will be greater than about 10 psi, will be greater than about 15 psi, will be greater than about 25 psi, will be greater than about 30 psi, or will be greater than about 40 psi.

In an embodiment, the compressive strength of a composition of the present disclosure at 1.5 hours will be between about 3 psi and about 40 psi, between about 5 psi and about 35 psi, between about 7 psi and about 30 psi. In additional embodiments, the compressive strength of the composition at 1 hour will be greater than about 3 psi, will be greater than about 5 psi, will be greater than about 10 psi, will be greater than about 15 psi, will be greater than about 25 psi, will be greater than about 30 psi, or will be greater than about 40 psi.

In an embodiment, the compressive strength of a composition of the present disclosure at 2 hours will be between about 10 psi and about 40 psi, between about 15 psi and about 35 psi, between about 20 psi and about 30 psi. In additional embodiments, the compressive strength of the composition at 2 hours will be greater than about 10 psi, will be greater than about 15 psi, will be greater than about 20 psi, will be greater than about 25 psi, will be greater than about 30 psi, will be greater than about 35 psi, or will be greater than about 40 psi.

In an embodiment, the compressive strength of a composition of the present disclosure at 4 hours will be between about 10 psi and about 70 psi, 10 psi and about 60 psi, between about 15 psi and about 50 psi, between about 15 psi and about 40 psi, between about 20 psi and about 30 psi. In additional embodiments, the compressive strength of the composition at 4 hours will be greater than about 10 psi, will be greater than about 15 psi, will be greater than about 20 psi, will be greater than about 25 psi, will be greater than about 30 psi, will be greater than about 35 psi, will be greater than about 40 psi or will be greater than about 50 psi. In an embodiment, the compressive strength of a composition of the present disclosure at 4 hours will be less than about 70 psi, less than about 60 psi, less than about 50 psi, less than about 40 psi, less than about 30 psi, or less than about 20 psi.

In an embodiment, the compressive strength of a composition of the present disclosure at 28 days hours will be between about 75 psi and about 300 psi, between about 100 psi and about 250 psi, between about 125 psi and about 200 psi. In additional embodiments, the compressive strength of the composition at 28 days will be greater than about 75 psi, will be greater than about 100 psi, will be greater than about 125 psi, will be greater than about 150 psi, will be greater than about 175 psi, will be greater than about 200 psi, or will be greater than about 250 psi. In certain embodiments, the compressive strength of the composition at 28 days will be less than about 300 psi, less than about 250 psi, less than about 200 psi, less than about 175 psi, less than about 150 psi, less than about 125 psi, or less than about 100 psi.

In an embodiment of the present disclosure, an important consideration is the possible re-excavation of the backfilled composition by standard or ordinary excavation equipment. One measure of how easily a previously backfilled composition can be removed is the Removability Modulus ("RE"). The Removability Modulus is a commonly used industry standard for assigning a value to how easily a backfilled composition can be removed. The lower the RE number the easier the backfilled composition can be re-excavated. The Removability Modulus can be determined by the following formula:

$$RE = \frac{W^{1.5} \times 104 \times C^{0.5}}{10^6}$$

$W$ = in-situ unit weight (pcf)

$C$ = 28 day compressive strength (psi)

In an embodiment of the present disclosure, the RE factor of a composition is between about 0.3 and between about 3.0, between about 0.5 and about 2.5, between about 0.7 and about 2.0, between about 0.8 and about 1.8, between about 0.9 and about 1.6, or between about 1.0 and about 1.4.

In additional embodiments of the present disclosure, the RE factor of a composition less than about 2.0, less than about 1.8, less than about 1.6, less than about 1.5, less than about 1.4, less than about 1.2, less than about 1.0, less than about 0.8, or less than about 0.6. In other embodiments of the present disclosure, the RE factor of a composition is greater than about 0.3, greater than about 0.6, greater than about 0.9, greater than about 1.1, greater than about 1.3, greater than about 1.5, or greater than about 1.7.

By using certain compositions of the present disclosure, it is possible to reduce the time from backfilling to paving of the backfilled surface. This reduction in time ultimately reduces the time from backfilling to intended use of the backfilled void, i.e., pedestrian traffic or vehicle traffic. In certain embodiments the backfilled void is suitable for paving (or equivalent) in less than about 4.0 hours, in less than about 3.5 hours, in less than about 3.0 hours, in less than about 2.5 hours, in less than about 2.0 hours, in less than about 1.5 hours, or in less than about 1.0 hour.

In certain embodiments of the present disclosure, a suitable composition can be defined by the water to fly ash ratio, e.g., when using no filler or when using non-cementitious fly ash filler. In these embodiments, a composition can have a range of water to fly ash ratios depending on the water demand of the fly ash, the desired flowability, the desired setting time and the desired final compressive strength. In certain embodiments, the water to fly ash ratio of a composition (W/FA) is between about 0.2 and about 1.0, between about 0.3 and about 0.8, or between about 0.4 and about 0.6. In additional embodiments, the water to fly ash ratio of a composition is greater than about 0.3, greater than about 0.5, greater than about 0.7 or greater than about 0.9. In other embodiments, the water to fly ash ratio is less than about 1.0, less than about 0.8, less than about 0.6, less than about 0.5, or less than about 0.4.

In certain embodiments of the present disclosure, a composition does not include one or more of the following: does not include a water reducer, does not include Portland cement, does not include a set retarder, does not include any cementitious material other than cementitious fly ash, does not include a filler, does not include aggregate, does not include gravel, does not include $CaCO_3$ or lime other than that present in the cementitious fly ash and/or filler, or does not include sand. Furthermore, a composition of the present disclosure does not include native soils in some embodiments.

In certain embodiments, the flowability of a composition can be determined by a slump test C143 or a slump flow as determined by C1611. A slump spread can equal roughly 2.5 times the D6103 spread, both in inches. In certain embodiments of the present disclosure, the slump cone spread of a composition is between about 10 and about 45 inches, between about 15 and about 40 inches, is between about 20 inches and about 30 inches. In additional embodiments, a composition of the present disclosure has a slump cone spread of less than about 50 inches, of less than about 40 inches, of less than about 35 inches, of less than about 30 inches, or of less than about 25 inches. In certain embodiments, the slump cone spread of a composition is greater than about 20 inches, is greater than about 25 inches, is greater than about 30 inches, is greater than about 35 inches, is greater than about 40 inches, or is greater than about 45 inches.

In additional embodiments, a composition of the present disclosure has a unit weight of between about 20 pcf and about 150 pcf, of between about 40 pcf and about 130 pcf, between about 60 pcf and about 100 pcf. In other embodiments, the unit weight of a composition is greater than about 30 pcf, greater than about 50 pcf, greater than about 70 pcf, greater than about 90 pcf, or greater than about 120 pcf. In still other embodiments, a composition has a unit weight of less than about 130 pcf, of less than about 110 pcf, of less than about 90 pcf, of less than about 80 pcf, of less than about 70 pcf, or of less than about 60 pcf.

The present disclosure also provides for a new method of determining a composition to reduce freeze thaw heave risk. For example, in an embodiment, the present disclosure provides a method for determining a suitable composition for preventing prevent ice lens formation comprising: determining the water demand of each fly ash within the composition; calculating the water demand for a combination of fly ashes; determining the compressive strength and densities for a combination of fly ashes; and determining the amount of air content necessary for the composition to have a compressive strength of between 10 and 60 PSI after 4 hours and a removability modulus of less than 1.8 after 28 days. In an additional embodiment, the method may further include identifying a group of fly ashes for use in the composition prior to determining the water demand of each fly ash within the composition.

Figure 9:
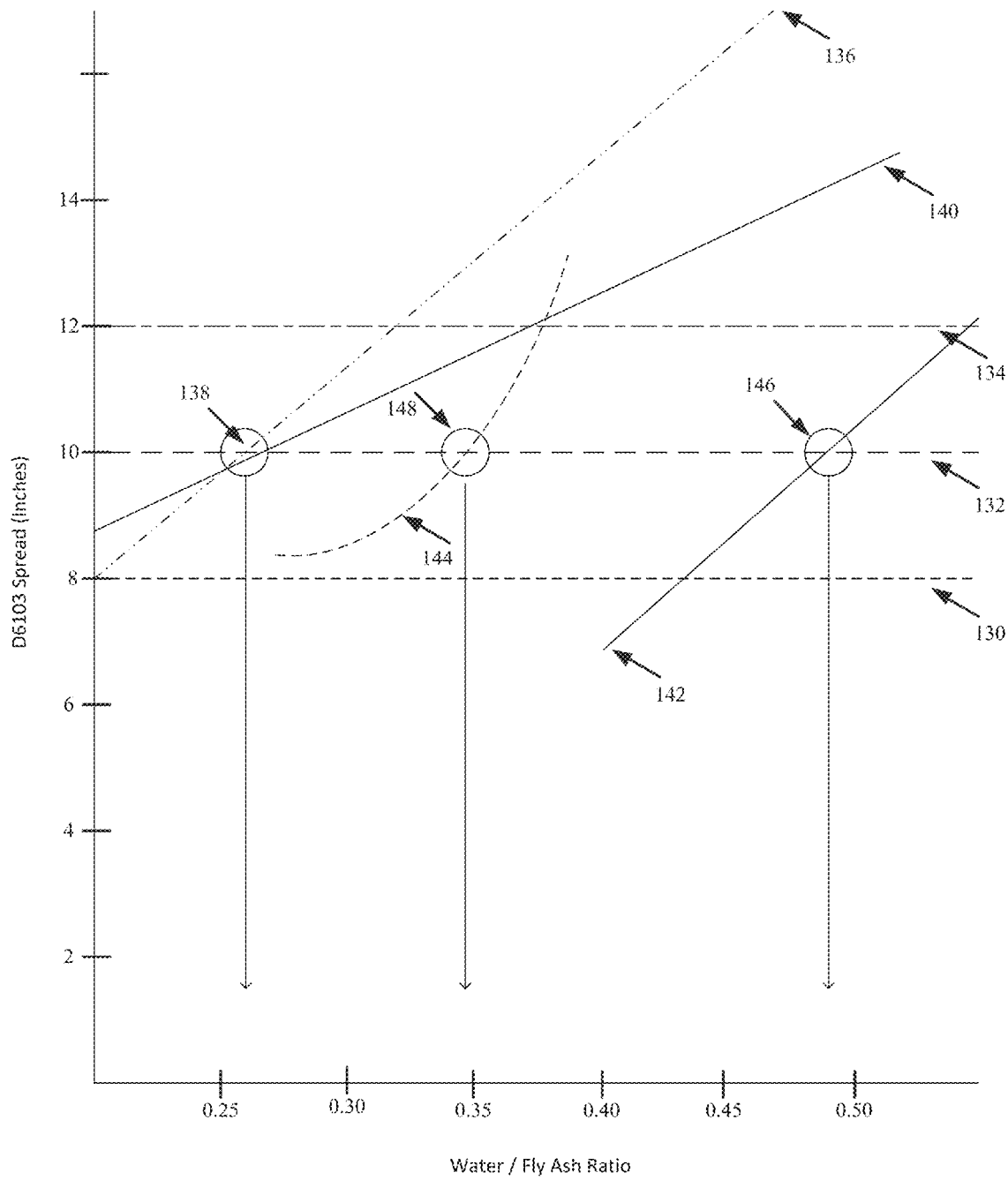
FIG. 9 illustrates the results of testing different fly ashes at different water to fly ash (W/FA) ratios to determine the resulting fluidity, i.e., spread for each fly ash.

In an embodiment, determining the water demand of each fly ash within the composition includes determining the water demand of cementitious fly ashes, specification grade or non-specification grade, as well as non-cementitious fly ashes, specification grade or non-specification grade. In an embodiment, determining the water demand includes adding water to a fly ash to achieve a spread of between about 6 inches and about 14 inches using a D6103 spread test. In additional embodiments, determining the water demand includes adding water to a fly ash to achieve a spread of between about 8 inches and about 12 inches or about 10 inches using a D6103 spread test. In some embodiments, determining the water demand includes plotting different water to fly ash ratios as a function of spread, e.g., as seen in FIG. 9.

Calculating the water demand for a combination of fly ashes can be determined in a number of fashions. In an embodiment, the water demand can be calculated for a combination of ingredients, including fly ashes and additional fillers, i.e., sand. In a specific embodiment, the water demand for a specific combination is determined by reference to the individual water demand of each fly ash or filler. For example, if a cementitious fly ash needs a 0.35 water/fly ash ratio to achieve a 10 inch spread and a non-cementitious fly ash needs a 0.48 water/fly ash ratio to achieve a 10 inch spread, then the total water demand for the combination of these two ingredients to have between a 8 and 12 inch spread is determined based on the known water demand for each fly ash and the proportion of each fly ash within the composition.

In an embodiment, determining the compressive strength and densities for a combination of fly ashes may include using ASTM C495 and C138 or other common tests in the industry. In this disclosure compressive strengths were measured using ASTM C495. In alternative embodiments, the compressive strength is determined using other methods apparent to one of skill in the art. In some embodiments, determining the compressive strength and densities for a combination of fly ashes includes plotting the results of compressive strength testing as a function of the water to fly ash ratio.

Determining the amount of air content necessary to achieve a predetermined compressive strength and removability modulus can include testing various or the same combination of fly ash and/or filler with various air contents to determine the air content necessary to achieve a desired compressive strength and/or removability modulus.

The present disclosure also provides for a novel method of backfilling a void. For example, in an embodiment, the present disclosure provides a method of backfilling a void to prevent ice lens formation comprising: mixing cementitious fly ash and filler to a predetermined ratio; adding water to the mix of cementitious fly ash and filler to make a wet mixture; adding air to the wet mixture, wherein the predetermined mix of cementitious fly ash and filler, the addition of water and the addition of air makes a composition having a compressive strength of between 10 and 60 PSI after 4 hours and a removability modulus of less than 1.8 after 28 days; and adding the composition to a void. In an additional embodiment, the method may include determining that the void is subject to freezing prior to mixing cementitious fly ash and filler to a predetermined ratio. If the void is not subject to freezing, a composition of the present disclosure provides an advantageous early set time and early strength while still maintaining a low RE by addition of air.

Mixing cementitious fly ash and filler to a predetermined ratio can include pre-mixing the dry ingredients prior to arriving at the construction site or mixing the dry ingredients at the construction site. In an embodiment, the composition does not have a filler.

In an embodiment, the addition of water to the mix of cementitious fly ash and filler occurs at the construction site. However, in other embodiments, the water is added prior to arrival at the construction site, e.g., in the drum of a ready mix truck. The addition of water may occur inside the drum of a volumetric mixing truck or may occur as the dry mix leaves or after the dry mix has left the mixing truck, e.g., while the dry mix is moving thru a spiral auger.

In some embodiments, the addition of air to the wet mixture can occur simultaneously with the addition of water to the dry ingredients or after the addition of water to the dry ingredients. In some embodiments, a cellular foam providing the air content is placed directly onto a wet mixture comprising the cementitious fly ash, filler and water. In other embodiments, the air content is provided by the addition of a dry surfactant to the cementitious fly ash and/or filler prior to addition of water or by using a liquid air entraining admixture during mixing.

In several described embodiments, the completion of the backfill composition occurs at the construction site, e.g., by addition of water and/or air content; however, in other embodiments, the water, air content (e.g., cellular foam), cementitious fly ash and/or filler may be premixed offsite. In this embodiment, a slower set time—thereby allowing transportation of the premixed composition to the construction site—can be achieved using a retarding agent. In an embodiment, the retarding agent is citric acid or boric acid (or a combination thereof) while in other embodiments the retarding agent is any agent capable of retarding the set time of the composition.

The addition of the composition to the void can be achieved using buckets, chutes, pumps, conveyors, hoses, augers or any method routinely used with Portland cement based compositions.

Referring now to the figures, FIG. 1 illustrates the creation of horizontal cracks by a small compactor on a backfilled trench as a matter of time and depth. The illustrated trench is roughly 8 ft deep from the surface of the backfill 100 to the bottom of the trench 102. The native soil 104 sits under the trench. A small compactor 106 begins to compact the asphalt trench patch along the surface 100 at different times after the composition (Mix B) is placed in the trench. With earlier starting times (e.g., 2.0 hours or 4.0 hours), the vibration can create horizontal fractures 118 deeper, since the strength of the backfill near the surface cannot dissipate the vibrations as well (e.g., to a depth of 5.5 feet if starting at 2.0 hours and depth of 4.0 feet if starting at 4.0 hours). As the composition becomes stronger over time, fractures 118 that result from the small compactor 106 are nearer the surface and do not extend as deep. With a starting time (e.g., 12 hours) that allows sufficient strength in the composition to resist all horizontal fractures, pavement replacement can safely occur. An attempt to replacement pavement at any time earlier than 12 hours results in horizontal crack formation, which can ultimately lead to frost heave, due to ice lens development.

Figure 2:
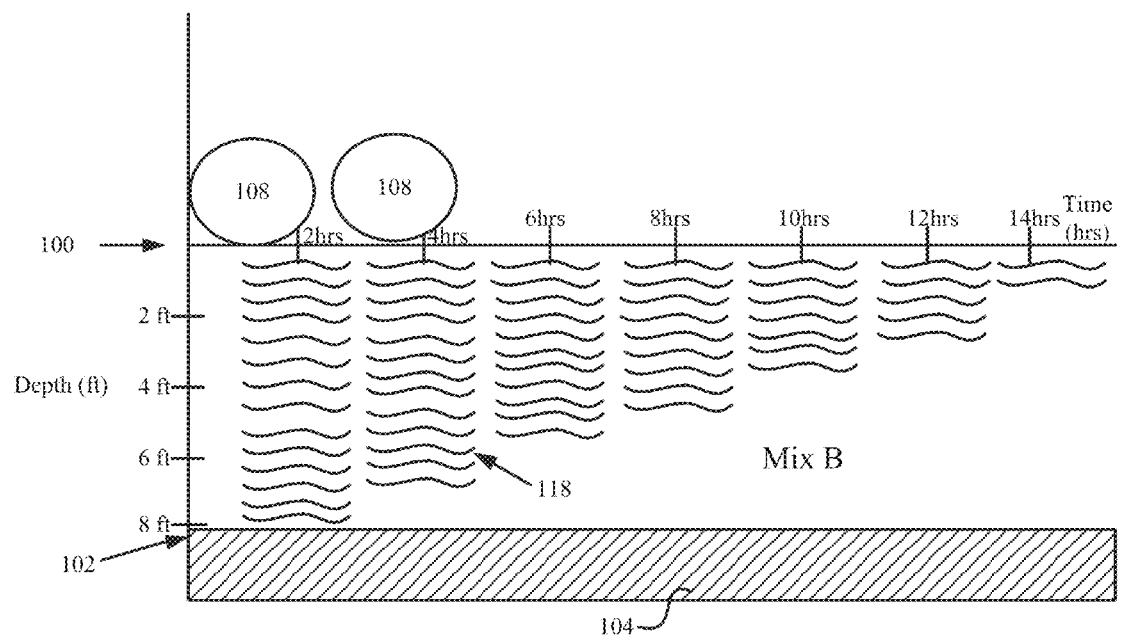
FIG. 2 illustrates the creation of horizontal cracks by a large compactor on a backfilled trench as a function of time.

FIG. 2 illustrates a larger, heavier, more powerful compactor as discussed in FIG. 1. Like FIG. 1, the illustrated trench is roughly 8.0 ft deep from the surface of the backfill 100 to the bottom of the trench 102. The native soil 104 sits under the trench. A large compactor 108 begins to compact the asphalt trench patch along the surface 100 at different times after the composition (Mix B) is placed in the trench. With earlier starting times (e.g., 2 hours or 4 hours), the vibration can create horizontal fractures 118 deeper, since the strength of the backfill near the surface cannot dissipate the vibrations as well (e.g., to a depth of 8.0 feet if starting at 2 hours and depth of 7.0 feet if starting at 4 hours). As the composition becomes stronger over time, fractures 118 that result from the large compactor 108 are nearer the surface and do not extend as deep. With a starting time (e.g., greater than 14 hours) that allows sufficient strength in the composition to resist all horizontal fractures, pavement replacement can safely occur. An attempt to replace pavement at 14 hours or earlier in this hypothetical example results in horizontal crack formation, which can ultimately lead to frost heave. In this figure, with the same mix as FIG. 2, fractures are generated deeper with any given start time with a larger compactor.

FIG. 3 illustrates the previously depicted small compactor 106 of FIG. 1 and the same conditions as FIG. 1 but uses a different composition, i.e., Mix A, to fill the trench. Mix A sets up and hardens faster than the Mix B used in FIG. 1 and FIG. 2. At a faster setting time due to a faster setting composition, the small compactor 106 will induce shallower horizontal fracture at any given start time, e.g., 3.0 feet at 2 hours and 2 feet at 4 hours. With a faster setting Mix A, the safe starting time has been reduced from 12-hours (e.g., FIG. 1) to 8-hours using hypothetical Mix A over Mix B.

FIG. 4 illustrates the previously depicted large compactor 108 of FIG. 2 and the same conditions as FIG. 2 but uses a different composition, i.e., Mix A, to fill the trench. Mix A sets up and hardens faster than the Mix B used in FIG. 1 and FIG. 2. At a faster setting time due to a faster setting composition, the large compactor 108 will induce shallower horizontal fracture at any given start time, e.g., 5.0 feet at 2 hours and 4.0 feet at 4 hours. With a faster setting Mix A, the safe starting time has been reduced from greater than 14 hours (e.g., FIG. 2) to 14 hours using hypothetical Mix A over Mix B.

Figure 5:
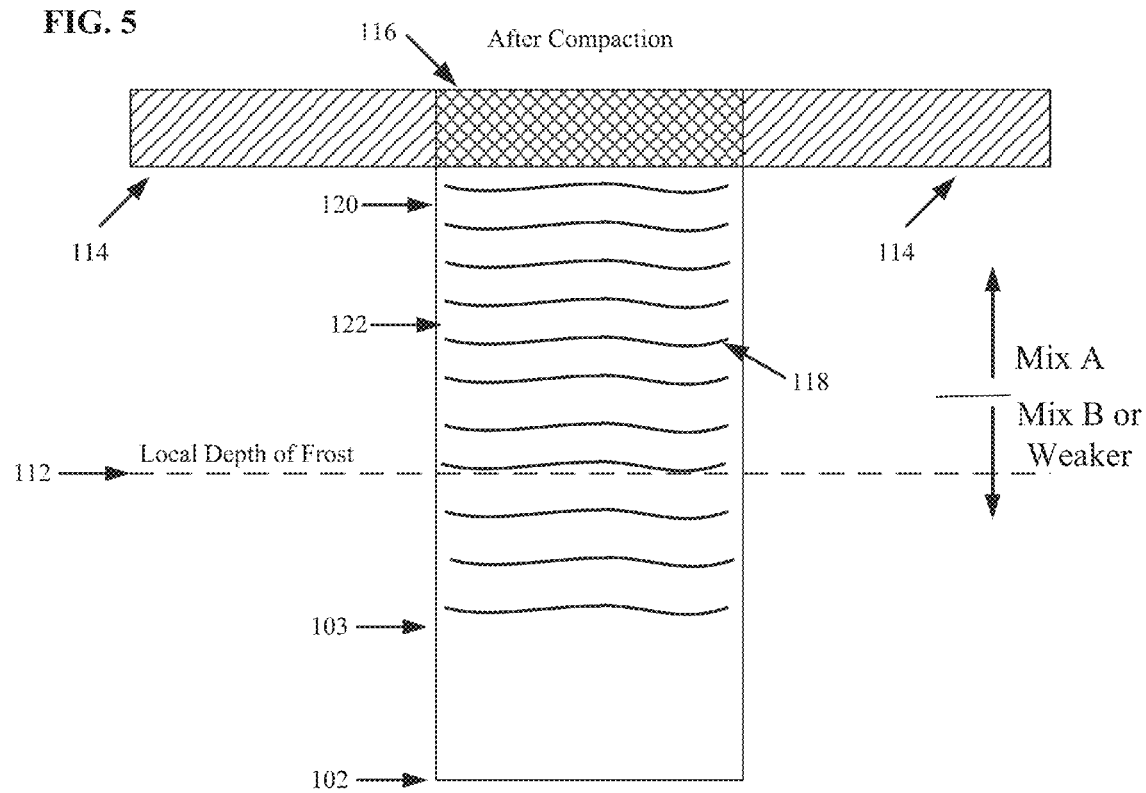
FIG. 5 is a close up view of the horizontal fractures discussed in FIGS. 1 through 4.

FIG. 5 illustrates a backfilled trench 120 that has been paved 116 to match the surrounding surface pavement 114. However, the paving occurred too soon and induced horizontal fractures 118 to the bottom of the trench 102 or to a depth above the bottom of the trench 103, both above and below the frost line 112. The previously described horizontal fractures 118 (e.g., FIGS. 1-4) are a result of paving occurring at a time from backfill when the backfill composition had insufficient strength to resist horizontal shear forces. These fractures 118 can occur below the local depth of frost penetration 112 in a severe winter, depending on the mixture and the compaction time/equipment.

Figure 6:
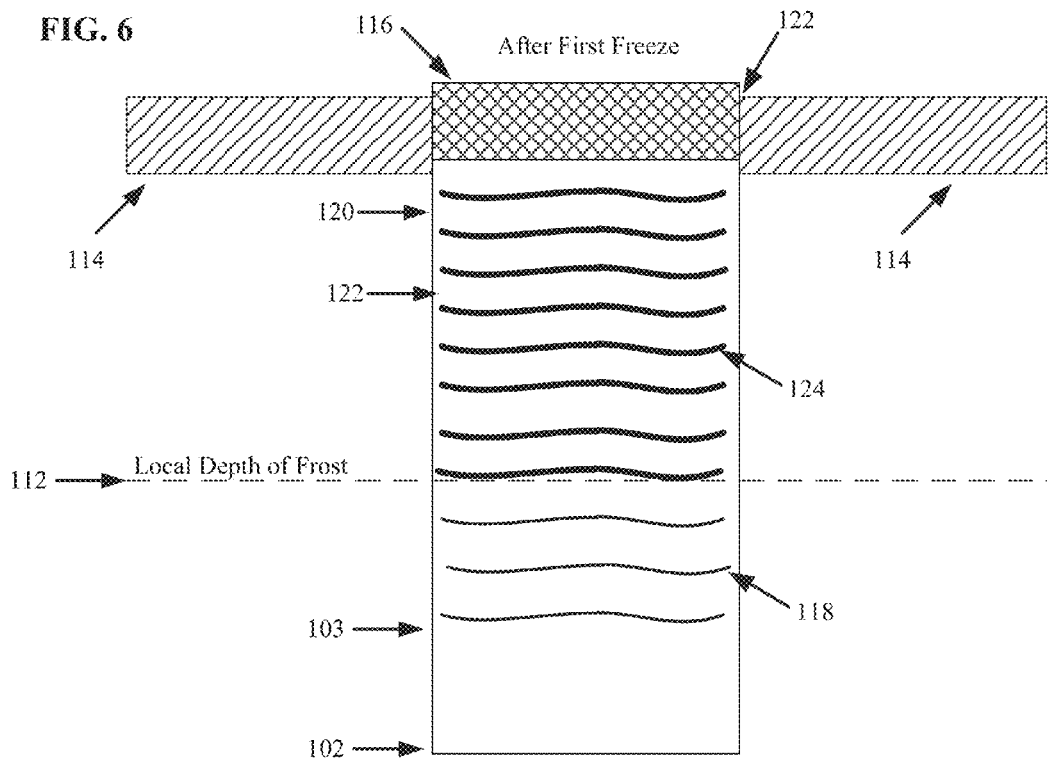
FIG. 6 illustrates the same horizontal fractures of FIG. 5 after saturation with infiltrating water and the first freeze cycle.

FIG. 6 illustrates a backfilled trench 120 of FIG. 5 following a freeze cycle. The horizontal fractures 118 of FIG. 5 had become saturated with infiltrating water—from the surface and/or ground water (e.g., 122)—and expanded after the first freezing cycle to become larger fractures 124. The 11% expansion of water from freezing has enlarged the horizontal fractures 124 above the depth of frost penetration. The resulting enlargement/expansion of the horizontal fractures 124 has caused frost heave, pushing the original backfilled trench pavement 116 above the surrounding surface pavement 114.

Figure 7:
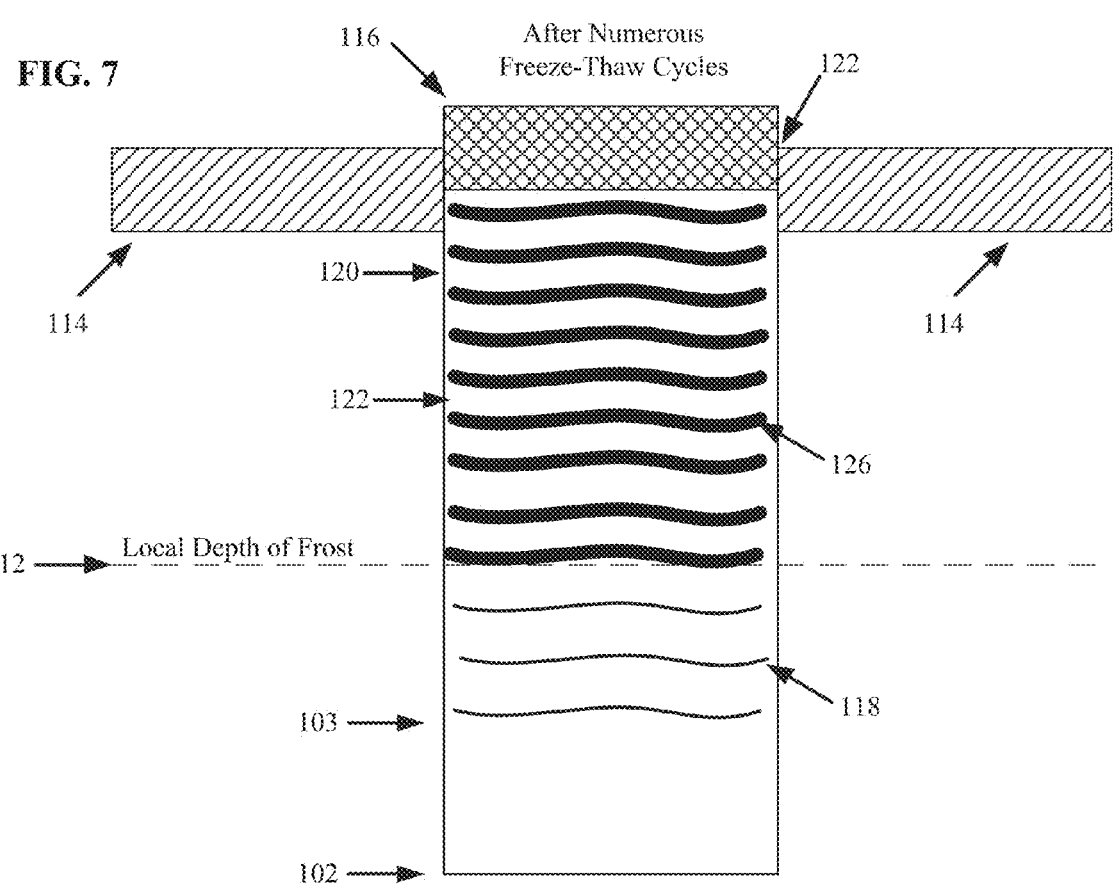
FIG. 7 illustrates the horizontal fractures of FIG. 5 after several cycles of saturation with infiltrating water followed by freeze thaw cycles.

FIG. 7 illustrates a backfilled trench 120 of FIGS. 5 & 6 following several freeze thaw cycles. The horizontal fractures 118 of FIG. 5 have become saturated with infiltrating water (e.g., 122) and expanded after multiple freezing cycles to become larger fractures 126. The 11% expansion of water from freezing has enlarged the horizontal fractures 126 above the depth of frost penetration. The resulting enlargement/expansion of the horizontal fractures 126 has worsened the frost heave of FIG. 6, pushing the original backfilled trench pavement 116 even farther above the surrounding surface pavement 114. The height of heave of the pavement patch (e.g., height between 116 and 114) is approximately equal to the sum of the thicknesses of all ice lenses formed in the compaction fractures below 126.

Figure 8:
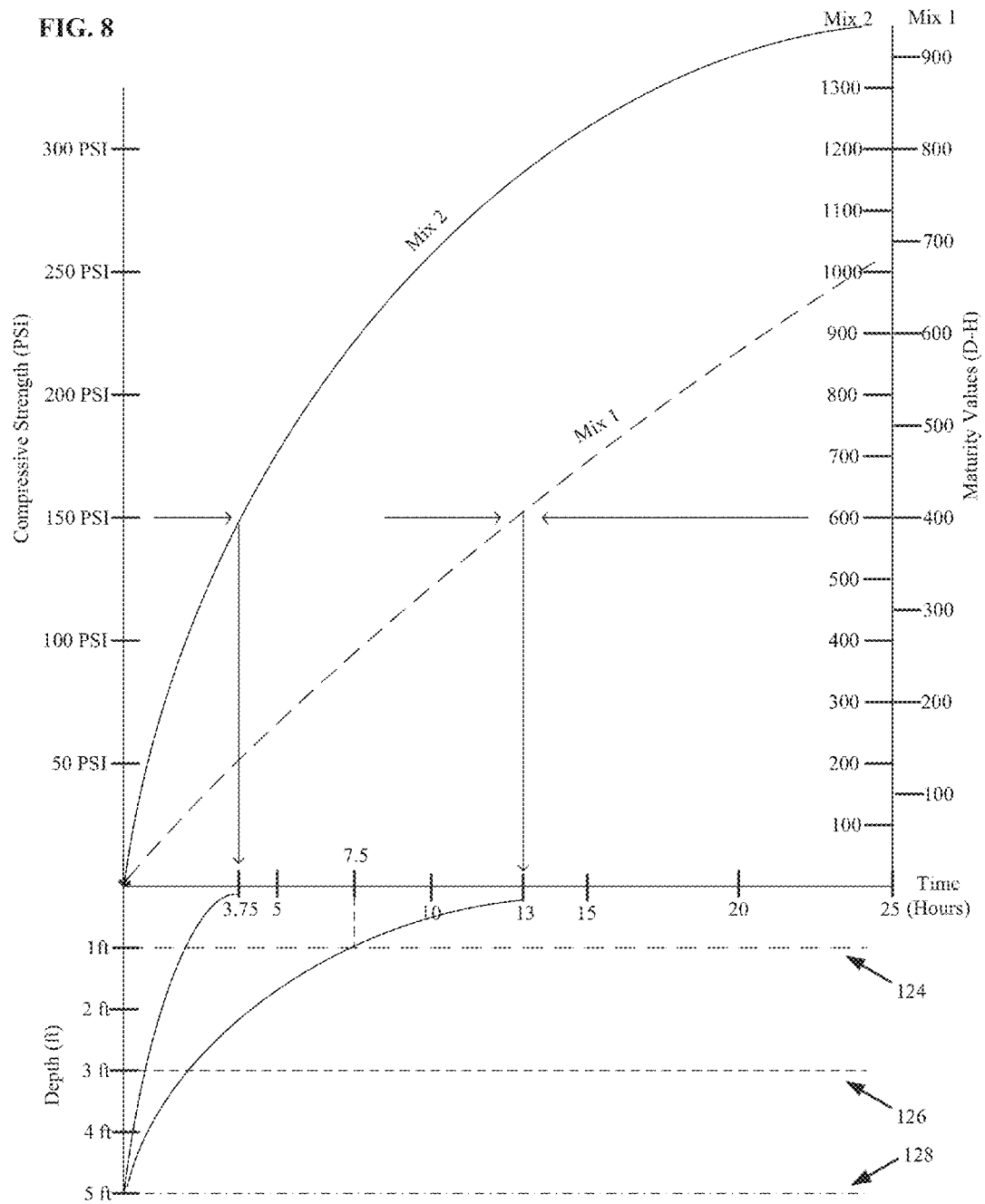
FIG. 8 illustrates the hypothetical strength development curves of two different backfill compositions based on both compressive strength (PSI) and the maturity method (degree-hours), as well as the depth of fracturing of each mix with the same compactor as function of starting time.

FIG. 8 illustrates strength development curves for two different hypothetical compositions (e.g., Mix 1 and Mix 2) without air entrainment, based on both compressive strength (psi), the maturity method (degree-hours), as well as the depth of fracturing of these two mixtures with a compactor (same for both) as a function of starting time. Mild compaction problems 124 (e.g., fractures are shallow and less than 1 foot), moderate compaction problems 126 (e.g., fractures extend to a depth of 3 feet) and severe compaction problems 128 (e.g., fracture extend to a depth of 5 feet) are determined by looking plotting the depth of horizontal fractures as a function of time. Even mild compaction problems can result ice lens formation and frost heave.

Still generally referring to FIG. 8, in an embodiment, the first step in reducing freeze-thaw heave risk with backfilled trenches is to conduct an on-site test with a given compactor and a given composition. In time, various size ranges of compactors can be tested and in an embodiment of the present disclosure quantified into groups, e.g., small, medium and large, based on test results and manufacturer's output ratings of compactive energy. Similarly, in an embodiment of the present disclosure, compositions can be qualified, e.g., slow, medium, fast and extra fast, based on the time to achieve a specified strength level, i.e., 4-hour/200 psi mix. Such equipment and mix categories can facilitate proper ordering and placement of the correct composition, while successfully reducing freeze-thaw heave risk.

For example, a suitably-sized test trench is excavated and filled with a composition of the present disclosure, as indicated by Mix 1 in FIG. 8. Maturity probes are inserted at various depths in the composition and activated at the time of placement. At various times along the length of the backfilled trench, the compactor is operated for a suitable number of passes to properly compact asphalt. The next day, coring is performed to determine the depth of compaction fractures associated with the different starting times. These fracture depths vs. starting-times are plotted on a graph, as shown in FIG. 8. Typically, the safe starting time for any given compactor & mixture combination would be the first time that no compaction fractures can occur. However, pavement patch materials could be compacted if the depth of the patch materials exceeds the local frost depth; any compaction fractures below the final frost depth would not contribute to deleterious heaving.

Still referring to FIG. 8, based on previously performed laboratory testing of Mix 1, the strength development versus time curve can be graphed as show in FIG. 8, both in terms of compressive strength (psi), and Maturity Values (degree-hours) recorded in a test cylinder. With this correlation data, the compositions' actual strength (150 psi) in the trench experiment can be properly estimated, based on the maturity probes in the trench fill (400 degree-hours) and using the correlation graph. While the maturity values from test cylinders at a given time will not match the trench values at the same time, (due to heat-generation of mass-effects of samples), the trench values can be used on the graph to determine the time/strength mixture needed. Thus, strength required to resist compaction fractures can readily be determined to specify mixture performance vs. a desired starting time.

Still referring to FIG. 8, the hypothetical required compressive strength was determined to be 150 psi, and the safe starting time for Mix 1 was 13 hours. If this was too long to repair the trench and open the street to traffic, a faster mix could be selected. Based on a similar strength-development curve for Mix 2, 150 psi should be achieved (under laboratory conditions) within 3.75 hours, although at a different Maturity value (600 degree-hours) than Mix 1 exhibited at 150 psi. Hence, a safe starting time for compaction would be fieldverified when the maturity probes in the trench filled with Mix 2 achieve the required degree-hour value corresponding to 150 psi for Mix 2 (600 degree-hours).

FIG. 9 illustrates graphically the results of testing different fly ashes at different W/FA ratios to determine the resulting fluidity using ASTM D6103. The following cementitious fly ashes were tested: Gentleman 136, California 140, and Arapahoe 144. In addition, Valmont Class F fly ash 142 was tested. In this case, the spread was determined by lifting an open-ended 3 inch diameter by 6 inch tall cylinder mold (ASTM D6103). This size is convenient for smaller laboratory batches and can be reasonably correlated to using a 12 inch high concrete slump cone as typical for self-consolidating concrete mixtures. As shown in the graph, different fly ashes have different "water demand" curves (e.g., 136, 140, 142, and 144), to achieve a desired fluidity; in this case, a 10" spread 132 is desired, with maximum spread of 12 inches 134 and a minimum spread of 8 inches 130. The graphs can be used to estimate the W/FA ratio at the exact spread desired. For example, the desired W/FA ratio for a 10 inch spread of California Class C ash 136 is roughly 0.26 as indicated by the intersection point 138 of the California Class C ash graph 136 with the 10 inch spread line 132. The same determination is possible for the other graphed fly ashes, e.g., 138, 148 and 146.

Figure 10:
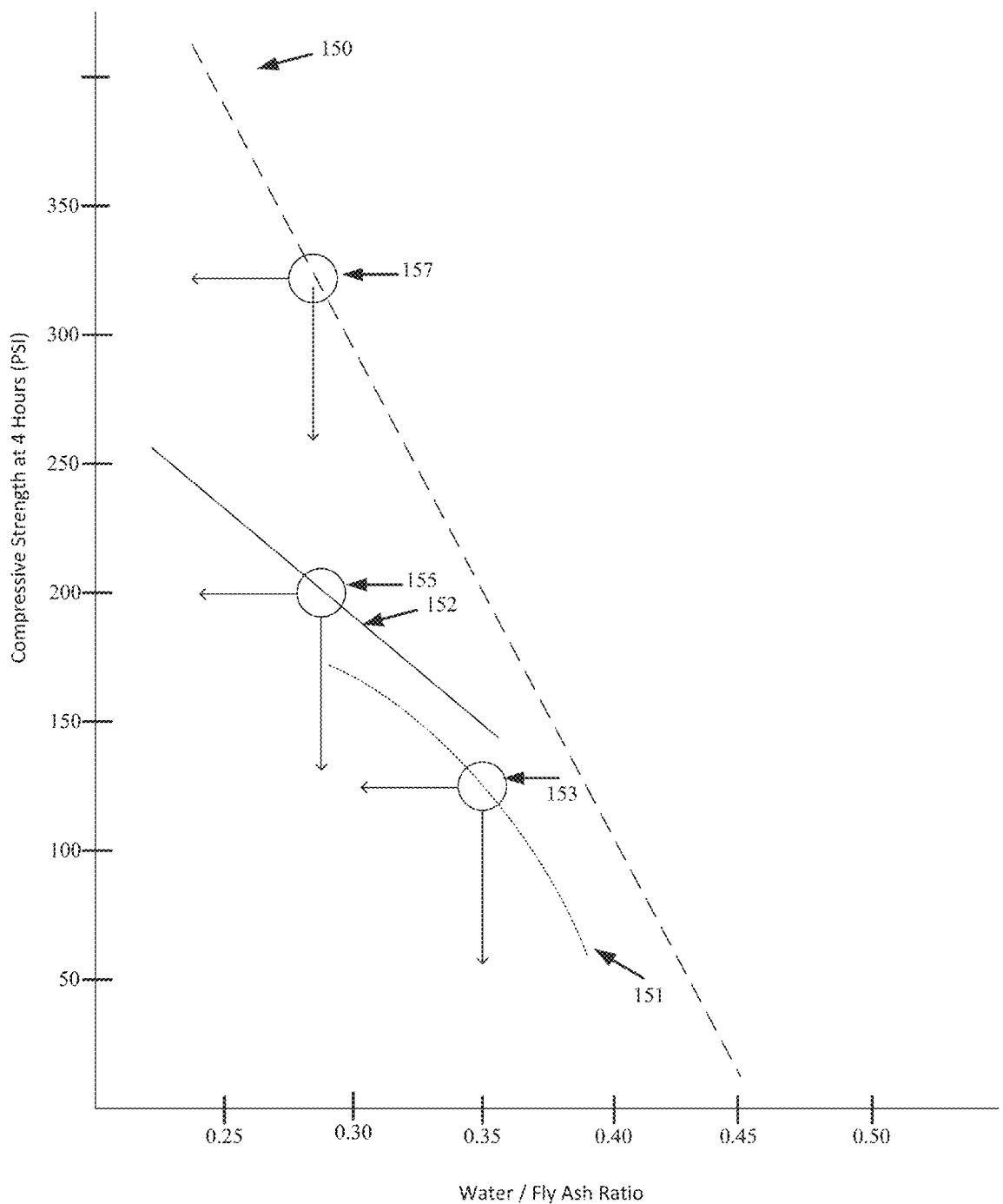
FIG. 10 illustrates the 28 day compressive strengths of various cementitious fly ashes, e.g., Class C fly ash, as a function of the water to fly ash ratio (W/FA) with desired fluidity identified by each circle.

FIG. 10 illustrates typical 4-hour compressive strengths of various cementitious fly ashes as a function of their W/FA ratios. After strength testing has occurred, the estimated strength at the W/FA ratio associated with their desired 10 inch spread can be estimated from the chart. For example, at a 10 inch spread, Arapahoe 151 has a strength of 125 psi as indicated by the circle at 153. For example, at a 10 inch spread, California 152 has a strength of 200 psi as indicated by the circle at 155. For example, at a 10 inch spread, Gentlemen 150 has a strength of 320 psi as indicated by the circle at 157.

FIG. 11 illustrates how testing the water demand of each fly ash (cementitious or non-cementitious) separately can be useful in determining the estimated 4-hour strength of various blends of Class C & F fly ashes. In this case, depending on the blend, the W/FA ratio of the blend is first mathematically estimated. Since the non-cementitious fly ash does not influence early strengths, the estimated blended W/FA can be used with the strength-W/FA curve for the cementitious fly ash to estimate the blended strength. For example, a 50-50% blend of Gentleman and Valmont is estimated with a W/FA ratio of 0.39, resulting in 120 psi at 4-hours.

Figure 12:
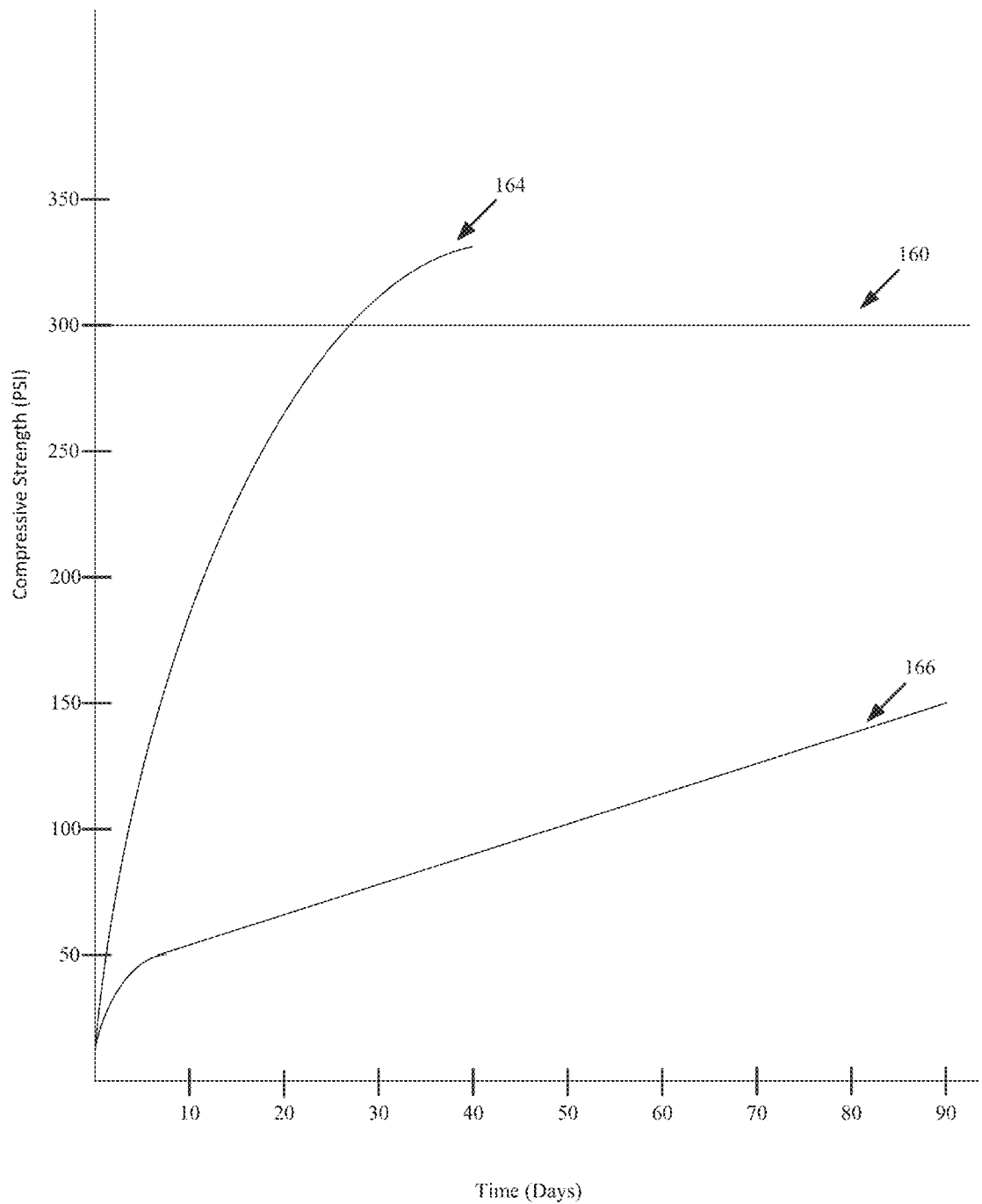
FIG. 12 illustrates strength versus time curve of compositions from the '422 patent.

FIG. 12 illustrates the strength vs. time curve taught by the '422 patent 166. One way to reach higher early strengths would be to use higher cementitious fly ash blends and/or lower water contents; however these would result in ultimate strengths greater than desired or allowed by ACI 229. For example, a 1:1 Gentleman to Valmont blend 164 results in earlier higher strengths but ultimately results in a final strength above that recommended by ACI 229, represented by 160.

Figure 13:
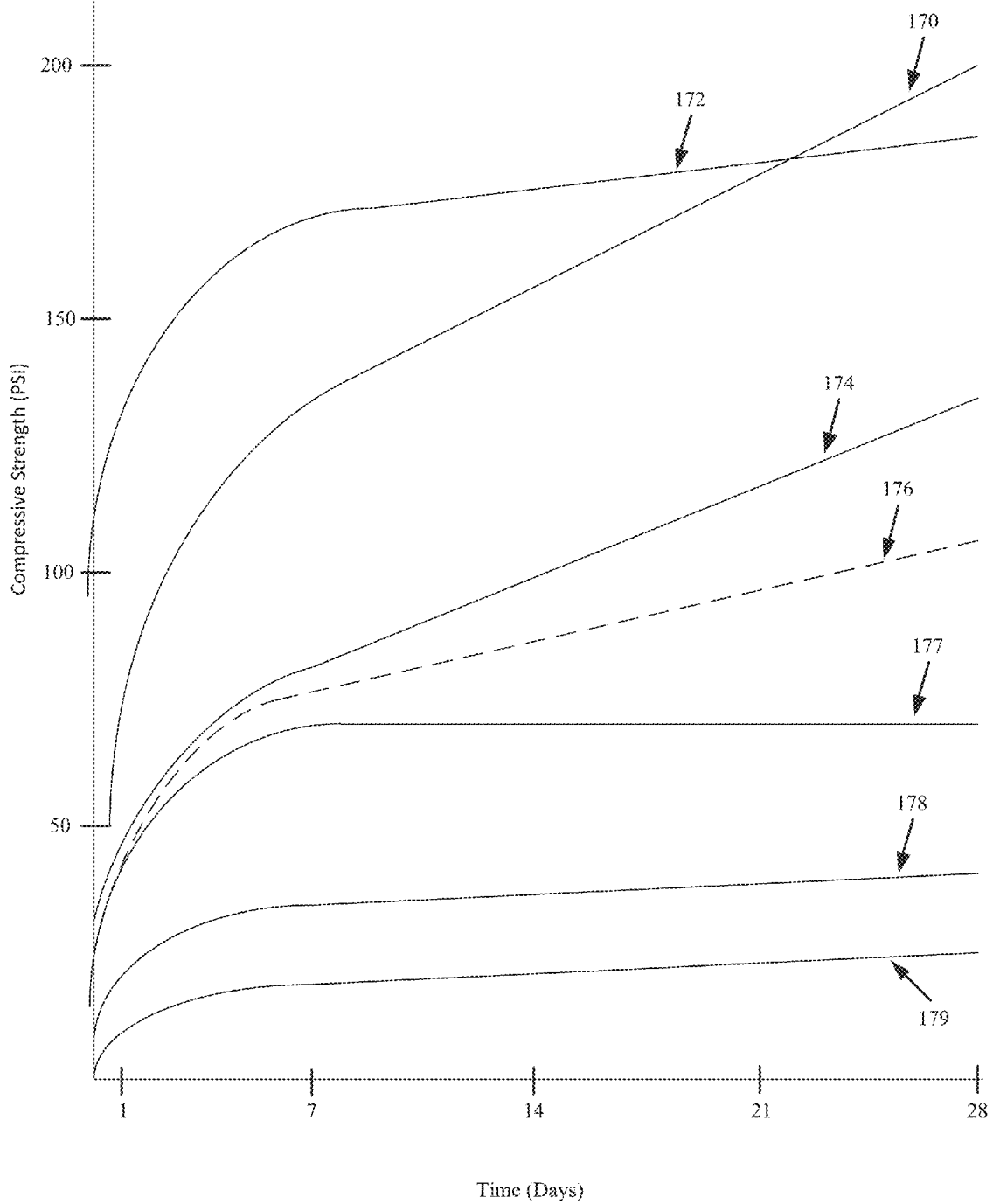
FIG. 13 illustrates strength versus time curves of various compositions from the present disclosure in relation to a composition from the '422 patent.

FIG. 13 illustrates strength curves at varying air contents, created by adding increasing amounts of cellular foam to compositions of the present disclosure. For example, a composition of the '422 patent with no cellular foam 176, a composition of the present disclosure entrained with cellular foam resulting in 14% air 172, a composition of the present disclosure with no air 170, a composition of the present disclosure entrained with cellular foam resulting in 28% air 174, a composition of the present disclosure entrained with cellular foam resulting in 33% air 177, a composition of the present disclosure entrained with cellular foam resulting in 41% air 178 and a composition of the present disclosure entrained with cellular foam resulting in 54% air 179.

Still referring to FIG. 13, the optimization process will include balancing higher early strengths and acceptable ultimate strengths. In this case, a moderately-reacting cementitious fly ash (Arapahoe) was used without air entrainment or with varying degrees of air entrainment, mimicking the early strengths of the '422 non-air formulation 176. In alternative embodiments, more reactive fly ashes (such as Gentleman) can be used to achieve faster-setting times and higher-early strengths, but still effectively limited ultimate strengths with sufficiently high air contents.

Laboratory and field testing has shown that the setting time is comparable with various air contents: however the initial early strengths are affected by higher air contents, which can impact early placement of street repair patches.

TABLE 1

Arapahoe-Valmon 50-50 Mixes, varying air content

| UW | % Air | 4 Hour | 1-day | 7-day | 28-day | RE | FIG. 13 No. |
|---|---|---|---|---|---|---|---|
| 101 | 0 | 56 | 88 | 142 | 200 | 1.50 | 170 |
| 87 | 14 | 56 | 125 | 155 | 182 | 1.14 | 172 |
| 73 | 28 | 38 | 54 | 81 | 136 | 0.75 | 174 |
| 68 | 33 | 25 | 48 | 75 | 70 | 0.49 | 177 |
| 60 | 41 | <20 (14) | 33 | 36 | 41 | 0.31 | 178 |
| 46 | 54 | <20 (9) | <20 (16) | 24 | 26 | 0.17 | 179 |

As shown in the table above, the RE of foamed compositions decreases with increased air-contents, both because of lower unit weights and lowered compressive strengths. Field trials with compositions foamed to various air contents, then later excavated with a tractor backhoe confirmed the relative ease of removing hardened compositions with higher air.

Figure 14:
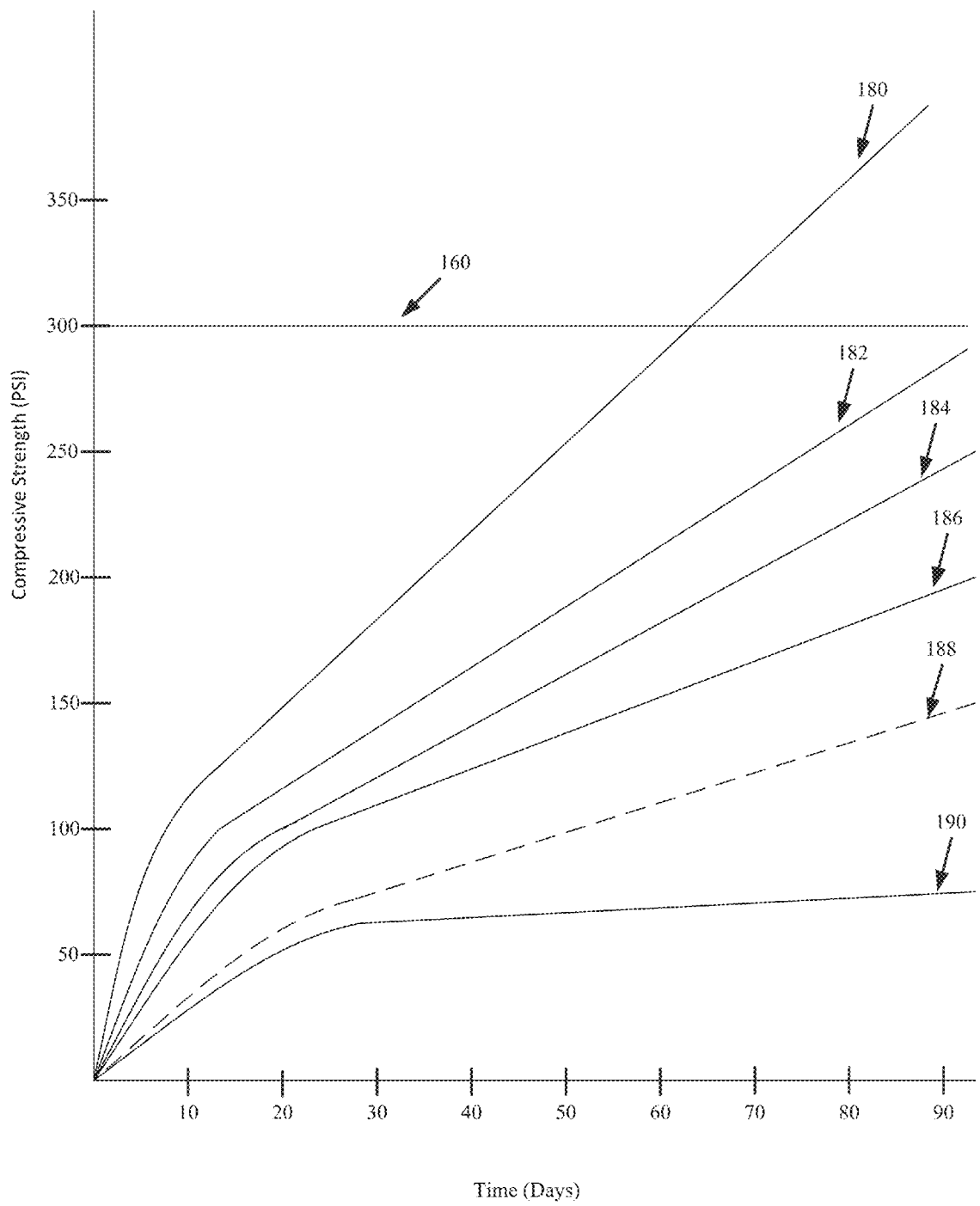
FIG. 14 illustrates hypothetical strength versus time curves of various compositions from the present disclosure in relation to a composition from the '422 patent.

FIG. 14 illustrates a hypothetical graph, in an embodiment, demonstrating the compressive strength as a function of time for compositions with varying air content. For example, a composition of the '422 patent with no cellular foam 188, a composition of the present disclosure with no air 180, a composition of the present disclosure with low air content 182, a composition of the present disclosure with medium air content 184, a composition of the present disclosure with high foam content 186 and a composition of the present disclosure with too much air content 190. The ACI 229 strength limit is represented by 160.

Figure 15:
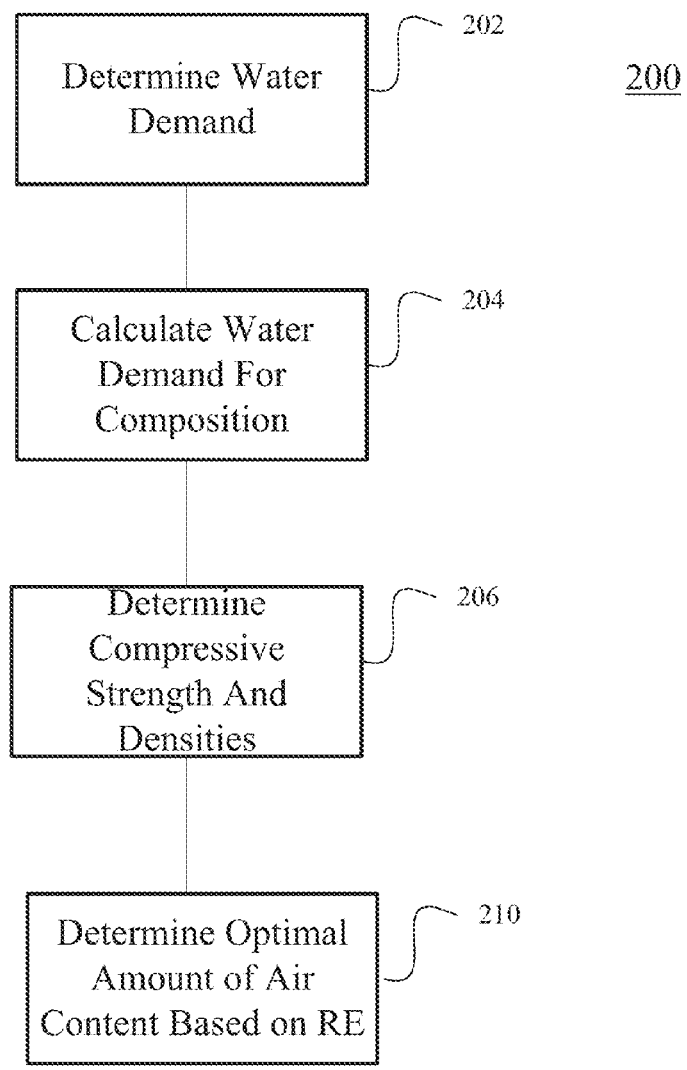
FIG. 15 illustrates an embodiment of the steps for determining an optimum composition to meet a specified setting time and removability modulus.

FIG. 15 illustrates an embodiment of a method 200 of the present disclosure. To increase the field performance and lab predictability of test results, a better mix design & testing protocol was needed. At step 202, fly ashes of interest are tested separately for consistency versus water demand. Test results of slump-cone and/or 3×6 cylinder spreads (inches) will be graphed at varied water contents somewhat above, at, and somewhat below the desired consistency of the composition (e.g. FIG. 9). A curve can be fit through the measured data points, and a specific water demand can be determined at the desired consistency (e.g., a 26 inch cone-spread or 10 inch cylinder spread). In addition, at step 202, the water demand for a filler other than non-cementitious fly ash can be determined. At step 204, the estimated water demand of a composition, i.e., 30% cementitious fly ash and 30% non-cementitious fly ash, is determined by proportioning of the separate water demands determined in step 202.

At step 206, the compressive strengths and densities of a composition is determined. Compressive strength versus time testing is performed on various compositions, e.g., same composition with different water/fly ash ratios, to determine the compressive strengths at different water contents. These tests can range from a composition with using only cementitious fly ash at the desired consistency to a composition with the highest water demand estimated for the blend of cementitious fly ash and non-cementitious fly ash or filler). Since the final resulting compressive strength of the blended fly ash mixture is dependent on the actual water/fly ash ratio acting on the cementitious material, compressive strengths of any suggested blend can be estimated to determine if further verification testing of the blend is warranted.

At step 210, the amount air content needed for composition from step 206 to have a desired RE is determined. For example, a composition from step 206 may set in the desired time, e.g., 30 minutes, but may have a high final compressive strength resulting in a high RE. Thus, the amount of air content, e.g., cellular foam, necessary to reduce the final compressive strength is determined. In some embodiments, the final compressive strength and unit weight is retested after determining the final air content.

The time of initial set is determined when the weight of the pocket penetrometer (approximately 0.2 lb) was supported by the surface of the composition on a diameter of 0.25 inch; this represents a penetration pressure of approximately 4.0 psi. Further values are measured by pushing the penetrometer into the fly ash mixture.

Figure 16:
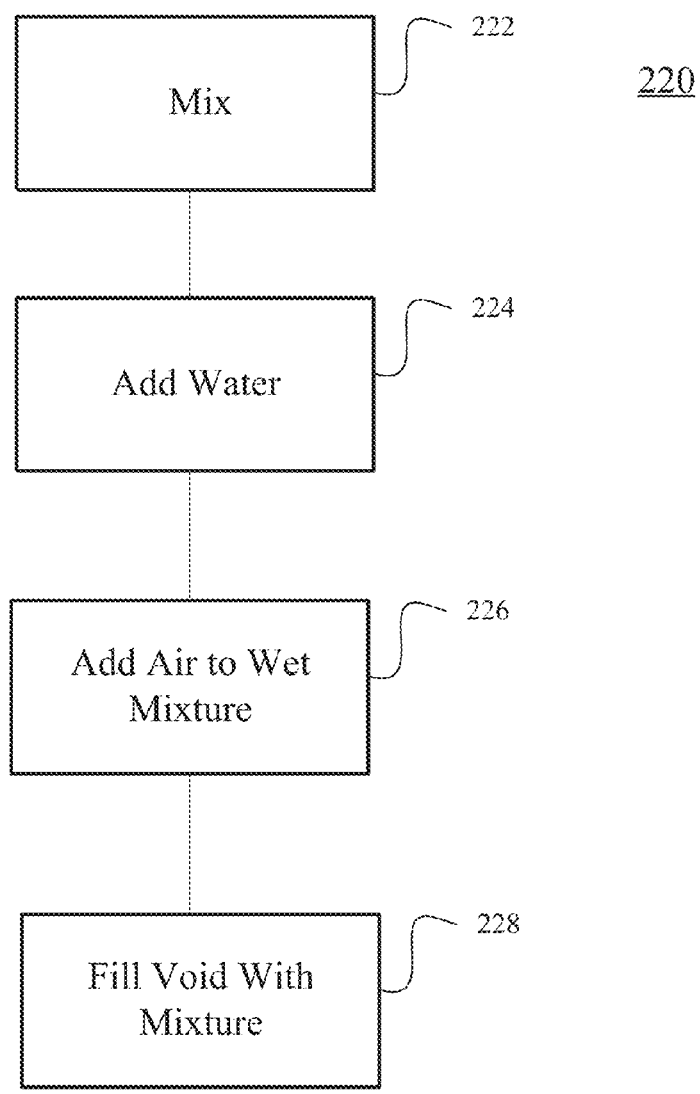
FIG. 16 illustrates an embodiment of the steps for backfilling a void with a composition of the present disclosure.

FIG. 16 illustrates an embodiment of a method 220 presently disclosed. At step 222, the dry ingredients are combined to a desired ratio. In an embodiment, the dry ingredients comprise cementitious fly ash and non-cementitious fly ash. In additional embodiments, the dry ingredients comprise cementitious fly ash, non-cementitious fly ash and additional fillers, e.g., sand. In some embodiments, the dry ingredients are only cementitious fly ash. In other embodiments, the dry ingredients do not contain non-cementitious fly ash. In an embodiment, step 222 occurs offsite, i.e., not at the construction site.

At step 224, water is added to the dry ingredients. At step 226, air is added to the wet mixture, e.g., cellular foam is added to the wet mixture. At step 228, the wet mixture with air content is added to the desired void resulting in a backfill composition stronger than native soils and structural fills but not harder to excavate.

Figure 17:
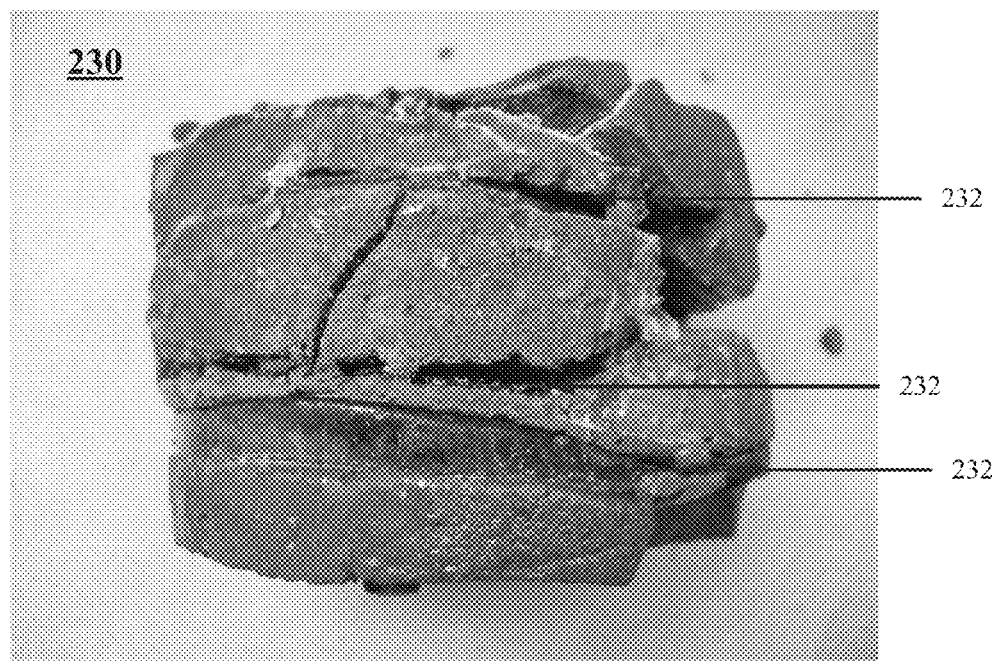
FIG. 17 is an ice lens formation in a composition as suggested by the '422 patent.

FIG. 17 is a picture of ice lens formation in a composition of the '422 patent. A 3.75 inch diameter core 230 was taken from backfill using a composition as taught by the '422 patent. The larger, lower ice lens 232 is 0.40 inches thick. The ice lenses 232 formed by the subsequent filtration of water into the horizontal cracks in the backfill composition combined with multiple freeze thaw cycles. In FIG. 17, multiple ice lenses of varying thicknesses have formed in the horizontal cracks of the backfill.

Figure 18:
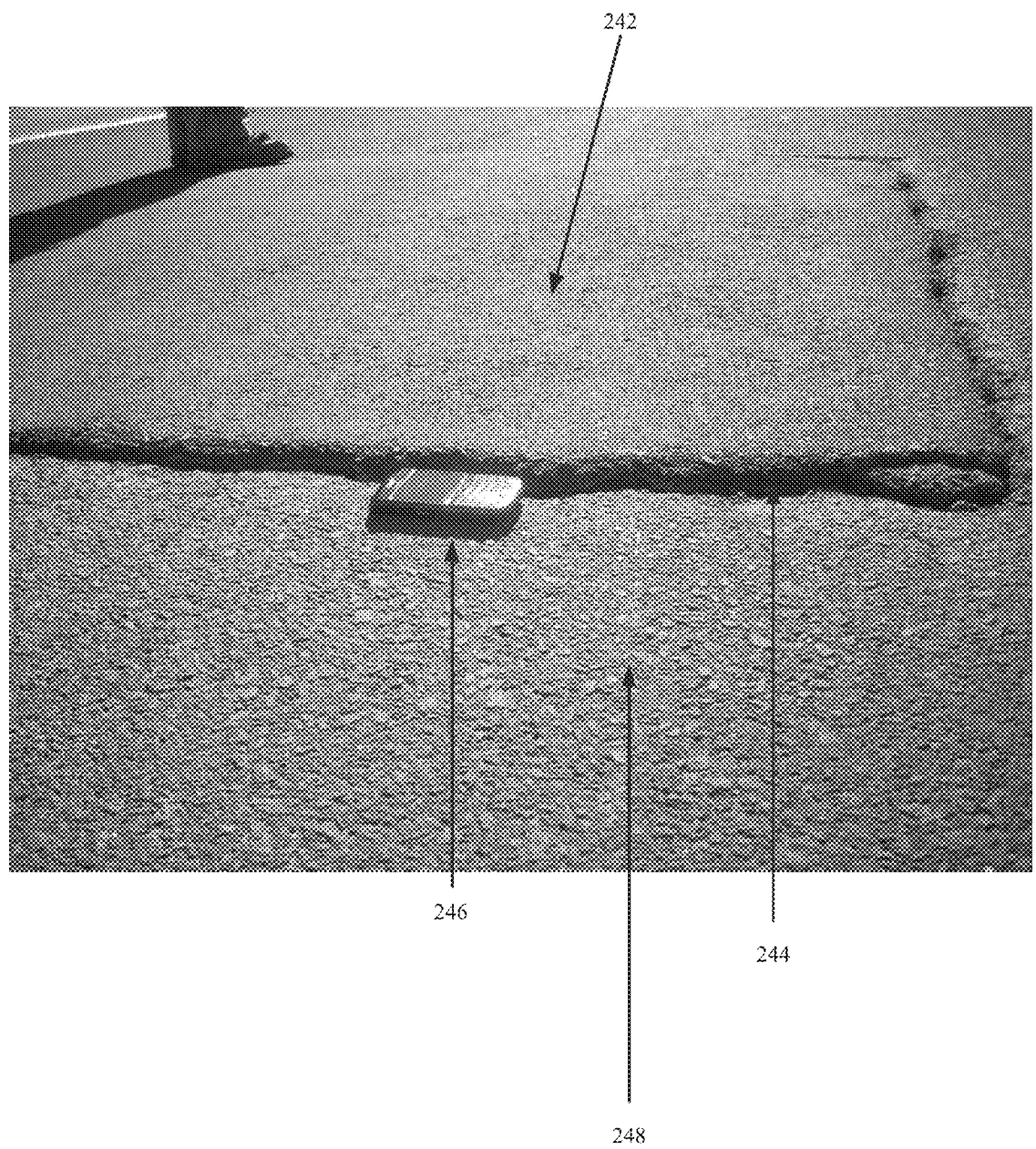
FIG. 18 is a pavement patch that has suffered frost heave due to the formation of ice lenses.

FIG. 18 is a picture of a road surface patch 242 over a backfill composition as taught by the '422 patent. As is evident from the picture, ice lens formation has caused frost heave 244 and the patch 242 rising above the surrounding pavement 248. A blackberry cellular phone 246 provides reference.

Annular Grout Compositions and Methods of Utilizing the Same

The present disclosure also provides compositions and methods for filling surface and subsurface voids with cellular, annular grout. Annular grout is historically a Portland cement composition for use in filling subterranean voids, i.e., areas around an underground pipe. Typically, access to the void is restricted, such that, the composition for filling the void must be pumped into the void without direct access to the entire void. For example, annular grout is typically used when replacing an older underground pipe with a new pipe by slip lining the old pipe with a new pipe. Following insertion of a new pipe into the old pipe, the void between the exterior wall of the new pipe and the interior wall of the old pipe is filled with an annular grout composition. In another example, annular grout is used to fill a subterranean void that either naturally occurred or was left from construction or depletion of well or mine. The annular grout is pumped into the subterranean void through an access port on the surface. In certain embodiments, annular grout is used fill the void left by removal of an underground pipe or to fill the old pipe itself. Annular grout can also be used to fill underground fuel tanks or backfill behind walls, buildings, or as embankment materials.

Compositions for use as an annular grout must have sufficient fluidity for pumping and subsequently filling voids without requiring any compaction. Compositions for use as annular grout must also have a delayed set time to allow the grout to flow the length or width of the void without setting. Compositions of the present disclosure exhibit sufficient fluidity for pumping, set-times for extended durations of installation, yet sufficiently high strengths at the required low densities.

For example, when filling the void left between a new pipe and old pipe by slip lining an old pipe, the composition of annular grout must maintain sufficient fluidity to travel the length of the pipe before setting. In some embodiments, sufficient density is necessary to displace ground water in the void.

In an embodiment of the present disclosure, a low density annular grout composition for filling voids comprises between 30%-85% air by volume; between 50%-90% cementitious fly ash by weight; between 10% and 45% water by weight; and between 0.01% and 2% set retarder by weight, wherein the composition has compressive strength of between 100 and 600 psi at seven days, a compressive strength of less than 1500 psi at 28 days, and a density of between 25 and 75 pcf.

The air content of the compositions of the present disclosure will vary depending on the desired properties of the composition. For example, the amount of air within the composition helps control the final density and strength of the annular grout. A lower ultimate strength can be limited with higher amounts of air content.

In some embodiments, the air content may be determined by the following formula using wet densities before and after the addition of air:

$$\text{Air content} = \frac{(\text{Unit Weight}_{no\ air} - \text{Unit Weight}_{air}) \times 100\%}{\text{Unit Weight}_{no\ air}}$$

In other embodiments, the air content can be determined using ASTM C231.

In certain embodiments, the air content is achieved by mixing an air entraining agent, i.e., a dry surfactant or liquid admixture into the cementitious fly ash and/or filler prior to addition of water. In these embodiments, the air content may by uniformly distributed by mixing directly in a truck or by mixing in a commonly used agitation/mixing device. The mixing process can occur prior to addition of water, after addition of water or simultaneously with the addition of water.

In another embodiment, the air content is achieved by addition of an air entraining agent after mixture of the dry ingredients (cementitious fly ash and possible filler) with water but prior to applying the composition to the void.

In specific embodiments, the air content may be achieved by adding a pre-formed cellular foam, e.g., GEOFOAM SNP foam liquid concentrate available from Cellular Concrete, LLC., 7020 Snowdrift Road, Suite 102, Allentown, Pa. 18106 or 5916 McIntyre St, Golden, Colo. 80403. The cellular foam may be pervious or non-pervious, and pre-foamed thereby reducing or alleviating the need to vigorously agitate the composition to activate the air entraining agent. Any suitable foaming agent may be used that achieves the desired end properties as described herein, e.g., an anionic foaming agent, a cationic foaming agent or a non-ionic foaming agent. An example of a pervious foam is GEOFOAM SP. An example of a non-pervious foam is GEOFOAM SNP. Suitable cellular foam is available from a variety of sources, e.g., Cellular Concrete, LLC; Provoton Foam Concrete, 28 East Larkspur Lane, Bristol, Ill. 60512; Allied Foam Tech Corp., 146 Keystone Dr. Montgomeryville, Pa. 18936; and Vermillion LLC and Associates, 2176 Sargent Daly Dr., Chattanooga, Tenn. 37421. The choice of an appropriate cellular foam is within one of skill in the art and may be dictated by cost, environmental concerns, or the need to meet the requirements of local or national agencies. In some embodiments, the foaming agent will conform to ASTM C869 and C796, in other embodiments the air entraining agent conforms to ASTM C260.

In some embodiments, the addition of cellular foam or similar air entraining agent may occur after the addition of water to the cementitious fly ash and/or filler immediately prior to the cementitious mixture leaving a mixing truck, as the cementitious mixture leaves the mixing truck (simultaneously) or after the cementitious mixture leaves the mixing truck.

The amount of air entraining agent necessary for a given composition will vary with the desired air content, e.g., the desired final compressive strength. In some embodiments, the final air content of the composition will be between about 35% and about 85%, between about 40% and about 80%, between about 45% and about 75%, between about 50% and about 70%, between about 50% and about 65%, between about 50% and about 75%, between about 35% and about 50%, between about 35% and about 60%, between about 50% and about 80%, between about 60% and 80%, between about 40% and about 50%, between about 40% and about 60%, or between about 35% and about 55%.

In some embodiments, the final air content will be greater than 20%, greater than 25%, greater than 30%, greater than 35%, greater than 40%, greater than 45%, greater than 50%, greater than 55%, greater than 60%, greater than 65%, greater than 70%, greater than 75%.

In other embodiments, the final air content of the composition will be less than 80%, less than 75%, less than 70%, less than 65%, less than 60%, less than 55%, less than 50%, less than 45%, less than 40%, less than 35%, or less than 30%.

In an embodiment of the present disclosure, the cementitious fly ash is Class C fly ash as defined by ASTM C618 or the standards of a local agency. In other embodiments of the present disclosure, the cementitious fly ash can have cementitious properties without qualifying as Class C fly ash under ASTM C618 or an equivalent standard. A cementitious fly ash of the present disclosure is a fly ash that sets (e.g., solidifies to 4 psi) within about thirty minutes at a water content of 30% by weight when water and cementitious fly ash are the only ingredients.

In an embodiment of the present disclosure, a composition has between about 50% and about 90% cementitious fly ash, between about 55% and about 85% cementitious fly ash, between about 60% and about 80% cementitious fly ash, between about 65% cementitious fly ash and about 75% cementitious fly ash, between about 50% and about 70% cementitious fly ash, and between about 50% and about 60% cementitious fly ash.

In some embodiments of the present disclosure, a composition has less than about 90% cementitious fly ash, less than about 85% cementitious fly ash, less than about 80% cementitious fly ash, less than about 75% cementitious fly ash, less than about 70% cementitious fly ash, less than about 65% cementitious fly ash, less than about 60% cementitious fly ash or less than about 55% cementitious fly ash. In additional embodiments of the present disclosure, the composition has greater than about 50% cementitious fly ash, greater than about 55% cementitious fly ash, cementitious fly ash, greater than about 60% cementitious fly ash, greater than about 65% cementitious fly ash, greater than about 70% cementitious fly ash, greater than about 75% cementitious fly ash, greater than about 80% cementitious fly ash, or greater than about 85% cementitious fly ash.

In an embodiment of the presently disclosed composition, the water is standard city potable water. In another embodiment, the water used in the composition is substantially purified of additional minerals or other impurities. In still another embodiment of the present disclosure, the water is non-potable water. In additional embodiments, the water is selected based on its natural impurities, i.e., specific mineral content like calcium, magnesium, iron, or similar water minerals.

The water content of the presently disclosed composition may vary depending on desired flowability, setting time and final compressive strength. It is advantageous for the flowability of an annular grout composition to allow efficient pumping and be capable of traveling the distance of the void, e.g., pipe. In an embodiment of the present disclosure, a composition has a the water content of between about 10% and about 45%, between about 15% and about 35%, between about 20% and about 30%, between about 10% and about 30%, between about 10% and about 25%, between about 20% and about 45%. In additional embodiments, a composition has greater than about 10% water, greater than about 20% water, greater than about 30% water, greater than about 40% water, or greater than about 50% water. In other embodiments, a composition has less than about 55% water, less than about 45% water, less than about 35% water, less than about 25% water, less than about 20% water, less than about 15% water, or less than about 10% water. Any water included with additional ingredients, e.g., aqueous water retarders, foaming agents, etc. under the circumstances encountered in the field by the inventors has been negligible in comparison to the primary batch water and therefore has not been included in the above calculations. Depending on the actual water content of the additional ingredients used it may be necessary to consider the additional water in the final water concentrations.

In some embodiments of the present disclosure, a composition will include at least one filler. In additional embodiments, a composition will include only one filler, while in other embodiments, a composition will contain only two fillers. In still additional embodiments, a composition will contain less than 3 fillers or less than 4 fillers. A filler in the present disclosure can be additional fly ash, e.g., Type F fly ash as determined by ASTM C618 or equivalent standard. A filler can also be non-specification grade non-cementitious fly ash, e.g., a fly ash that does not meet the specifications determined by ASTM C618. In certain embodiments a filler can be sand, bottom ash, quarry fines, soil, gravel and Portland cement, aggregate, or recycled version thereof. Determination of the filler material can be based on economics, availability, city, county and/or state specifications, or on the desired properties of the composition, e.g., desired setting time, flowability, or final compressive strength.

In an embodiment, a composition of the present disclosure will have between about 1% and about 40% filler, between about 5% and about 35% filler, between about 10% and about 30% filler, between about 15% and about 25% filler, between about 1% and about 20%, between about 5% and about 20%, between about 5% and about 15%, between about 30% and about 40%. In certain embodiments, a composition of the present disclosure will have less than about 50% filler, less than about 70% filler, less than about 60% filler, less than about 50% filler, less than about 40% filler, less than about 35% filler, less than about 30% filler, less than about 25% filler, less than about 20% filler, less than about 15% filler, less than about 10% filler, less than about 5% filler or less than about 3% filler. In still other embodiments, a composition of the present disclosure will have greater than about 10% filler, greater than about 15% filler, greater than about 20% filler, greater than about 25% filler, greater than about 30% filler, greater than about 35% filler, or greater than about 40% filler.

Annular grout compositions will comprise a set retarder in some embodiments. A set retarder is a compound capable of delaying the set time of the composition. In certain embodiments, delaying the set time is necessary to allow an annular grout to completely fill a void before setting, e.g., to travel the length of a pipe from composition insertion point to a determined end point. An example of a set retarder may be citric acid or borax, or a combination thereof. In certain embodiments, the set retarder is liquid while in other embodiments the set retarder is a powder. An appropriate set retarder will be well known to a person of ordinary skill in the art.

In an embodiment, the concentration of set retarder is between about 0.01% and about 3%, between about 0.01% and about 2% between about 0.05% and about 2.5%, between about 0.1% and about 2%, between about 0.5% and about 1.5%, between about 0.0001% and about 1.0%. In some embodiments, the set retarder is greater than about 0.001%, is greater than about 0.01% is greater than about 0.05%, is greater than about 0.1%, is greater than about 0.5%, is greater than about 1.0%, is greater than about 1.5%, or is greater than about 2.0%. In certain embodiments, the set retarder is less than about 3.0%, less than about 2.5%, less than about 2.0%, less than about 1.5%, less than about 1.0%, less than about 0.5%, less than about 0.3%, less than about 0.1%, less than about 0.01%, less than about 0.001%.

In some embodiments, the composition may further comprise a water reducer. Water reducers may be used when a higher final strength is desired at a specified density and fluidity. In some embodiments the water reducer will be powder while in other embodiments it will be a liquid water reducer. In an embodiment, the water reducer is CHRYSO 256 (high range) or 380 (midrange) or similar composition suitable for use in the disclosed composition. A water reducer is a chemical (e.g., chemical composition) that allows a mixture to maintain the same fluidity with less water or more fluidity with the same amount of water.

In an embodiment, the concentration of the water reducer is between about 0.01% and about 3%, between about 0.01% and about 2% between about 0.05% and about 2.5%, between about 0.1% and about 2%, between about 0.5% and about 1.5%, between about 0.0001% and about 1.0%. In some embodiments, the water reducer is greater than about 0.001%, is greater than about 0.01% is greater than about 0.05%, is greater than about 0.1%, is greater than about 0.5%, is greater than about 1.0%, is greater than about 1.5%, or is greater than about 2.0%. In certain embodiments, the water reducer is less than about 3.0%, less than about 2.5%, less than about 2.0%, less than about 1.5%, less than about 1.0%, less than about 0.5%, less than about 0.3%, less than about 0.1%, less than about 0.01%, less than about 0.001%.

Compositions of the present disclosure will have a range of possible set times based on the desired application. For example, the longer the pipe or the slower the pump rate, the longer the set time necessary to complete filling the pipe before the composition sets. In some embodiments, the set time of the composition is determined by measuring penetration resistance with a pocket penetrometer (e.g., with a static resistance of 4 psi as used in standard ASTM WK 27337) or cement setting time standard ASTM C403. In an embodiment of the present disclosure, the set time for a composition can be between about 60 minutes and about 8 hours, between about 2 hours and about 7 hours, between about 3 hours and about 6 hours. In additional embodiments, a composition has a set time of less than 10 hours, of less than about 9 hours, of less than about 8 hours, of less than about 7 hours, of less than about 6 hours, of less than about 5 hours, of less than about 4 hours, of less than about 3 hours, of less than about 2 hours or of less than about 1 hour. In other embodiments, a composition has a set time of greater than about 2 hours, of greater than about 3 hours, of greater than about 4 hours, of greater than about 5 hours, of greater than about 6 hours, of greater than about 7 hours, of greater than about 8 hours, or of greater than about 9 hours.

Compositions of the present disclosure will have a range of compressive strengths at various times after the addition of a composition to a void depending on the desired properties of the composition.

In certain embodiments, the compressive strength is measured at 1 day, 3 days, 7 days and 28 days where the 28 day measurement is considered the final compressive strength. In other embodiments, the compressive strength is measured more often at smaller intervals or less often at larger intervals. In some embodiments, the compressive strength is measured at 90 days. In an embodiment, the bearing penetration or capacity resistance of a composition is measured at 1 day, 3 days, 7 days and 28 days using ASTM WK 27337 or C403.

In an embodiment, the compressive strength (e.g., tested by ASTM C495) of a composition of the present disclosure at seven days will be between about 100 psi and about 600 psi, 150 psi and about 550 psi, between about 200 psi and about 500 psi, between about 250 psi and about 450 psi, between about 100 psi and about 500 psi, between about 100 psi and about 400 psi, between about 100 psi and about 300 psi, between about 300 psi and about 600 psi. In additional embodiments, the compressive strength of the composition at seven days will be greater than about 100 psi, will be greater than about 150 psi, will be greater than about 200 psi, will be greater than about 250 psi, will be greater than about 300 psi, will be greater than about 350 psi, will be greater than about 400 psi or will be greater than about 500 psi. In an embodiment, the compressive strength of a composition of the present disclosure at seven days will be less than about 600 psi, less than about 500 psi, less than about 450 psi, less than about 400 psi, less than about 350 psi, less than about 300 psi, less than about 250 psi, or less than about 200 psi.

In an embodiment, the compressive strength of a composition of the present disclosure at 28 days will be between about 200 psi and about 500 psi, between about 200 psi and about 600 psi, between about 200 psi and about 1500 psi, between about 300 psi and about 1300 psi, between about 300 psi and about 1100 psi, between about 300 psi and about 900 psi, between about 300 psi and about 700 psi. In additional embodiments, the compressive strength of the composition at 28 days will be greater than about 200 psi, will be greater than about 300 psi, will be greater than about 400 psi, will be greater than about 500 psi, will be greater than about 600 psi, will be greater than about 700 psi, or will be greater than about 800 psi. In certain embodiments, the compressive strength of the composition at 28 days will be less than about 1500 psi, less than about 1250 psi, less than about 1000 psi, less than about 800 psi, less than about 700 psi, less than about 600 psi, or less than about 500 psi.

In certain embodiments of the present disclosure, a suitable composition can be defined by the water to fly ash ratio, e.g., when using no filler, when using non-cementitious fly ash filler, or other suitable filler like sand. The water to fly ash ratio will be a water to cementitious fly ash plus additional non-cementitious fly ash filler ratio.

In certain embodiments, a composition can have a range of water to fly ash ratios depending on the water demand of the fly ash (or included filler), the desired flowability, the desired setting time and the desired final compressive strength. In certain embodiments, the water to fly ash ratio of a composition (W/FA) is between about 0.15 and about 0.25, between about 0.2 and about 0.6, between about 0.2 and about 0.5, between about 0.2 and about 0.4 or between about 0.25 and about 0.35. In additional embodiments, the water to fly ash ratio of a composition is greater than about 0.2, greater than about 0.25, greater than about 0.3, greater than about 0.35 or greater than about 0.4. In other embodiments, the water to fly ash ratio is less than about 0.6, less than about 0.5, less than about 0.4, less than about 0.35, less than about 0.3, less than about 0.25 or less than about 0.2.

In certain embodiments of the present disclosure, an annular grout composition does not include one or more of the following: does not include a water reducer, does not include Portland cement, does not include a set retarder, does not include any cementitious material other than cementitious fly ash, does not include a filler, does not include aggregate, does not include gravel, does not include $CaCO_3$ or lime other than that present in the cementitious fly ash and/or filler, or does not include sand. Furthermore, a composition of the present disclosure does not include native soils in some embodiments.

In certain embodiments, the flowability of a composition can be determined by a slump test C143 or a slump flow as determined by C1611 or spread as determined by D6103.

The density in an annular grout composition is important in certain embodiments. For example, when filling the void left between pipes in a slip-lined pipe, the density is often limited to a specified maximum density to prevent or limit the composition from floating the pipe being grouted (e.g., preventing the new internal pipe from floating on top of the composition thereby causing the top surface of the internal pipe to contact the top surface side of the old external pipe). In other cases, the density greater is than water to displace residual water in the void.

In embodiments, a composition of the present disclosure has a unit weight of between about 25 pcf and about 75 pcf, of between about 30 pcf and about 70 pcf, between about 35 pcf and about 65 pcf, between about 40 pcf and about 60 pcf, between about 45 pcf and about 55 pcf, between about 25 and 55 pcf, between about 35 and 55 pcf, between about 45 pcf and 65 pcf or between about 45 pcf and 60 pcf. In other embodiments, the unit weight of a composition is greater than about 30 pcf, greater than about 35 pcf, greater than about 40 pcf, greater than about 45 pcf, greater than about 50 pcf, greater than about 55 pcf, or greater than about 60 pcf. In still other embodiments, a composition has a unit weight of less than about 70 pcf, of less than about 65 pcf, of less than about 60 pcf, of less than about 55 pcf, of less than about 50 pcf, of less than about 45 pcf, of less than about 40 pcf or of less than about 35 pcf.

The present disclosure also contemplates a method of determining a low density annular grout composition for filling a subterranean void comprising: identifying at least one fly ash for use in the composition; determining a water demand of each fly ash within the composition; calculating a water demand for the composition; determining a compressive strength for the composition; determining the amount of air content necessary for the composition to have a compressive strength of between 200 and 600 psi at seven days, a compressive strength of less than 1500 psi at 28 days, and a density of between 25 and 75 pcf; determining the time necessary to fill the void; and determining the concentration of set retarder necessary to delay the composition from setting in less time than necessary to fill the void.

The determination of suitable fly ash, water demand, compressive strength, air content, density can be accomplished as discussed elsewhere in this application. Determining the time necessary to fill any given void will can be a function of the length of the void, the volume of the void, the flowability of the composition, and the pump rate of the composition. Additional factors can include the time necessary to mix an additional volume of composition or to switch mixing trucks, or cleaning pumps and hoses after pumping the composition into the void. Determining the concentration of set retarder necessary to delay the composition from setting too soon can include accounting for the retarder type, the final density of the composition, the cementitious fly ash content, the water to cementitious fly ash ratio or any other factor influencing the activity of the set retarder.

The present disclosure also contemplates a method of filling a void with a low density annular grout composition comprising: determining the time necessary to fill the void; adding water and set retarder to a cementitious fly ash to make a wet mixture; adding air to the wet mixture, wherein the composition has a compressive strength of between 100 and 600 psi at seven days, a compressive strength of less than 1500 psi at 28 days, and a density of between 20 and 75 pcf; and adding the composition to the void.

Referring now to FIG. 19 which represents the compressive strength testing versus air content for a composition having a 0.25 water to fly ash ratio. The compressive strength versus air content is shown at one day 304, at seven days 302, and at twenty eight days 300.

One of the challenges to designing these compositions is achieving the desired minimum compressive strength, at the desired density, given the amount of time required to test for strength and the numerous combinations of two fly ashes, at different water contents, and the ability of a water reducer to increase strength. A mix design aid has been developed to expedite the process of determining a suitable combination of materials.

With a given cementitious fly ash, first mix it at a water to fly ash ratio of 0.25, which typically gives sufficient fluidity to mix varying amounts of cellular foam into. This is considered the baseline slurry mixtures (e.g., FIG. 19). Next determine the fluid density at the time of mixing, then fabricate penetration resistance and compressive strength specimens to test at varying ages; typically 4 hours, 24 hours, 3 days, 7 days, and 28 days.

With this baseline slurry mixture, add increasing amounts of foam to achieve various air contents: approximately 10%, 20%, 30%. 40%, 50%, 60%, 70% and 80% would be suggested, however 20%, 40%, 60% and 80% could be used to expedite the process. Once penetration resistance and compressive testing is complete for each of these foamed mixtures, the test results can be plotted on a psi versus air content graph for each age of testing, e.g., FIG. 19.

Next different slurry combinations can be tested for strength & penetration resistance at the corresponding ages, but without adding any cellular foam. For higher strengths at a given density, a water-reducer would be used at different dosages to maintain fluidity for mixing foam and pumping, yet achieve lower water to fly ash ratios for those higher strengths. Conversely, if less strength is needed than given by the baseline mixture at varying air contents & densities, higher W/FA ratios and/or varying amounts of filler (fly ash) can be used for improved economy of the desired mixture. Next, determine the fluid density of each additional non-foamed slurry, and fabricate strength specimens as described in the proceeding sections.

In an embodiment, since the inherent strength of any given composition is a function of the base slurry strength and the amount of air content, this mix design aid can be used to estimate results from a given set of proportions by following the following protocol.

First, for a given (non-baseline) slurry mixture, calculate the air content that will achieve the desired density, based on the measured non-foamed density, e.g., using the formula previously disclosed in this disclosure.

Second, enter the strength versus air content curves for the given age of testing for the baseline mixture to determine the inherent strength at that particular age and air content. For example, the 28 day strength of the baseline mixture at 48% is 700 psi, e.g., 306 in FIG. 19.

Finally, compare the relative strengths of the non-foamed slurry of interest to the non-foamed baseline mixture at the same age. In this case, the baseline slurry yielded 6000 psi at 28 days at 0% air content, e.g., 300 in FIG. 19, versus 4500 psi for the other slurry at 0% air, e.g., 302 in FIG. 19. Estimate the final strength of the other slurry at a given air content & age, by multiplying the result from step 2 by the ratio of the non-foamed results (700×4500/6000), calculated as 525 psi (e.g., FIG. 19).

Therefore, an embodiment of the present disclosure includes a method of formulating an annular grout composition, comprising mixing a first baseline mixture of a cementitious fly ash with water to about a 0.25 water to fly ash ratio, wherein the first baseline mixture is divided into at least three sub-mixtures including one sub-mixture with no added air content and two sub-mixtures with different air contents; measuring fluid density, penetration resistance and compressive strength of the sub-mixtures for at least two different times post mixing; mixing a second mixture of at least one cementitious fly ash with water with no additional air content; measuring fluid density, penetration resistance and compressive strength of the second mixture for at least two different time post mixing; calculating air content necessary to achieve a specific density for a third mixture of cementitious fly ash with water; and calculating a compressive strength for the third mixture at a specific age and air content using data from the first baseline mixture and the second mixture.

In some embodiments, a filler of non-cementitious fly ash, or any previously discussed filler or suitable filler, e.g., water reducers, set retarders, etc., may be included in the mixtures. In embodiments, the first baseline mixture may be mixed prior to dividing into sub-mixtures (e.g., for addition of air) or each first baseline sub-mixture may be mixed independently of each other. In an embodiment, the first baseline mixture may be mixed to a water to fly ash ratio between about 0.20 and about 0.30, to between about 0.22 and about 0.28, to between about 0.23 and about 0.26. In some embodiments, the water to fly ash ratio is mixed to less than 0.29, less than 0.28, to less than 0.27, to less than 0.26, to less than 0.25, to less than 0.24, to less than 0.23. In some embodiments, the water to fly ash ratio is mixed to greater than 0.21, greater than 0.22, to greater than 0.23, to greater than 0.24, to greater than 0.25, to greater than 0.26.

Compositions for Caisson Construction and Methods of Utilizing the Same

The present disclosure also discloses a high-performance composition, generating high strengths, suitable for replacement of traditional concrete in specific applications of building construction. In an embodiment, the use of chemical retarders, and potentially water-reducers admixtures will accomplish structural requirements for this improved composition. In some embodiments, traditional and non-traditional aggregates might be used in the mixture matrix to reduce shrinkage and material costs.

Traditional Portland-cement based concrete for drilled-pier and caisson construction for building foundations is typically specified to have a design strength of 3000-4000 psi in 28 days. Since freeze-thaw protection is generally not required, the traditional concrete is typically not air-entrained and high slumps (5-8" or greater) are required to ensure proper consolidation, since internal vibration is not possible at the greater depths of the caissons.

One composition of the present disclosure creates a cost-effective alternative to traditional concrete for caisson construction by using fly ash. The use of fly ash as alternative to Portland-based cement allows on-site batching with volumetric mixing trucks and eliminates a lot of challenges of caisson construction with traditional concrete delivered in mixer-trucks. Caisson construction generally refers to the use of deep foundation support that is constructed by placing fresh concrete and reinforcing steel into a drilled shaft. Caissons, which are capable of supporting high, concentrated loads, are typically used to set piers for bridges, underpasses, structural supports, as well as in slide prevention applications.

Mixtures can be designed by first testing a caisson composition at various water contents, to determine early and long-term strengths, as a function of fluidity required for normal caisson construction. Various dosages of set retarder and water retarders can be tested to determine the concentration required for reasonable constructability in the field, i.e., reasonably set time. In addition, in some embodiments an aggregate may be included in the caisson composition.

After arriving at a desired composition, the incorporation of varying air contents can be tested accounting for water/fly ash ratios to reach a required strength and fluidity for placement.

One of the benefits of the presently disclosed caisson composition when coupled with on-site mixing trucks is that the exact amount of material to fill a caisson is on-site, ready to be mixed & placed when drilling operations require it. Worries about ready-mixed concrete being stuck in traffic or being on-site too long, resulting in rejection of the concrete batch are eliminated.

For small projects, and not requiring a concrete-pump truck to place material in high-groundwater conditions, these volumetric trucks can readily be driven to discharge directly into each caisson hole. Alternately, they could remain parked by the concrete-pump truck, discharging into the receiving hopper as numerous concrete trucks would normally do.

Other significant benefits of the presently disclosed caisson composition is that the mixing truck and concrete pump truck can be parked in an out of the way location; continuous supplies of water and fly ash can be provided by a nearby fire hydrant and one or more bulk fly ash tankers. On secure sites;

the mixing-truck can remain on-site for several days, with only the replenishing of fly ash materials in the bulk storage required.

Another significant benefit of the presently disclosed caisson composition is the reduction is shrinkage that occurs during (e.g., chemical) and after (e.g., drying) hardening. For example, a Portland-cement paste has a chemical shrinkage of between 1% and 2%. By contrast, a cementitious fly ash paste of the present disclosure has a chemical shrinkage of between 0.03% and 0.05% or less. For example, Portland-cement concrete has a drying shrinkage of between 0.04% and 0.06% after 28 days. By contrast, a cementitious fly ash composition of the present disclosure has a drying shrinkage of between 0.001% and 0.002% or less. Normal methods to reduce shrinkage include using more rock or larger size rock in a traditional concrete composition and using a low water to traditional cement ratio. Surprisingly, the caisson composition of the present disclosure reduced shrinkage as compared with traditional concrete without using traditional methods to reduce shrinkage.

In an embodiment, a composition for caisson construction comprises between 0.0001% and 10% air by volume; between 60%-95% cementitious fly ash by weight; between 5%-30% water by weight; and between 0.01% and 2% set retarder by weight, wherein the composition has compressive strength of between 3000 and 5000 psi at seven days, a compressive strength of between 4000 and 8000 psi at 28 days, and a density of between 100 and 150 pcf.

The air content of the compositions of the present disclosure will vary depending on the desired properties of the composition. In some embodiments, the presently disclosed caisson composition can include a cellular foam to produce a high-strength material capable of freeze-thaw resistance for external applications and/or to significantly lower the unit weight of the composition, making it suitable as a substitute for traditional lightweight concrete for interior, elevated floor slabs. In this configuration, the lightweight, foamed high-strength composition would provide lower dead-loads in building, increased fire-resistance, increased insulation-value, and sound-proofing if used as walls between dwelling units.

In some embodiments, the air content may be determined by the following formula using wet densities before and after the addition of air:

$$\text{Air content} = \frac{(\text{Unit Weight}_{no\ air} - \text{Unit Weight}_{air}) \times 100\%}{\text{Unit Weight}_{no\ air}}$$

In other embodiments, the air content can be determined using ASTM C231.

In certain embodiments, the air content is achieved by mixing an air entraining agent, i.e., a dry surfactant or liquid admixture into the cementitious fly ash and/or filler prior to addition of water. In these embodiments, the air content may by uniformly distributed by mixing directly in a truck or by mixing in a commonly used agitation/mixing device. The mixing process can occur prior to addition of water, after addition of water or simultaneously with the addition of water.

In another embodiment, the air content is achieved by addition of an air entraining agent after mixture of the dry ingredients (cementitious fly ash and possible filler) with water but prior to applying the composition to the void.

In specific embodiments, the air content may be achieved by adding a pre-formed cellular foam, e.g., GEOFOAM SNP foam liquid concentrate available from Cellular Concrete, LLC., 7020 Snowdrift Road, Suite 102, Allentown, Pa. 18106 or 5916 McIntyre St, Golden, Colo. 80403. The cellular foam may be pervious or non-pervious, and pre-foamed thereby reducing or alleviating the need to vigorously agitate the composition to activate the air entraining agent. Any suitable foaming agent may be used that achieves the desired end properties as described herein, e.g., an anionic foaming agent, a cationic foaming agent or a non-ionic foaming agent. An example of a pervious foam is GEOFOAM SP. An example of a non-pervious foam is GEOFOAM SNP. Suitable cellular foam is available from a variety of sources, e.g., Cellular Concrete, LLC; Provoton Foam Concrete, 28 East Larkspur Lane, Bristol, Ill. 60512; Allied Foam Tech Corp., 146 Keystone Dr. Montgomeryville, Pa. 18936; and Vermillion LLC and Associates, 2176 Sargent Daly Dr., Chattanooga, Tenn. 37421. The choice of an appropriate cellular foam is within one of skill in the art and may be dictated by cost, environmental concerns, or the need to meet the requirements of local or national agencies. In some embodiments, the foaming agent will conform to ASTM C869 and C796, in other embodiments the air entraining agent conforms to ASTM C260.

In some embodiments, the addition of cellular foam or similar air entraining agent may occur after the addition of water to the cementitious fly ash and/or filler immediately prior to the cementitious mixture leaving a mixing truck, as the cementitious mixture leaves the mixing truck (simultaneously) or after the cementitious mixture leaves the mixing truck.

The amount of air entraining agent necessary for a given composition will vary with the desired air content. In some embodiments, the final air content of the composition will be between about 0.001% and about 15%, between about 0.01% and about 13%, between about 0.1% and about 10%, between about 1.0% and about 8%, between about 2% and about 6%, between about 0.1% and about 5%, between about 0.1% and about 2%, between about 4% and about 10%, between about 4% and about 8%. In some embodiments, the composition does not contain any additional air content, i.e., the composition is not purposefully air entrained.

In some embodiments, the final air content will be greater than 0.1%, greater than 1%, greater than 2%, greater than 4%, greater than 6%, greater than 8%, greater than 10%, greater than 12%.

In other embodiments, the final air content of the composition will be less than 15%, less than 13%, less than 10%, less than 8%, less than 6%, less than 4%, less than 2%, less than 1%, less than 0.1%, less than 0.01%.

In an embodiment of the presently disclosure caisson composition, the cementitious fly ash is Class C fly ash as defined by ASTM C618 or the standards of a local agency. In other embodiments of the present disclosure, the cementitious fly ash can have cementitious properties without qualifying as Class C fly ash under ASTM C618 or an equivalent standard. A cementitious fly ash of the present disclosure is a fly ash that sets (e.g., solidifies to 4 psi) within about thirty minutes at a water content of 30% by weight when water and cementitious fly ash are the only ingredients.

In an embodiment of the present disclosure, a composition has between about 60% and about 95% cementitious fly ash, between about 65% and about 90% cementitious fly ash, between about 65% and about 85% cementitious fly ash, between about 70% cementitious fly ash and about 80% cementitious fly ash, between about 60% and about 80% cementitious fly ash, and between about 70% and about 90% cementitious fly ash.

In some embodiments of the present disclosure, a composition has less than about 95% cementitious fly ash, less than about 90% cementitious fly ash, less than about 85% cementitious fly ash, less than about 80% cementitious fly ash, less than about 75% cementitious fly ash, less than about 70% cementitious fly ash, less than about 65% cementitious fly ash or less than about 60% cementitious fly ash. In additional embodiments of the present disclosure, the composition has greater than about 60% cementitious fly ash, greater than about 65% cementitious fly ash, cementitious fly ash, greater than about 70% cementitious fly ash, greater than about 75% cementitious fly ash, greater than about 80% cementitious fly ash, greater than about 85% cementitious fly ash, greater than about 90% cementitious fly ash, or greater than about 95% cementitious fly ash.

In an embodiment of the presently disclosed composition, the water is standard city potable water. In another embodiment, the water used in the composition is substantially purified of additional minerals or other impurities. In still another embodiment of the present disclosure, the water is non-potable water. In additional embodiments, the water is selected based on its natural impurities, i.e., specific mineral content like calcium, magnesium, iron, or similar water minerals.

The water content of the presently disclosed composition may vary depending on desired flowability, setting time and final compressive strength. In an embodiment of the present disclosure, a composition has a the water content of between about 5% and about 30%, between about 10% and about 25%, between about 15% and about 20%, between about 5% and about 15%, between about 5% and about 20%, between about 15% and about 25%. In additional embodiments, a composition has greater than about 5% water, greater than about 10% water, greater than about 15% water, greater than about 20% water, or greater than about 25% water. In other embodiments, a composition has less than about 30% water, less than about 25% water, less than about 20% water, less than about 18% water, less than about 15% water, less than about 10% water, or less than about 22% water. Any water included with additional ingredients, e.g., aqueous water retarders, foaming agents, etc. under the circumstances encountered in the field by the inventors has been negligible in comparison to the primary batch water and therefore has not been included in the above calculations. Depending on the actual water content of the additional ingredients used it may be necessary to consider the additional water in the final water concentrations.

In some embodiments of the present disclosure, a composition will include at least one filler. In additional embodiments, a composition will include only one filler, while in other embodiments, a composition will contain only two fillers. In still additional embodiments, a composition will contain less than 3 fillers or less than 4 fillers. A filler in the present disclosure can be additional fly ash, e.g., type F fly ash as determined by ASTM C618 or equivalent standard. A filler can also be non-specification grade non-cementitious fly ash, e.g., a fly ash that does not meet the specifications determined by ASTM C618. In certain embodiments a filler can be sand, bottom ash, quarry fines, soil, gravel and Portland cement, aggregate, or recycled version thereof. Determination of the filler material can be based on economics, availability, city, county and/or state specifications, or on the desired properties of the composition, e.g., desired setting time, flowability, or final compressive strength.

In an embodiment, a composition of the present disclosure will have between about 1% and about 25% filler, between about 5% and about 20% filler, between about 10% and about 15% filler, between about 1% and about 10% filler, between about 1% and about 5%, between about 5% and about 10%, between about 5% and about 15%, between about 10% and about 20%. In certain embodiments, a composition of the present disclosure will have less than about 25% filler, less than about 20% filler, less than about 15% filler, less than about 10% filler, less than about 5% filler, less than about 1% filler. In still other embodiments, a composition of the present disclosure will have greater than about 1% filler, greater than about 5% filler, greater than about 10% filler, greater than about 15% filler, greater than about 20% filler, greater than about 25% filler, or greater than about 8% filler.

Caisson compositions will comprise a set retarder in most embodiments. A set retarder is a compound capable of delaying the set time of the composition. In certain embodiments, delaying the set time is necessary to allow a caisson composition to completely fill a caisson before setting and keeping the mixture fluid in the pump between fillings. An example of a set retarder may be citric acid or borax, or a combination thereof. In certain embodiments, the set retarder is liquid while in other embodiments the set retarder is a powder. An appropriate set retarder will be well known to a person of ordinary skill in the art.

In an embodiment, the concentration of set retarder is between about 0.01% and about 3%, between about 0.01% and about 2% between about 0.05% and about 2.5%, between about 0.1% and about 2%, between about 0.5% and about 1.5%, between about 0.0001% and about 1.0%. In some embodiments, the set retarder is greater than about 0.001%, is greater than about 0.01% is greater than about 0.05%, is greater than about 0.1%, is greater than about 0.5%, is greater than about 1.0%, is greater than about 1.5%, or is greater than about 2.0%. In certain embodiments, the set retarder is less than about 3.0%, less than about 2.5%, less than about 2.0%, less than about 1.5%, less than about 1.0%, less than about 0.5%, less than about 0.3%, less than about 0.1%, less than about 0.01%, less than about 0.001%.

In some embodiments, the composition may further comprise a water reducer. Water reducers may be used when a higher final strength is desired at a specified density and fluidity. In some embodiments the water reducer will be powder while in other embodiments it will be a liquid water reducer. In an embodiment, the water reducer is CHRYSO 256 (high range) or 380 (midrange) or similar composition (CHRYSO, Inc., 1611 State Hwy 276, Rockwall, Tex. 75032). A water reducer is a chemical (e.g., chemical composition) that allows a mixture to maintain the same fluidity with less water or more fluidity with the same amount of water.

In an embodiment, the concentration of the water reducer is between about 0.01% and about 3%, between about 0.01% and about 2% between about 0.05% and about 2.5%, between about 0.1% and about 2%, between about 0.5% and about 1.5%, between about 0.0001% and about 1.0%. In some embodiments, the water reducer is greater than about 0.001%, is greater than about 0.01% is greater than about 0.05%, is greater than about 0.1%, is greater than about 0.5%, is greater than about 1.0%, is greater than about 1.5%, or is greater than about 2.0%. In certain embodiments, the water reducer is less than about 3.0%, less than about 2.5%, less than about 2.0%, less than about 1.5%, less than about 1.0%, less than about 0.5%, less than about 0.3%, less than about 0.1%, less than about 0.01%, less than about 0.001%.

Compositions of the present disclosure will have a range of possible set times based on the desired application. For example, the larger the caisson or the slower the pump rate, the longer the set time necessary to complete filling the caisson before the composition sets. In some embodiments, the set time of the caisson composition is determined by measuring penetration resistance with a pocket penetrometer (e.g., with a resistance of 4 psi as typically used in standard ASTM WK 27337) or cement setting time standard ASTM C403. In an embodiment of the present disclosure, the set time for a composition can be between about 60 minutes and about 8 hours, between about 2 hours and about 7 hours, between about 3 hours and about 6 hours. In additional embodiments, a composition has a set time of less than 10 hours, of less than about 9 hours, of less than about 8 hours, of less than about 7 hours, of less than about 6 hours, of less than about 5 hours, of less than about 4 hours, of less than about 3 hours, of less than about 2 hours or of less than about 1 hour. In other embodiments, a composition has a set time of greater than about 2 hours, of greater than about 3 hours, of greater than about 4 hours, of greater than about 5 hours, of greater than about 6 hours, of greater than about 7 hours, of greater than about 8 hours, or of greater than about 9 hours.

Caisson compositions of the present disclosure will have a range of compressive strengths at various times after the addition of a composition to a caisson void depending on the desired properties of the composition.

In certain embodiments, the compressive strength is measured at 1 day, 3 days, 7 days and 28 days where the 28 day measurement is considered the final compressive strength. In other embodiments, the compressive strength is measured more often at smaller intervals or less often at larger intervals. In some embodiments, the compressive strength is measured at 90 days.

In an embodiment, the compressive strength (e.g., tested by ASTM C31) of a caisson composition of the present disclosure at seven days will be between about 3000 psi and about 6000 psi, between 3000 psi and 5000 psi, between about 3500 psi and about 5500 psi, between about 4000 psi and about 5000 psi, between about 3500 psi and about 5000 psi, between about 4000 psi and about 6000 psi, between about 3000 psi and about 4000 psi. In additional embodiments, the compressive strength of the caisson composition at seven days will be greater than about 2500 psi, will be greater than about 3000 psi, will be greater than about 3500 psi, will be greater than about 4500 psi, will be greater than about 5000 psi, will be greater than about 5500 psi, will be greater than about 6000 psi. In an embodiment, the compressive strength of a caisson composition of the present disclosure at seven days will be less than about 7000 psi, less than about 6500 psi, less than about 6000 psi, less than about 5500 psi, less than about 5000 psi, less than about 4500 psi, less than about 4000 psi, less than 3000 psi, or less than about 8000 psi.

In an embodiment, the compressive strength of a caisson composition of the present disclosure at 28 days will be between about 4000 psi and about 8000 psi, between about 5000 psi and about 7000 psi, between about 7000 psi and about 8000 psi, between about 7000 psi and about 10000 psi, between about 9000 psi and about 11000 psi, between about 5000 psi and about 8000 psi, between about 5000 psi and about 7000 psi. In additional embodiments, the compressive strength of the caisson composition at 28 days will be greater than about 4500 psi, will be greater than about 5000 psi, will be greater than about 6000 psi, will be greater than about 7000 psi, will be greater than about 8000 psi, will be greater than about 9000 psi, or will be greater than about 10000 psi. In certain embodiments, the compressive strength of the caisson composition at 28 days will be less than about 11000 psi, less than about 10000 psi, less than about 9000 psi, less than about 8000 psi, less than about 7000 psi, less than about 6000 psi, less than about 5000 psi, or less than about 4500 psi.

In certain embodiments of the present disclosure, a suitable caisson composition can be defined by the water to fly ash ratio, e.g., when using no filler, when using non-cementitious fly ash filler, or other suitable filler like sand. In certain embodiments, the water to fly ash ratio will be a water to cementitious fly ash plus additional non-cementitious fly ash filler ratio.

In certain embodiments, a composition can have a range of water to fly ash ratios depending on the water demand of the fly ash (or included filler), the desired flowability, the desired setting time and the desired final compressive strength. In certain embodiments, the water to fly ash ratio of a composition (W/FA) is between about 0.10 and about 0.30, between about 0.15 and about 0.25, between about 0.2 and about 0.25, between about 0.2 and about 0.3, between about 0.1 and about 0.2 or between about 0.05 and about 0.2. In additional embodiments, the water to fly ash ratio of a composition is greater than about 0.1, greater than about 0.15, greater than about 0.2, greater than about 0.25. In other embodiments, the water to fly ash ratio is less than about 0.35, less than about 0.3, less than about 0.25, less than about 0.2, less than about 0.15, less than about 0.1.

In certain embodiments of the present disclosure, a caisson composition does not include one or more of the following: does not include a water reducer, does not include Portland cement, does not include a set retarder, does not include any cementitious material other than cementitious fly ash, does not include a filler, does not include aggregate, does not include gravel, does not include $CaCO_3$ or lime other than that present in the cementitious fly ash and/or filler, or does not include sand. Furthermore, a composition of the present disclosure does not include native soils in some embodiments.

In certain embodiments, the flowability of a composition can be determined by a slump test C143 or a slump flow as determined by C1611.

The density of the caisson composition is important in certain embodiments. For example, the density is greater than water to displace water in the void.

In embodiments, a composition of the present disclosure has a unit weight of between about 100 pcf and about 150 pcf, of between about 110 pcf and about 140 pcf, between about 120 pcf and about 130 pcf, between about 100 pcf and about 120 pcf, between about 100 pcf and about 130 pcf, between about 120 and 140 pcf, between about 120 and 150 pcf. In other embodiments, the unit weight of a composition is greater than about 90 pcf, greater than about 100 pcf, greater than about 110 pcf, greater than about 120 pcf, greater than about 130 pcf, greater than about 140 pcf, or greater than about 150 pcf. In still other embodiments, a composition has a unit weight of less than about 160 pcf, of less than about 150 pcf, of less than about 140 pcf, of less than about 130 pcf, of less than about 120 pcf, of less than about 110 pcf, of less than about 100 pcf or of less than about 90 pcf.

One unexpected advantage of the presently disclosed caisson composition is that it undergoes significantly less shrinkage than traditional concrete. In embodiments of the present invention, the chemical shrinkage of caisson composition within 24 hours is between about 0.0001% and about 0.01% by volume, between about 0.0005% and about 0.005% by volume, between about 0.001% and about 0.003% by volume. In certain embodiments, the shrinkage of the caisson composition within 24 hours is less than about 0.05% by volume, less than about 0.03% by volume, less than about 0.01% by volume, less than about 0.008% by volume, less than about 0.005% by volume, less than about 0.003% by volume or less than about 0.001% by volume.

In embodiments of the present invention, the drying shrinkage of caisson composition at 28 days is between about 0.0001% and about 0.01% by volume, between about 0.0005% and about 0.005% by volume, between about 0.001% and about 0.003% by volume. In certain embodiments, the shrinkage of the caisson composition at 28 days is less than about 0.05% by volume, less than about 0.03% by volume, less than about 0.01% by volume, less than about 0.008% by volume, less than about 0.005% by volume, less than about 0.003% by volume or less than about 0.001% by volume.

The present disclosure also contemplates a method of determining a caisson composition for filling a void comprising: identifying at least one fly ash for use in the composition; determining a water demand of each fly ash within the composition; calculating a water demand for the composition; determining a compressive strength for the composition; determining the amount of air content necessary for the composition to have a compressive strength of between 3000 and 5000 psi at seven days, between 4000 psi and 8000 psi at 28 days, and a density of between 100 and 150 pcf; determining the time necessary to fill the void; and determining the concentration of set retarder necessary to delay the composition from setting in less time than necessary to fill the void. In an embodiment of the present disclosure a reference to fill the void means completing installation of a particular composition by filling the targeted space.

The determination of suitable fly ash, water demand, compressive strength, air content, density, time to fill the void, and the concentration of set retarder can be accomplished as discussed elsewhere in this application.

The present disclosure also contemplates a method of manufacturing a caisson comprising: determining the time necessary to fill the void; adding water and set retarder to a cementitious fly ash to make a wet mixture; adding air to the wet mixture, wherein the composition has a compressive strength of between 3000 and 5000 psi at seven days, a compressive strength of between 4000 psi and 8000 psi at 28 days, and a density of between 100 and 150 pcf; and adding the composition to the void.

Additional Compositions as Alternative to High-Strength Concrete for Construction and Method of Utilizing the Same The present invention also discloses a high-performance composition, generating high strengths, suitable for replacement of traditional concrete in applications of building construction. Like for the previously discussed caisson composition, the use of chemical retarders, and water-reducers admixtures can help to meet structural requirements for this construction composition. In some instances, traditional coarse aggregates can be used in the construction composition.

High strength concrete is typically defined as having a design strength of 6000 psi or higher. The presently disclosed construction composition creates a cost-effective alternative to traditional high-strength concrete (design strengths of 6000 psi and greater) for use in general building-construction wherever concrete is formed and placed, without necessarily needing hand finishing of the final horizontal surface. Some examples of potential use include formed columns, beams, and vertical walls. A construction composition may also be used in pre-cast concrete manufacturing plants.

A composition for construction as presently disclosed will be similar to the previously disclosed caisson composition but may have a higher final compressive strength (e.g., for simplicity the caisson section of this application is incorporated herein in its entirety.) In some embodiments, a filler may include a by-product of sand & gravel processing.

Like the caisson composition, the presently disclosed construction composition can be modified to include cellular foam to produce a high-strength material capable of freeze-thaw resistance for external applications. Alternately, higher dosages of this same foam could be added to significantly lower the unit weight of the construction composition, making it suitable as a substitute for traditional lightweight concrete for interior, elevated floor slabs. Alternately, traditional lightweight coarse aggregates can be used with the foamed, construction composition as the binder mortar. In these embodiments, the lightweight, foamed construction composition can provide lower dead-loads in building, increased fire-resistance, increased insulation-value, and sound-proofing if used as walls between dwelling units.

In an embodiment, a composition for construction comprises between 0.0001% and 10% air by volume; between 60%-95% cementitious fly ash by weight; between 5%-30% water by weight; and between 0.01% and 2% set retarder by weight, wherein the composition has compressive strength of between 3500 and 6000 psi at seven days, a compressive strength of between 5000 psi and 10000 psi at 28 days, and a density of between 100 and 150 pcf.

Construction compositions of the present disclosure will have a range of compressive strengths at various times after setting.

In an embodiment, the compressive strength (e.g., tested by ASTM C31) of a construction composition of the present disclosure at seven days will be between about 3500 psi and about 6000 psi, between 3000 psi and 5000 psi, between about 3500 psi and about 5500 psi, between about 4000 psi and about 5000 psi, between about 3500 psi and about 5000 psi, between about 4000 psi and about 6000 psi, between about 3000 psi and about 4000 psi. In additional embodiments, the compressive strength of the caisson composition at seven days will be greater than about 2500 psi, will be greater than about 3000 psi, will be greater than about 3500 psi, will be greater than about 4500 psi, will be greater than about 5000 psi, will be greater than about 5500 psi, will be greater than about 6000 psi. In an embodiment, the compressive strength of a caisson composition of the present disclosure at seven days will be less than about 7000 psi, less than about 6500 psi, less than about 6000 psi, less than about 5500 psi, less than about 5000 psi, less than about 4500 psi, less than about 4000 psi, less than about 3000 psi, or less than about 8000 psi.

In an embodiment, the compressive strength of a construction composition of the present disclosure at 28 days will be between about 5000 psi and about 10000 psi, between about 6000 psi and about 9000 psi, between about 7000 psi and about 8000 psi, between about 5000 psi and about 8000 psi, between about 6000 psi and about 8000 psi, between about 7000 psi and about 10000 psi. In additional embodiments, the compressive strength of the construction composition at 28 days will be greater than about 5000 psi, will be greater than about 6000 psi, will be greater than about 7000 psi, will be greater than about 8000 psi, will be greater than about 9000 psi, will be greater than about 10000 psi, or will be greater than about 12000 psi. In certain embodiments, the compressive strength of the construction composition at 28 days will be less than about 11000 psi, less than about 10000 psi, less than about 9000 psi, less than about 8000 psi, less than about 7000 psi, less than 6000 psi, or less than about 5500 psi.

The present disclosure also contemplates a method of determining a construction composition comprising: identifying at least one fly ash for use in the composition; determining a water demand of each fly ash within the composition; calculating a water demand for the composition; determining a compressive strength for the composition;

determining the amount of air content necessary for the composition to have a compressive strength of between 3500 and 6000 psi at seven days, a compressive strength of between 5000 psi and 10000 psi at 28 days, and a density of between 100 and 150 pcf; determining the time necessary to complete installation of the composition; and determining the concentration of set retarder necessary to delay the composition from setting in less time than necessary to complete installation of the composition.

The determination of suitable fly ash, water demand, compressive strength, air content, density, time to fill the void, and the concentration of set retarder can be accomplished as discussed elsewhere in this application.

The present disclosure also contemplates a method of manufacturing a building element comprising: determining the time necessary to complete installation of the composition; adding water and set retarder to a cementitious fly ash to make a wet mixture; adding air to the wet mixture, wherein the composition has a compressive strength of between 3500 and 6000 psi at seven days, a compressive strength of between 5000 psi and 10000 psi 28 days, and a density of between 100 and 150 pcf; and installing the composition.

Recycled Compositions and Methods of Utilizing the Same

The present disclosure also discloses a composition made of 100% recycled materials, that will achieve normal structural requirements normally achieved with Portland-cement. Like for the previously discussed caisson composition, the use of chemical retarders, and water-reducers admixtures can help to meet structural requirements for this construction composition. In some instances, traditional coarse aggregates can be used in the construction composition.

Traditional Portland-cement based concrete has sometimes used recycled concrete as coarse aggregates (gravel-sized) in the cement mixture. However, use of the ¼″ and smaller portions generated from crushing old concrete has not been widespread due to the high amount of flour-sized "fines" in the sand-size fraction of recycled concrete. Instead, virgin or manufactured sands are traditionally used in Portland-cement based concrete. Traditionally, the high fines in recycled concrete "sand" caused a high-water demand in the mixture, which tends to lower the strength of the mixture. Higher amounts of Portland cement would be required to overcome this high water demand, and that is typically uneconomical when compared to using washed, virgin sands.

When concrete is recycled in traditional means, the "rock" is screened from the "sand" size materials, for use in concrete production; the sand size is typically wasted or sold as low-value fill. The processing costs of recycling concrete are typically charged to the salable rock fraction alone, which drives its relative cost up. By using all of the recycled concrete fractions in the newly disclosed composition, lower aggregate costs are realized, as well as lower fly ash and water volumes, due to an improved aggregate packing relationship (e.g., less voids to fill with paste). In an embodiment, by using a water-reducing admixture, satisfactory strengths can be achieved, yet economically, using 100% or nearly 100% recycled materials.

In an embodiment, a recycled composition comprises between 0.0001% and 10% air by volume; between 15%-35% cementitious fly ash by weight; between 5%-15% water by weight; between 50%-80% recycled filler and between 0.01% and 2% set retarder by weight, wherein the composition sets in less than 4 hours and has a density of between 115 and 150 pcf.

The air content of the compositions of the present disclosure will vary depending on the desired properties of the composition. In some embodiments, the air content may be determined by the following formula using wet densities before and after the addition of air:

$$\text{Air content} = \frac{(\text{Unit Weight}_{no\ air} - \text{Unit Weight}_{air}) \times 100\%}{\text{Unit Weight}_{no\ air}}$$

In other embodiments, the air content can be determined using ASTM C231.

In certain embodiments, the air content is achieved by mixing an air entraining agent, i.e., a dry surfactant or liquid admixture into the cementitious fly ash and/or filler prior to addition of water. In these embodiments, the air content may by uniformly distributed by mixing directly in a truck or by mixing in a commonly used agitation/mixing device. The mixing process can occur prior to addition of water, after addition of water or simultaneously with the addition of water.

In another embodiment, the air content is achieved by addition of an air entraining agent after mixture of the dry ingredients (cementitious fly ash and filler) with water but prior to applying the composition to the void.

In specific embodiments, the air content may be achieved by adding a pre-formed cellular foam, e.g., GEOFOAM SNP foam liquid concentrate available from Cellular Concrete, LLC., 7020 Snowdrift Road, Suite 102, Allentown, Pa. 18106 or 5916 McIntyre St, Golden, Colo. 80403. The cellular foam may be pervious or non-pervious, and pre-foamed thereby reducing or alleviating the need to vigorously agitate the composition to activate the air entraining agent. Any suitable foaming agent may be used that achieves the desired end properties as described herein, e.g., an anionic foaming agent, a cationic foaming agent or a non-ionic foaming agent. An example of a pervious foam is GEOFOAM SP. An example of a non-pervious foam is GEOFOAM SNP. Suitable cellular foam is available from a variety of sources, e.g., Cellular Concrete, LLC; Provoton Foam Concrete, 28 East Larkspur Lane, Bristol, Ill. 60512; Allied Foam Tech Corp., 146 Keystone Dr. Montgomeryville, Pa. 18936; and Vermillion LLC and Associates, 2176 Sargent Daly Dr., Chattanooga, Tenn. 37421. The choice of an appropriate cellular foam is within one of skill in the art and may be dictated by cost, environmental concerns, or the need to meet the requirements of local or national agencies. In some embodiments, the foaming agent will conform to ASTM C869 and C796, in other embodiments the air entraining agent conforms to ASTM C260.

In some embodiments, the addition of cellular foam or similar air entraining agent may occur after the addition of water to the cementitious fly ash and filler immediately prior to the cementitious mixture leaving a mixing truck, as the cementitious mixture leaves the mixing truck (simultaneously) or after the cementitious mixture leaves the mixing truck.

The amount of air entraining agent necessary for a given composition will vary with the desired air content. In some embodiments, the final air content of the composition will be between about 0.001% and about 15%, between about 0.01% and about 13%, between about 0.1% and about 10%, between about 1.0% and about 8%, between about 2% and about 6%, between about 0.1% and about 5%, between about 0.1% and about 2%, between about 4% and about 10%, between about 4% and about 8%. In some embodiments, the composition does not contain any additional air content, i.e., the composition is not purposefully air entrained.

In some embodiments, the final air content will be greater than 0.1%, greater than 1%, greater than 2%, greater than 4%, greater than 6%, greater than 8%, greater than 10%, greater than 12%.

In other embodiments, the final air content of the composition will be less than 15%, less than 13%, less than 10%, less than 8%, less than 6%, less than 4%, less than 2%, less than 1%, less than 0.1%, less than 0.01%.

In an embodiment of the presently disclosure recycled composition, the cementitious fly ash is Class C fly ash as defined by ASTM C618 or the standards of a local agency. In other embodiments of the present disclosure, the cementitious fly ash can have cementitious properties without qualifying as Class C fly ash under ASTM C618 or an equivalent standard. A cementitious fly ash of the present disclosure is a fly ash that sets (e.g., solidifies to 4 psi) within about thirty minutes at a water content of 30% by weight when water and cementitious fly ash are the only ingredients.

In an embodiment of the present disclosure, a recycled composition has between about 15% and about 35% cementitious fly ash, between about 20% and about 30% cementitious fly ash, between about 15% and about 30% cementitious fly ash, between about 20% cementitious fly ash and about 35% cementitious fly ash, between about 22% and about 28% cementitious fly ash.

In some embodiments of the present disclosure, a composition has less than about 40% cementitious fly ash, less than about 35% cementitious fly ash, less than about 30% cementitious fly ash, less than about 25% cementitious fly ash, less than about 20% cementitious fly ash, less than about 15% cementitious fly ash. In additional embodiments of the present disclosure, a recycled composition has greater than about 15% cementitious fly ash, greater than about 20% cementitious fly ash, greater than about 25% cementitious fly ash, greater than about 30% cementitious fly ash, greater than about 35% cementitious fly ash.

In an embodiment of the presently disclosed composition, the water is standard city potable water. In another embodiment, the water used in the composition is substantially purified of additional minerals or other impurities. In still another embodiment of the present disclosure, the water is non-potable water. In additional embodiments, the water is selected based on its natural impurities, i.e., specific mineral content like calcium, magnesium, iron, or similar water minerals.

The water content of the presently disclosed composition may vary depending on desired flowability, setting time and final compressive strength. In an embodiment of the present disclosure, a composition has a the water content of between about 5% and about 15%, between about 7% and about 12%, between about 5% and about 10%, between about 10% and about 15%. In additional embodiments, a composition has greater than about 3% water, greater than about 5% water, greater than about 7% water, greater than about 10% water, or greater than about 13% water. In other embodiments, a composition has less than about 20% water, less than about 15% water, less than about 10% water, less than about 7% water, less than about 5% water. Any water included with additional ingredients, e.g., aqueous water retarders, foaming agents, etc. under the circumstances encountered in the field by the inventors has been negligible in comparison to the primary batch water and therefore has not been included in the above calculations. Depending on the actual water content of the additional ingredients used it may be necessary to consider the additional water in the final water concentrations.

In some embodiments of the present disclosure, a composition will include at least one filler. In additional embodiments, a composition will include only one filler, while in other embodiments, a composition will contain only two fillers. In still additional embodiments, a composition will contain less than 3 fillers or less than 4 fillers. A filler in the present disclosure can be additional fly ash, e.g., type F fly ash as determined by ASTM C618 or equivalent standard. A filler can also be non-specification grade non-cementitious fly ash, e.g., a fly ash that does not meet the specifications determined by ASTM C618. In certain embodiments a filler can be sand, bottom ash, quarry fines, soil, gravel and Portland cement, aggregate, or recycled version thereof. In some embodiments, the recycled filler is a recycled aggregate. In additional embodiments, the recycled aggregate is about 100% recycled aggregate while in other embodiments the recycled aggregate is less than 100% recycled aggregate but greater than 50% recycled aggregate. In additional embodiments, the recycled aggregate is 90% or 95% or 99% recycled aggregate. Determination of the filler material can be based on economics, availability, city, county and/or state specifications, or on the desired properties of the composition, e.g., desired setting time, flowability, or final compressive strength.

In an embodiment, a composition of the present disclosure will have between about 50% and about 80% filler, between about 55% and about 75% filler, between about 60% and about 50% filler, between about 50% and about 60% filler, between about 50% and about 70%, between about 60% and about 80%, between about 65% and about 80% filler. In certain embodiments, a composition of the present disclosure will have less than about 80% filler, less than about 75% filler, less than about 70% filler, less than about 65% filler, less than about 60% filler, less than about 55% filler. In still other embodiments, a composition of the present disclosure will have greater than about 50% filler, greater than about 55% filler, greater than about 60% filler, greater than about 65% filler, greater than about 70% filler, greater than about 75% filler, or greater than about 80% filler.

Recycled compositions will comprise a set retarder in most embodiments. A set retarder is a compound capable of delaying the set time of the composition. In certain embodiments, delaying the set time is necessary to allow a recycled composition to completely fill a void before setting. An example of a set retarder may be citric acid or borax, or a combination thereof. In certain embodiments, the set retarder is liquid while in other embodiments the set retarder is a powder. An appropriate set retarder will be well known to a person of ordinary skill in the art.

In an embodiment, the concentration of set retarder is between about 0.01% and about 3%, between about 0.01% and about 2% between about 0.05% and about 2.5%, between about 0.1% and about 2%, between about 0.5% and about 1.5%, between about 0.0001% and about 1.0%. In some embodiments, the set retarder is greater than about 0.001%, is greater than about 0.01% is greater than about 0.05%, is greater than about 0.1%, is greater than about 0.5%, is greater than about 1.0%, is greater than about 1.5%, or is greater than about 2.0%. In certain embodiments, the set retarder is less than about 3.0%, less than about 2.5%, less than about 2.0%, less than about 1.5%, less than about 1.0%, less than about 0.5%, less than about 0.3%, less than about 0.1%, less than about 0.01%, less than about 0.001%.

In some embodiments, the composition may further comprise a water reducer. Water reducers may be used when a higher final strength is desired at a specified density and fluidity. In some embodiments the water reducer will be powder while in other embodiments it will be a liquid water reducer. In an embodiment, the water reducer is CHRYSO 256 (high range) or 380 (midrange) or similar composition. A water reducer is a chemical (e.g., chemical composition) that allows a mixture to maintain the same fluidity with less water or more fluidity with the same amount of water.

In an embodiment, the concentration of the water reducer is between about 0.01% and about 3%, between about 0.01% and about 2% between about 0.05% and about 2.5%, between about 0.1% and about 2%, between about 0.5% and about 1.5%, between about 0.0001% and about 1.0%. In some embodiments, the water reducer is greater than about 0.001%, is greater than about 0.01% is greater than about 0.05%, is greater than about 0.1%, is greater than about 0.5%, is greater than about 1.0%, is greater than about 1.5%, or is greater than about 2.0%. In certain embodiments, the water reducer is less than about 3.0%, less than about 2.5%, less than about 2.0%, less than about 1.5%, less than about 1.0%, less than about 0.5%, less than about 0.3%, less than about 0.1%, less than about 0.01%, less than about 0.001%.

Compositions of the present disclosure will have a range of possible set times based on the desired application. For example, the larger the building element or the slower the pump rate, the longer the set time necessary to complete filling the building element before the composition sets. In some embodiments, the set time of the building element composition is determined by measuring penetration resistance with a pocket penetrometer (e.g., with a resistance of 4 psi as typically used in standard ASTM WK 27337) or cement setting time standard ASTM C403. In an embodiment of the present disclosure, the set time for a composition can be between about 60 minutes and about 4 hours, between about 1.5 hours and about 3.5 hours, between about 2 hours and about 3 hours. In additional embodiments, a composition has a set time of less than 4 hours, of less than about 3 hours, of less than about 2 hours, of less than about 1.5 hours, of less than about 1 hour. In other embodiments, a composition has a set time of greater than about 1 hours, of greater than about 1.5 hours, of greater than about 2 hours, of greater than about 2.5 hours, of greater than about 3 hours, of greater than about 4 hours.

Recycled compositions of the present disclosure will have a range of compressive strengths at various times after the addition of a composition to a caisson void depending on the desired properties of the composition.

In certain embodiments, the compressive strength is measured at 1 day, 3 days, 7 days and 28 days where the 28 day measurement is considered the final compressive strength. In other embodiments, the compressive strength is measured more often at smaller intervals or less often at larger intervals. In some embodiments, the compressive strength is measured at 90 days.

In an embodiment, the compressive strength (e.g., tested by ASTM C31) of a recycled composition of the present disclosure at seven days will be between about 3500 psi and about 6000 psi, between about 3750 psi and about 5500 psi, between about 4000 psi and about 5000 psi, between about 3500 psi and about 5000 psi, between about 4000 psi and about 6000 psi, between about 5000 psi and about 6000 psi. In additional embodiments, the compressive strength of the recycled composition at seven days will be greater than about 3000 psi, will be greater than about 3500 psi, will be greater than about 4000 psi, will be greater than about 4500 psi, will be greater than about 5000 psi, will be greater than about 5500 psi, will be greater than about 6000 psi. In an embodiment, the compressive strength of a recycled composition of the present disclosure at seven days will be less than about 7000 psi, less than about 6500 psi, less than about 6000 psi, less than about 5500 psi, less than about 5000 psi, less than about 4500 psi, less than about 4000 psi, or less than about 8000 psi.

In an embodiment, the compressive strength of a recycled composition of the present disclosure at 28 days will be between about 5000 psi and about 10000 psi, between about 6000 psi and about 9000 psi, between about 7000 psi and about 8000 psi, between about 7000 psi and about 10000 psi, between about 9000 psi and about 11000 psi, between about 5000 psi and about 8000 psi, between about 5000 psi and about 7000 psi. In additional embodiments, the compressive strength of the recycled composition at 28 days will be greater than about 4500 psi, will be greater than about 5000 psi, will be greater than about 6000 psi, will be greater than about 7000 psi, will be greater than about 8000 psi, will be greater than about 9000 psi, or will be greater than about 10000 psi. In certain embodiments, the compressive strength of the recycled composition at 28 days will be less than about 11000 psi, less than about 10000 psi, less than about 9000 psi, less than about 8000 psi, less than about 7000 psi, less than about 6000 psi, or less than about 5000 psi.

In certain embodiments of the present disclosure, a suitable recycled composition can be defined by the water to fly ash ratio, e.g., when using no filler, when using non-cementitious fly ash filler, or other suitable filler like recycled aggregate. In certain embodiments, the water to fly ash ratio will be a water to cementitious fly ash plus additional non-cementitious fly ash filler ratio.

In certain embodiments, a composition can have a range of water to fly ash ratios depending on the water demand of the fly ash (or included filler), the desired flowability, the desired setting time and the desired final compressive strength. In certain embodiments, the water to fly ash ratio of a composition (W/FA) is between about 0.10 and about 0.30, between about 0.15 and about 0.25, between about 0.2 and about 0.25, between about 0.2 and about 0.3, between about 0.1 and about 0.2 or between about 0.05 and about 0.2. In additional embodiments, the water to fly ash ratio of a composition is greater than about 0.1, greater than about 0.15, greater than about 0.2, greater than about 0.25. In other embodiments, the water to fly ash ratio is less than about 0.35, less than about 0.3, less than about 0.25, less than about 0.2, less than about 0.15, less than about 0.1.

In certain embodiments of the present disclosure, a recycled composition does not include one or more of the following: does not include a water reducer, does not include Portland cement, does not include a set retarder, does not include any cementitious material other than cementitious fly ash, does not include a filler, does not include aggregate, does not include gravel, does not include $CaCO_3$ or lime other than that present in the cementitious fly ash and/or filler, or does not include sand. Furthermore, a composition of the present disclosure does not include native soils in some embodiments.

In certain embodiments, the flowability of a composition can be determined by a slump test C143 or a slump flow as determined by C1611 or spread as determined by D6103.

The density of the recycled composition is important in certain embodiments. In embodiments, a composition of the present disclosure has a unit weight of between about 115 pcf and about 150 pcf, of between about 120 pcf and about 145 pcf, between about 125 pcf and about 135 pcf, between about 115 pcf and about 140 pcf, between about 115 pcf and about 135 pcf, between about 125 pcf and 150 pcf, between about 120 pcf and 150 pcf. In other embodiments, the unit weight of a composition is greater than about 90 pcf, greater than about 100 pcf, greater than about 110 pcf, greater than about 120 pcf, greater than about 130 pcf, greater than about 140 pcf, or greater than about 150 pcf. In still other embodiments, a composition has a unit weight of less than about 160 pcf, of less than about 150 pcf, of less than about 140 pcf, of less than about 130 pcf, of less than about 120 pcf, of less than about 110 pcf, of less than about 100 pcf or of less than about 90 pcf.

The present disclosure also contemplates a method of determining a recycled composition for construction comprising: identifying at least one fly ash for use in the composition; determining a water demand of each fly ash within the composition; calculating a water demand for the composition, including recycled filler, determining a compressive strength for the composition; determining the amount of air content necessary for the composition to set is less than 4 hours and have a density of between 115 pcf and 150 pcf; determining the time necessary to finish a construction project; and determining the concentration of set retarder necessary to delay the composition from setting in less time than necessary to finish the construction project.

The determination of suitable fly ash, water demand, compressive strength, air content, density, time to finish the construction project, and the concentration of set retarder can be accomplished as discussed elsewhere in this application.

Compositions for Use as Wicking Layer and Methods of Utilizing the Same

This present disclosure additionally provides an economical, easy-to-install composition for use as wicking layer under concrete slabs, instead of the general industry recommended layer of compacted crusher fines. The composition can use cementitious fly ash alone or in combination with an additional filler for better economy. In an embodiment, water-reducing admixtures are used to increase the strength of the cementitious slurry, prior to foaming with a permeable, pre-formed, cellular foam, allowing higher air contents for even greater economy. The slab-wicking composition is placed & screeded to a uniform depth, and is sufficiently hard the next day to allow foot-traffic, and subsequent concrete placement when dry enough to wick.

With VOC-compliant flooring adhesives mandated for interior applications, vapor transmissions of moisture from and through concrete floor slabs is a critical issue for both successful adhesion of flooring materials, as well as to the construction schedule. If concrete slabs are placed directly on an effective vapor barrier, the concrete will dry out rather quickly to allow flooring adhesives. However, drying only occurs from the top of slab; that results in greater drying shrinkage of the surface, which promotes slab curling, where the edges of each concrete slab raise up during the drying process. The loss of support at the joints can lead to flexural cracking, as wheel loads cross these joints. Even without flexural cracking, the inherent flatness of the concrete floor is lost, when slabs curl, due to differential drying shrinkage.

Industry recommendations (ACI 302 11.11) are to install a minimum of 4" of crusher fines as a dry to almost-dry base, that will wick some moisture away from the bottom surface of concrete. If the top surface is well sealed to prevent moisture loss, fairly uniform curing and drying shrinkage will occur throughout the depth of the concrete slab, hence reducing slab curling. However, it is often difficult to transport crusher fines (often 135 pcf when compacted in-place), spread & compact them, and have them stable to foot-traffic for rebar and concrete placement, when the moisture content is almost dry because dry granular materials tend to ravel & shift.

In an embodiment of the present disclosure, a cementitious slurry is delivered or manufactured on-site with cellular grout production equipment. A cellular, pervious foam is added to the slurry, either in the revolving drum mixer, or in an in-line mixing device. The cellular, pervious concrete (20-60 pcf) is then pumped to the point of placement, where it is easily screeded over forms to ensure a uniform depth, and flat subgrade for subsequent concrete placement.

In an embodiment, when the cellular, pervious concrete has gained sufficient strength to handle foot traffic, installation of reinforcing steel may begin. When the cellular concrete has dried out sufficiently to provide adequate wicking of excess moisture from the concrete slab, concrete placement can begin using conventional methods. The pervious, cellular concrete will readily wick-away sufficient moisture to prevent slab curling, however will dry out in similar time to concrete directly on a vapor barrier, to allow vapor transmissions low enough for floor adhesives.

In an embodiment, a wicking composition comprises between 45% and 80% air by volume; between 70%-90% cementitious fly ash by weight; and between 10%-30% water by weight, wherein the composition sets in less than 4 hours, has a compressive strength of between 100 and 600 psi after 7 days and has a density of between 20 and 60 pcf.

The air content of the compositions of the present disclosure will vary depending on the desired properties of the composition. In some embodiments, the air content may be determined by the following formula using wet densities before and after the addition of air:

$$\text{Air content} = \frac{(\text{Unit Weights}_{no\ air} - \text{Unit Weight}_{air}) \times 100\%}{\text{Unit Weight}_{no\ air}}$$

In other embodiments, the air content can be determined using ASTM C231.

In certain embodiments, the air content is achieved by mixing an air entraining agent, i.e., a dry surfactant or liquid admixture into the cementitious fly ash and/or filler prior to addition of water. In these embodiments, the air content may by uniformly distributed by mixing directly in a truck or by mixing in a commonly used agitation/mixing device. The mixing process can occur prior to addition of water, after addition of water or simultaneously with the addition of water.

In another embodiment, the air content is achieved by addition of an air entraining agent after mixture of the dry ingredients (cementitious fly ash and filler) with water but prior to applying the composition to the void.

In specific embodiments, the air content may be achieved by adding a pre-formed cellular foam, e.g., GEOFOAM SNP foam liquid concentrate available from Cellular Concrete, LLC., 7020 Snowdrift Road. Suite 102, Allentown, Pa. 18106 or 5916 McIntyre St, Golden, Colo. 80403. The cellular foam may be pervious or non-pervious, and pre-foamed thereby reducing or alleviating the need to vigorously agitate the composition to activate the air entraining agent. Any suitable foaming agent may be used that achieves the desired end properties as described herein, e.g., an anionic foaming agent, a cationic foaming agent or a non-ionic foaming agent. An example of a pervious foam is GEOFOAM SP. An example of a non-pervious foam is GEOFOAM SNP. Suitable cellular foam is available from a variety of sources, e.g., Cellular Concrete, LLC; Provoton Foam Concrete, 28 East Larkspur Lane, Bristol, Ill. 60512; Allied Foam Tech Corp., 146 Keystone Dr. Montgomeryville, Pa. 18936; and Vermillion LLC and Associates, 2176 Sargent Daly Dr., Chattanooga, Tenn. 37421. The choice of an appropriate cellular foam is within one of skill in the art and may be dictated by cost, environmental concerns, or the need to meet the requirements of local or national agencies. When wicking is a desired property, a pervious foam can be used. In some embodiments, the foaming agent will conform to ASTM C869 and C796, in other embodiments the air entraining agent conforms to ASTM C260.

In some embodiments, the addition of cellular foam or similar air entraining agent may occur after the addition of water to the cementitious fly ash and filler immediately prior to the cementitious mixture leaving a mixing truck, as the cementitious mixture leaves the mixing truck (simultaneously) or after the cementitious mixture leaves the mixing truck.

The amount of air entraining agent necessary for a given composition will vary with the desired air content. In some embodiments, the final air content of the composition will be between about 45% and about 80%, between about 50% and about 75%, between about 55% and about 70%, between about 45% and about 60%, between about 50% and about 60%, between about 60% and about 80%, between about 65% and about 75%.

In some embodiments, the final air content will be greater than 45%, greater than 50%, greater than 55%, greater than 60%, greater than 65%, greater than 75%, greater than 80%, greater than 85%.

In other embodiments, the final air content of the composition will be less than 85%, less than 80%, less than 75%, less than 70%, less than 65%, less than 60%, less than 55%, less than 50%, less than 45%.

In an embodiment of the presently disclosure wicking composition, the cementitious fly ash is Class C fly ash as defined by ASTM C618 or the standards of a local agency. In other embodiments of the present disclosure, the cementitious fly ash can have cementitious properties without qualifying as Class C fly ash under ASTM C618 or an equivalent standard. A cementitious fly ash of the present disclosure is a fly ash that sets (e.g., solidifies to 4 psi) within about thirty minutes at a water content of 30% by weight when water and cementitious fly ash are the only ingredients.

In an embodiment of the present disclosure, a wicking composition has between about 70% and about 90% cementitious fly ash, between about 75% and about 85% cementitious fly ash, between about 70% and about 80% cementitious fly ash, between about 80% cementitious fly ash and about 90% cementitious fly ash.

In some embodiments of the present disclosure, a composition has less than about 90% cementitious fly ash, less than about 85% cementitious fly ash, less than about 80% cementitious fly ash, less than about 75% cementitious fly ash, less than about 70% cementitious fly ash, less than about 65% cementitious fly ash. In additional embodiments of the present disclosure, a wicking composition has greater than about 70% cementitious fly ash, greater than about 75% cementitious fly ash, greater than about 80% cementitious fly ash, greater than about 85% cementitious fly ash, greater than about 90% cementitious fly ash.

In an embodiment of the presently disclosed composition, the water is standard city potable water. In another embodiment, the water used in the composition is substantially purified of additional minerals or other impurities. In still another embodiment of the present disclosure, the water is non-potable water. In additional embodiments, the water is selected based on its natural impurities, i.e., specific mineral content like calcium, magnesium, iron, or similar water minerals.

The water content of the presently disclosed composition may vary depending on desired flowability, setting time and final compressive strength. In an embodiment of the present disclosure, a composition has the water content of between about 10% and about 30%, between about 15% and about 25%, between about 10% and about 20%, between about 20% and about 30%. In additional embodiments, a composition has greater than about 10% water, greater than about 15% water, greater than about 20% water, greater than about 25% water, or greater than about 30% water. In other embodiments, a composition has less than about 30% water, less than about 25% water, less than about 20% water, less than about 15% water, less than about 10% water. Any water included with additional ingredients, e.g., aqueous water retarders, foaming agents, etc. under the circumstances encountered in the field by the inventors has been negligible in comparison to the primary batch water and therefore has not been included in the above calculations. Depending on the actual water content of the additional ingredients used it may be necessary to consider the additional water in the final water concentrations.

In some embodiments of the present disclosure, a composition will include at least one filler. In additional embodiments, a composition will include only one filler, while in other embodiments, a composition will contain only two fillers. In still additional embodiments, a composition will contain less than 3 fillers or less than 4 fillers. A filler in the present disclosure can be additional fly ash, e.g., type F fly ash as determined by ASTM C618 or equivalent standard. A filler can also be non-specification grade non-cementitious fly ash, e.g., a fly ash that does not meet the specifications determined by ASTM C618. In certain embodiments a filler can be sand, bottom ash, quarry fines, soil, gravel and Portland cement, aggregate, or recycled version thereof. Determination of the filler material can be based on economics, availability, city, county and/or state specifications, or on the desired properties of the composition, e.g., desired setting time, flowability, or final compressive strength.

Presently disclosed compositions will comprise a set retarder in some embodiments. A set retarder is a compound capable of delaying the set time of the composition. In certain embodiments, delaying the set time is necessary to allow a composition to be installed before setting. An example of a set retarder may be citric acid or borax, or a combination thereof. In certain embodiments, the set retarder is liquid while in other embodiments the set retarder is a powder. An appropriate set retarder will be well known to a person of ordinary skill in the art.

In an embodiment, the concentration of set retarder is between about 0.01% and about 3%, between about 0.01% and about 2% between about 0.05% and about 2.5%, between about 0.1% and about 2%, between about 0.5% and about 1.5%, between about 0.0001% and about 1.0%. In some embodiments, the set retarder is greater than about 0.001%, is greater than about 0.01% is greater than about 0.05%, is greater than about 0.1%, is greater than about 0.5%, is greater than about 1.0%, is greater than about 1.5%, or is greater than about 2.0%. In certain embodiments, the set retarder is less than about 3.0%, less than about 2.5%, less than about 2.0%, less than about 1.5%, less than about 1.0%, less than about 0.5%, less than about 0.3%, less than about 0.1%, less than about 0.01%, less than about 0.001%.

In some embodiments, the composition may further comprise a water reducer. Water reducers may be used when a higher final strength is desired at a specified density and fluidity. In some embodiments the water reducer will be powder while in other embodiments it will be a liquid water reducer. In an embodiment, the water reducer is CHRYSO 256 (high range) or 380 (midrange) or similar composition. A water reducer is a chemical (e.g., chemical composition) that allows a mixture to maintain the same fluidity with less water or more fluidity with the same amount of water.

In an embodiment, the concentration of the water reducer is between about 0.01% and about 3%, between about 0.01% and about 2% between about 0.05% and about 2.5%, between about 0.1% and about 2%, between about 0.5% and about 1.5%, between about 0.0001% and about 1.0%. In some embodiments, the water reducer is greater than about 0.001%, is greater than about 0.01% is greater than about 0.05%, is greater than about 0.1%, is greater than about 0.5%, is greater than about 1.0%, is greater than about 1.5%, or is greater than about 2.0%. In certain embodiments, the water reducer is less than about 3.0%, less than about 2.5%, less than about 2.0%, less than about 1.5%, less than about 1.0%, less than about 0.5%, less than about 0.3%, less than about 0.1%, less than about 0.01%, less than about 0.001%.

Compositions of the present disclosure will have a range of possible set times based on the desired application. In some embodiments, the set time of the wicking composition is determined by measuring penetration resistance with a pocket penetrometer (e.g., with a resistance of 4 psi as typically used in standard ASTM WK 27337) or cement setting time standard ASTM C403. In an embodiment of the present disclosure, the set time for a composition can be between about 60 minutes and about 2 hours, between about 1.5 hours and about 3.5 hours, between about 2 hours and about 3 hours. In additional embodiments, a composition has a set time of less than 4 hours, of less than about 3 hours, of less than about 2 hours, of less than about 1.5 hours, of less than about 1 hour. In other embodiments, a composition has a set time of greater than about 1 hours, of greater than about 1.5 hours, of greater than about 2 hours, of greater than about 2.5 hours, of greater than about 3 hours, of greater than about 4 hours.

Wicking compositions of the present disclosure will have a range of compressive strengths at various times after the addition of a composition to a floor.

In certain embodiments, the compressive strength is measured at 1 day, 3 days, 7 days and 28 days where the 28 day measurement is considered the final compressive strength. In other embodiments, the compressive strength is measured more often at smaller intervals or less often at larger intervals. In some embodiments, the compressive strength is measured at 90 days. In an embodiment, the bearing penetration or capacity resistance of a composition is measured at 1 day, 7 days and 28 days using ASTM WK 27337 or C403.

In an embodiment, the compressive strength (e.g., tested by ASTM C495) of a wicking composition of the present disclosure at seven days will be between about 100 psi and about 600 psi, between about 200 psi and about 500 psi, between about 300 psi and about 400 psi, between about 100 psi and about 300 psi, between about 400 psi and about 600 psi, between about 300 psi and about 600 psi. In additional embodiments, the compressive strength of the wicking composition at seven days will be greater than about 100 psi, will be greater than about 200 psi, will be greater than about 300 psi, will be greater than about 400 psi, will be greater than about 500 psi, will be greater than about 600 psi, will be greater than about 700 psi. In an embodiment, the compressive strength of a wicking composition of the present disclosure at seven days will be less than about 700 psi, less than about 600 psi, less than about 500 psi, less than about 400 psi, less than about 300 psi, less than about 200 psi, less than about 100 psi, In an embodiment, the compressive strength of a wicking composition of the present disclosure at 28 days will be between about 150 psi and about 900 psi, between about 200 psi and about 800 psi, between about 300 psi and about 700 psi, between about 400 psi and about 600 psi, between about 150 psi and about 400 psi, between about 400 psi and about 800 psi, between about 500 psi and about 800 psi. In additional embodiments, the compressive strength of a wicking composition at 28 days will be greater than about 100 psi, will be greater than about 200 psi, will be greater than about 300 psi, will be greater than about 400 psi, will be greater than about 500 psi, will be greater than about 600 psi, or will be greater than about 700 psi. In certain embodiments, the compressive strength of a wicking composition at 28 days will be less than about 800 psi, less than about 700 psi, less than about 600 psi, less than about 500 psi, less than about 400 psi, less than about 300 psi, or less than about 200 psi.

In certain embodiments of the present disclosure, a suitable wicking composition can be defined by the water to fly ash ratio, e.g., when using no filler, when using non-cementitious fly ash filler, or other suitable filler like recycled aggregate. In certain embodiments, the water to fly ash ratio will be a water to cementitious fly ash plus additional non-cementitious fly ash filler ratio.

In certain embodiments, a composition can have a range of water to fly ash ratios depending on the water demand of the fly ash (or included filler), the desired flowability, the desired setting time and the desired final compressive strength. In certain embodiments, the water to fly ash ratio of a composition (W/FA) is between about 0.10 and about 0.30, between about 0.15 and about 0.25, between about 0.2 and about 0.25, between about 0.2 and about 0.3, between about 0.1 and about 0.2 or between about 0.05 and about 0.2. In additional embodiments, the water to fly ash ratio of a composition is greater than about 0.1, greater than about 0.15, greater than about 0.2, greater than about 0.25. In other embodiments, the water to fly ash ratio is less than about 0.35, less than about 0.3, less than about 0.25, less than about 0.2, less than about 0.15, less than about 0.1.

In certain embodiments of the present disclosure, a wicking composition does not include one or more of the following: does not include a water reducer, does not include Portland cement, does not include a set retarder, does not include any cementitious material other than cementitious fly ash, does not include a filler, does not include aggregate, does not include gravel, does not include $CaCO_3$ or lime other than that present in the cementitious fly ash and/or filler, or does not include sand.

In certain embodiments, the flowability of a composition can be determined by a slump test C143 or a slump flow as determined by C1611 or spread as determined by D6103.

The density of the wicking composition is important in certain embodiments. In embodiments, a composition of the present disclosure has a unit weight of between about 20 pcf and about 60 pcf, of between about 30 pcf and about 50 pcf, between about 40 pcf and about 50 pcf, between about 20 pcf and about 40 pcf, between about 30 pcf and about 50 pcf. In other embodiments, the unit weight of a composition is greater than about 15 pcf, greater than about 20 pcf, greater than about 30 pcf, greater than about 40 pcf, greater than about 50 pcf, greater than about 60 pcf, or greater than about 25 pcf. In still other embodiments, a composition has a unit weight of less than about 60 pcf, of less than about 50 pcf, of less than about 40 pcf, of less than about 35 pcf, of less than about 30 pcf, of less than about 25 pcf, of less than about 20 pcf or of less than about 45 pcf.

Compositions for Pavement Patching and Methods of Utilizing the Same

The present disclosure also reveals a composition for use as a more durable temporary pavement patch than traditional "cold-mix" asphalt products currently in wide use. In addition to an improvement in durability, the compositions are also less expensive than other high-strength, fast-setting mixtures using Portland cement and other hydraulic cement binders. The high-strength patch of the present disclosure can be driven on within a few hours. In an embodiment, a by-product of sand & gravel processing can also be incorporated into the main patch mixture, for economy. In additional embodiments, small-size gravel, sand, or other aggregates can be sprinkled on to the patch surface, before final set occurs, in increase durability and skid-resistance for public safety.

Street cuts through pavements are often required to repair buried utilities, with subsequent backfilling of the trench and patching of the asphalt or concrete pavement. Often, the temperature or time to re-open the street to traffic does not allow the installation of a properly-constructed patch of like material of the pavement. Traditionally, "cold-mix" asphalt materials are frequently used as a quick, temporary trench patch. However, cold-mix patches are easily damaged by snowplows and often require frequent maintenance, until the permanent pavement repair is made in the spring. Also, these cold-mix materials are subject to rutting under truck traffic, after the occurrence of warm weather but before the permanent trench patch is installed. Thus, the present disclosure provides a fast-acting, economical, more-durable temporary pavement patch material & system.

In an embodiment of the present disclosure, a composition for patching a trench comprising between 70%-95% cementitious fly ash by weight; between 10% and 30% water by weight; and between 0.01% and 2% set retarder by weight, wherein the composition has compressive strength of between 150 and 450 psi in 1 hour, a compressive strength of between 600 and 1800 psi in 4 hours, and a set time of less than 40 minutes.

In some embodiments of the patch composition, no additional air content is added, e.g., no air entraining agent is used. In other embodiments, the air content of the compositions of the present disclosure will vary depending on the desired properties of the composition. For example, the amount of air within the composition helps control the final strength of the patch composition.

In some embodiments, the air content may be determined by the following formula using wet densities before and after the addition of air:

$$\text{Air content} = \frac{(\text{Unit Weights}_{no\ air} - \text{Unit Weight}_{air}) \times 100\%}{\text{Unit Weight}_{no\ air}}$$

In other embodiments, the air content can be determined using ASTM C231.

In certain embodiments, the air content is achieved by mixing an air entraining agent, i.e., a dry surfactant or liquid admixture into the cementitious fly ash and/or filler prior to addition of water. In these embodiments, the air content may by uniformly distributed by mixing directly in a truck or by mixing in a commonly used agitation/mixing device. The mixing process can occur prior to addition of water, after addition of water or simultaneously with the addition of water.

In another embodiment, the air content is achieved by addition of an air entraining agent after mixture of the dry ingredients (cementitious fly ash and possible filler) with water but prior to applying the composition to the void.

In specific embodiments, the air content may be achieved by adding a pre-formed cellular foam, e.g., GEOFOAM SNP foam liquid concentrate available from Cellular Concrete, LLC., 7020 Snowdrift Road, Suite 102, Allentown, Pa. 18106 or 5916 McIntyre St, Golden, Colo. 80403. The cellular foam may be pervious or non-pervious, and pre-foamed thereby reducing or alleviating the need to vigorously agitate the composition to activate the air entraining agent. Any suitable foaming agent may be used that achieves the desired end properties as described herein, e.g. an anionic foaming agent, a cationic foaming agent or a non-ionic foaming agent. An example of a pervious foam is GEOFOAM SP. An example of a non-pervious foam is GEOFOAM SNP. Suitable cellular foam is available from a variety of sources, e.g., Cellular Concrete, LLC; Provoton Foam Concrete, 28 East Larkspur Lane, Bristol, Ill. 60512; Allied Foam Tech Corp., 146 Keystone Dr. Montgomeryville, Pa. 18936; and Vermillion LLC and Associates, 2176 Sargent Daly Dr., Chattanooga, Tenn. 37421. The choice of an appropriate cellular foam is within one of skill in the art and may be dictated by cost, environmental concerns, or the need to meet the requirements of local or national agencies. In some embodiments, the foaming agent will conform to ASTM C869 and C796, in other embodiments the air entraining agent conforms to ASTM C260.

In some embodiments, the addition of cellular foam or similar air entraining agent may occur after the addition of water to the cementitious fly ash and/or filler immediately prior to the cementitious mixture leaving a mixing truck, as the cementitious mixture leaves the mixing truck (simultaneously) or after the cementitious mixture leaves the mixing truck.

The amount of air entraining agent necessary for a given composition will vary with the desired air content, e.g., the desired final compressive strength. In some embodiments, the final air content of the composition will be between about 0.001% and about 15%, between about 0.01% and about 13%, between about 0.1% and about 10%, between about 1.0% and about 8%, between about 2% and about 6%, between about 0.1% and about 5%, between about 0.1% and about 2%, between about 4% and about 10%, between about 4% and about 8%. In some embodiments, the composition does not contain any additional air content, i.e., the composition is not purposefully air entrained.

In some embodiments, the final air content will be greater than 0.1%, greater than 1%, greater than 2%, greater than 4%, greater than 6%, greater than 8%, greater than 10%, greater than 12%.

In other embodiments, the final air content of the composition will be less than 15%, less than 13%, less than 10%, less than 8%, less than 6%, less than 4%, less than 2%, less than 1%, less than 0.1%, less than 0.01%.

In an embodiment of the present disclosure, the cementitious fly ash is Class C fly ash as defined by ASTM C618 or the standards of a local agency. In other embodiments of the present disclosure, the cementitious fly ash can have cementitious properties without qualifying as Class C fly ash under ASTM C618 or an equivalent standard. A cementitious fly ash of the present disclosure is a fly ash that sets (e.g., solidifies to 4 psi) within about thirty minutes at a water content of 30% by weight when water and cementitious fly ash are the only ingredients.

In an embodiment of the present disclosure, a composition has between about 60% and about 95% cementitious fly ash, between about 65% and about 90% cementitious fly ash, between about 65% and about 85% cementitious fly ash, between about 70% cementitious fly ash and about 80% cementitious fly ash, between about 60% and about 80% cementitious fly ash, and between about 70% and about 90% cementitious fly ash.

In some embodiments of the present disclosure, a composition has less than about 95% cementitious fly ash, less than about 90% cementitious fly ash, less than about 85% cementitious fly ash, less than about 80% cementitious fly ash, less than about 75% cementitious fly ash, less than about 70% cementitious fly ash, less than about 65% cementitious fly ash or less than about 60% cementitious fly ash. In additional embodiments of the present disclosure, the composition has greater than about 60% cementitious fly ash, greater than about 65% cementitious fly ash, cementitious fly ash, greater than about 70% cementitious fly ash, greater than about 75% cementitious fly ash, greater than about 80% cementitious fly ash, greater than about 85% cementitious fly ash, greater than about 90% cementitious fly ash, or greater than about 95% cementitious fly ash.

In an embodiment of the presently disclosed composition, the water is standard city potable water. In another embodiment, the water used in the composition is substantially purified of additional minerals or other impurities. In still another embodiment of the present disclosure, the water is non-potable water. In additional embodiments, the water is selected based on its natural impurities, i.e., specific mineral content like calcium, magnesium, iron, or similar water minerals.

The water content of the presently disclosed composition may vary depending on desired flowability, setting time and final compressive strength. In an embodiment of the present disclosure, a composition has a water content of between about 10% and about 45%, between about 15% and about 35%, between about 20% and about 30%, between about 10% and about 30%, between about 10% and about 25%, between about 20% and about 45%. In additional embodiments, a composition has greater than about 10% water, greater than about 20% water, greater than about 30% water, greater than about 40% water, or greater than about 50% water. In other embodiments, a composition has less than about 55% water, less than about 45% water, less than about 35% water, less than about 25% water, less than about 20% water, less than about 15% water, or less than about 10% water. Any water included with additional ingredients, e.g, aqueous water retarders, foaming agents, etc. under the circumstances encountered in the field by the inventors has been negligible in comparison to the primary batch water and therefore has not been included in the above calculations. Depending on the actual water content of the additional ingredients used it may be necessary to consider the additional water in the final water concentrations.

In some embodiments of the present disclosure, a composition will include at least one filler. In additional embodiments, a composition will include only one filler, while in other embodiments, a composition will contain only two fillers. In still additional embodiments, a composition will contain less than 3 fillers or less than 4 fillers. A filler in the present disclosure can be additional fly ash, e.g., type F fly ash as determined by ASTM C618 or equivalent standard. A filler can also be non-specification grade non-cementitious fly ash, e.g., a fly ash that does not meet the specifications determined by ASTM C618. In certain embodiments a filler can be sand, bottom ash, quarry fines, soil, gravel and Portland cement, aggregate, or recycled version thereof. Determination of the filler material can be based on economics, availability, city, county and/or state specifications, or on the desired properties of the composition, e.g., desired setting time, flowability, or final compressive strength.

In an embodiment, a composition of the present disclosure will have between about 1% and about 40% filler, between about 5% and about 35% filler, between about 10% and about 30% filler, between about 15% and about 25% filler, between about 1% and about 20%, between about 5% and about 20%, between about 5% and about 15%, between about 30% and about 40%. In certain embodiments, a composition of the present disclosure will have less than about 50% filler, less than about 70% filler, less than about 60% filler, less than about 50% filler, less than about 40% filler, less than about 35% filler, less than about 30% filler, less than about 25% filler, less than about 20% filler, less than about 15% filler, less than about 10% filler, less than about 5% filler or less than about 3% filler. In still other embodiments, a composition of the present disclosure will have greater than about 10% filler, greater than about 15% filler, greater than about 20% filler, greater than about 25% filler, greater than about 30% filler, greater than about 35% filler, or greater than about 40% filler.

Patch compositions will comprise a set retarder in some embodiments. A set retarder is a compound capable of delaying the set time of the composition. An example of a set retarder may be citric acid or borax, or a combination thereof. In certain embodiments, the set retarder is liquid while in other embodiments the set retarder is a powder. An appropriate set retarder will be well known to a person of ordinary skill in the art.

In an embodiment, the concentration of set retarder is between about 0.01% and about 3%, between about 0.01% and about 2% between about 0.05% and about 2.5%, between about 0.1% and about 2%, between about 0.5% and about 1.5%, between about 0.0001% and about 1.0%. In some embodiments, the set retarder is greater than about 0.001%, is greater than about 0.01% is greater than about 0.05%, is greater than about 0.1%, is greater than about 0.5%, is greater than about 1.0%, is greater than about 1.5%, or is greater than about 2.0%. In certain embodiments, the set retarder is less than about 3.0%, less than about 2.5%, less than about 2.0%, less than about 1.5%, less than about 1.0%, less than about 0.5%, less than about 0.3%, less than about 0.1%, less than about 0.01%, less than about 0.001%.

In some embodiments, the composition may further comprise a water reducer. Water reducers may be used when a higher final strength is desired at a specified density and fluidity. In some embodiments the water reducer will be powder while in other embodiments it will be a liquid water reducer. In an embodiment, the water reducer is CHRYSO 256 (high range) or 380 (midrange) or similar composition. A water reducer is a chemical (e.g., chemical composition) that allows a mixture to maintain the same fluidity with less water or more fluidity with the same amount of water.

In an embodiment, the concentration of the water reducer is between about 0.01% and about 3%, between about 0.01% and about 2%, between about 0.05% and about 2.5%, between about 0.1% and about 2%, between about 0.5% and about 1.5%, between about 0.0001% and about 1.0%. In some embodiments, the water reducer is greater than about 0.001%, is greater than about 0.01% is greater than about 0.05%, is greater than about 0.1%, is greater than about 0.5%, is greater than about 1.0%, is greater than about 1.5%, or is greater than about 2.0%. In certain embodiments, the water reducer is less than about 3.0%, less than about 2.5%, less than about 2.0%, less than about 1.5%, less than about 1.0%, less than about 0.5%, less than about 0.3%, less than about 0.1%, less than about 0.01%, less than about 0.001%.

Compositions of the present disclosure will have a range of possible set times based on the desired application. In some embodiments, the set time of the composition is determined by measuring penetration resistance with a pocket penetrometer (e.g., with a resistance of 4 psi as typically used in standard ASTM WK 27337) or cement setting time standard ASTM C403.

In an embodiment of the present disclosure, the set time for a composition can be between about 10 minutes and about 50 minutes, between about 15 minutes and about 40 minutes, between about 15 minutes and about 30 minutes, between about 20 minutes hours and about 40 minutes, between about 10 minutes and 30 minutes. In additional embodiments, a composition has a set time of less than 50 minutes, of less than about 40 minutes, of less than about 30 minutes, of less than about 20 minutes, of less than about 15 minutes. In other embodiments, a composition has a set time of greater than about 10 minutes, of greater than about 20 minutes, of greater than about 25 minutes, of greater than about 30 minutes, of greater than about 35 minutes, of greater than about 40 minutes.

Compositions of the present disclosure will have a range of compressive strengths at various times after the addition of a composition to a void depending on the desired properties of the composition.

In certain embodiments, the compressive strength is measured at 1 hour, 2 hours, 4 hours, 1 day, 3 days, 7 days and 28 days where the 28 day measurement is considered the final compressive strength. In other embodiments, the compressive strength is measured more often at smaller intervals or less often at larger intervals. In some embodiments, the compressive strength is measured at 90 days. In an embodiment, the compressive strength or bearing penetration or capacity resistance of a composition is measured at 1 hour, 2 hours, 4 hours, 7 days, and 28 days after backfilling using ASTM WK 27337 or C403.

In an embodiment, the compressive strength (e.g., ASTM C495 and/or C31) of a composition of the present disclosure at 1 hour will be between about 150 psi and about 450 psi, between about 200 psi and about 400 psi, between about 250 psi and about 350 psi. In additional embodiments, the compressive strength of the composition at 1 hour will be greater than about 150 psi, will be greater than about 200 psi, will be greater than about 250 psi, will be greater than about 300 psi, will be greater than about 350 psi. In an embodiment, the compressive strength of the composition of the present disclosure will be less than about 450 psi at 1 hour, less than about 400 psi at 1 hour, less than about 350 psi at 1 hour, less than about 300 psi at 1 hour, less than about 250 psi at 1 hour, less than about 250 psi at 1 hour.

In an embodiment, the compressive strength of a composition of the present disclosure at 4 hours will be between about 600 psi and about 1800 psi, 700 psi and about 1600 psi, between about 800 psi and about 1400 psi, between about 600 psi and about 1000 psi, between about 1200 psi and about 1800 psi. In additional embodiments, the compressive strength of the composition at 4 hours will be greater than about 600 psi, will be greater than about 800 psi, will be greater than about 1000 psi, will be greater than about 1200 psi, will be greater than about 1400 psi, will be greater than about 1600 psi. In an embodiment, the compressive strength of a composition of the present disclosure at 4 hours will be less than about 1800 psi, less than about 1600 psi, less than about 1400 psi, less than about 1200 psi, less than about 1000 psi, or less than about 800 psi, less than about 700 psi.

In an embodiment, the compressive strength of a composition of the present disclosure at 24 hours will be between about 2500 psi and about 6000 psi, between about 3000 psi and about 5000 psi, between about 3500 psi and about 4500 psi, between about 2500 psi and about 3500 psi, between about 4000 psi and about 6000 psi. In additional embodiments, the compressive strength of the composition at 24 hours will be greater than about 2500 psi, will be greater than about 3000 psi, will be greater than about 3500 psi, will be greater than about 4000 psi, will be greater than about 4500 psi, will be greater than about 5000 psi, or will be greater than about 5500 psi. In certain embodiments, the compressive strength of the composition at 24 hours will be less than about 6000 psi, less than about 5500 psi, less than about 5000 psi, less than about 4500 psi, less than about 4000 psi, less than about 3500 psi, or less than about 3000 psi.

In certain embodiments of the present disclosure, a suitable composition can be defined by the water to fly ash ratio, e.g., when using no filler, when using non-cementitious fly ash filler, or other suitable filler like sand. The water to fly ash ratio will be a water to cementitious fly ash plus additional non-cementitious fly ash filler ratio.

In certain embodiments, a composition can have a range of water to fly ash ratios depending on the water demand of the fly ash (or included filler), the desired flowability, the desired setting time and the desired final compressive strength. In certain embodiments, the water to fly ash ratio of a composition (W/FA) is between about 0.15 and about 0.25, between about 0.2 and about 0.6, between about 0.2 and about 0.5, between about 0.2 and about 0.4 or between about 0.25 and about 0.35. In additional embodiments, the water to fly ash ratio of a composition is greater than about 0.2, greater than about 0.25, greater than about 0.3, greater than about 0.35 or greater than about 0.4. In other embodiments, the water to fly ash ratio is less than about 0.6, less than about 0.5, less than about 0.4, less than about 0.35, less than about 0.3, less than about 0.25 or less than about 0.2.

In certain embodiments of the present disclosure, a patch composition does not include one or more of the following: does not include a water reducer, does not include Portland cement, does not include a set retarder, does not include any cementitious material other than cementitious fly ash, does not include a filler, does not include aggregate, does not include gravel, does not include $CaCO_3$ or lime other than that present in the cementitious fly ash and/or filler, or does not include sand. Furthermore, a composition of the present disclosure does not include native soils in some embodiments.

In certain embodiments, the flowability of a composition can be determined by a slump test C143 or a slump flow as determined by C1611 or spread as determined by D6103.

The density in a patch composition is important in certain embodiments. In embodiments, a composition of the present disclosure has a unit weight of between about 110 pcf and about 150 pcf, of between about 120 pcf and about 145 pcf, between about 125 pcf and about 135 pcf, between about 115 pcf and about 140 pcf, between about 115 pcf and about 135 pcf, between about 125 pcf and 150 pcf, between about 120 pcf and 150 pcf. In other embodiments, the unit weight of a composition is greater than about 90 pcf, greater than about 100 pcf, greater than about 110 pcf, greater than about 120 pcf, greater than about 130 pcf, greater than about 140 pcf, or greater than about 150 pcf. In still other embodiments, a composition has a unit weight of less than about 160 pcf, of less than about 150 pcf, of less than about 140 pcf, of less than about 130 pcf, of less than about 120 pcf, of less than about 110 pcf, of less than about 100 pcf or of less than about 90 pcf.

The present disclosure also contemplates a method of determining a trench patch composition comprising: identifying at least one fly ash for use in the composition; determining a water demand of each fly ash within the composition; calculating a water demand for the composition; determining a compressive strength for the composition; determining the amount of air content necessary for the composition to have a compressive strength of between 150 and 450 psi in 1 hour, a compressive strength of between 600 and 1800 psi in 4 hours, and a set time of less than 40 minutes; determining the time necessary to fill the void; and determining the concentration of set retarder necessary to delay the composition from setting in less time than necessary to fill the void.

The present disclosure also discloses a method of patching a trench with a patch composition comprising: determining the time necessary to fill the void; adding water and set retarder to a cementitious fly ash to make a wet mixture, wherein the composition has a compressive strength of between 150 and 450 psi in 1 hour, a compressive strength of between 600 and 1800 psi in 4 hours, and a set time of less than 40 minutes; and adding the composition to the trench. In additional embodiments, the method can further include adding a aggregate to the surface of the patch prior to setting. The aggregate will provide texture or abrasion, resulting in increased traction for vehicles or pedestrians. The aggregate may be sand, chips, crushed rock, or any material suitable for providing texture and traction. In addition, the surface of the patch may be squeegeed or broomed to provide texture either concurrent with the addition of aggregate or in place of aggregate.

In an embodiment of the present disclosure, the basic dry components for a composition can be packaged in bags or buckets, for easy mixing of small quantities by a contractor in the field with a wheelbarrow & shovel, an electric-drill & paddle-mixer for in-bucket mixing, or a small portable concrete mixer. Depending on the application, the combination of the dry ingredients in an embodiment can include cementitious fly ash only; cementitious fly ash and sand; cementitious fly ash and gravel; or cementitious fly ash, sand and gravel. In alternative embodiments, any combination of dry ingredients may be provided in a prepackaged bag or bucket. A prepackaged composition may also include powder set retarder, e.g., borax. In addition, a separate bag of surface aggregate can be included for spreading over the surface of the composition prior to setting.

In alternative embodiments, the patch composition can be modified to provide a permanent concrete pavement repair system.

Compositions for Use as Masonry Grout and Methods of Utilizing the Same

The present disclosure also discloses a masonry grout composition for filling cores or cavities in traditional masonry construction. While usually added for structural reasons, grout can also increase: fire ratings, security, acoustical performance, termite resistance, blast resistance, thermal storage capacity and anchorage capabilities. Masonry grout may be used to structurally bond wall elements into a wall system, e.g., steel reinforcing bars to the masonry. In addition, grouted cores can increase the net cross-sectional area of concrete masonry and permit walls to carry higher compressive, shear loads and lateral loads. A masonry grout composition of the present disclosure replaces traditional Portland-based cement grout by using cementitious fly ash.

In an embodiment, a masonry grout composition comprises between 0.0001% and 15% air by volume; between 70%-95% cementitious fly ash by weight; between 10%-30% water by weight, wherein the composition sets in less than 60 minutes and has a compressive strength of between 1500 psi and 3000 psi after 28 days.

The air content of the compositions of the present disclosure will vary depending on the desired properties of the composition. In some embodiments, the air content may be determined by the following formula using wet densities before and after the addition of air:

$$\text{Air content} = \frac{(\text{Unit Weight}_{no\ air} - \text{Unit Weight}_{air}) \times 100\%}{\text{Unit Weight}_{no\ air}}$$

In other embodiments, the air content can be determined using ASTM C231.

In certain embodiments, the air content is achieved by mixing an air entraining agent, i.e., a dry surfactant or liquid admixture into the cementitious fly ash and/or filler prior to addition of water. In these embodiments, the air content may by uniformly distributed by mixing directly in a truck or by mixing in a commonly used agitation/mixing device. The mixing process can occur prior to addition of water, after addition of water or simultaneously with the addition of water.

In another embodiment, the air content is achieved by addition of an air entraining agent after mixture of the dry ingredients (cementitious fly ash and filler) with water but prior to applying the composition to the void.

In specific embodiments, the air content may be achieved by adding a pre-formed cellular foam, e.g., GEOFOAM SNP foam liquid concentrate available from Cellular Concrete, LLC., 7020 Snowdrift Road, Suite 102, Allentown, Pa. 18106 or 5916 McIntyre St, Golden, Colo. 80403. The cellular foam may be pervious or non-pervious, and pre-foamed thereby reducing or alleviating the need to vigorously agitate the composition to activate the air entraining agent. Any suitable foaming agent may be used that achieves the desired end properties as described herein, e.g., an anionic foaming agent, a cationic foaming agent or a non-ionic foaming agent. An example of a pervious foam is GEOFOAM SP. An example of a non-pervious foam is GEOFOAM SNP. Suitable cellular foam is available from a variety of sources, e.g., Cellular Concrete, LLC; Provoton Foam Concrete, 28 East Larkspur Lane, Bristol, Ill. 60512; Allied Foam Tech Corp., 146 Keystone Dr. Montgomeryville, Pa. 18936: and Vermillion LLC and Associates, 2176 Sargent Daly Dr., Chattanooga, Tenn. 37421. The choice of an appropriate cellular foam is within one of skill in the art and may be dictated by cost, environmental concerns, or the need to meet the requirements of local or national agencies. In some embodiments, the foaming agent will conform to ASTM C869 and C796, in other embodiments the air entraining agent conforms to ASTM C260.

In some embodiments, the addition of cellular foam or similar air entraining agent may occur after the addition of water to the cementitious fly ash and filler immediately prior to the cementitious mixture leaving a mixing truck, as the cementitious mixture leaves the mixing truck (simultaneously) or after the cementitious mixture leaves the mixing truck.

The amount of air entraining agent necessary for a given composition will vary with the desired air content. In some embodiments, the final air content of the composition will be between about 0.001% and about 15%, between about 0.01% and about 13%, between about 0.1% and about 10%, between about 1.0% and about 8%, between about 2% and about 6%, between about 0.1% and about 5%, between about 0.1% and about 2%, between about 4% and about 10%, between about 4% and about 8%. In some embodiments, the composition does not contain any additional air content, i.e., the composition is not purposefully air entrained.

In some embodiments, the final air content will be greater than 0.1%, greater than 1%, greater than 2%, greater than 4%, greater than 6%, greater than 8%, greater than 10%, greater than 12%.

In other embodiments, the final air content of the composition will be less than 15%, less than 13%, less than 10%, less than 8%, less than 6%, less than 4%, less than 2%, less than 1%, less than 0.1%, less than 0.01%.

In an embodiment of the presently disclosure masonry grout composition, the cementitious fly ash is Class C fly ash as defined by ASTM C618 or the standards of a local agency. In other embodiments of the present disclosure, the cementitious fly ash can have cementitious properties without qualifying as Class C fly ash under ASTM C618 or an equivalent standard. A cementitious fly ash of the present disclosure is a fly ash that sets (e.g., solidifies to 4 psi) within about thirty minutes at a water content of 30% by weight when water and cementitious fly ash are the only ingredients.

In an embodiment of the present disclosure, a masonry grout composition has between about 70% and about 95% cementitious fly ash, between about 75% and about 90% cementitious fly ash, between about 80% and about 85% cementitious fly ash, between about 70% cementitious fly ash and about 85% cementitious fly ash, between about 80% and about 95% cementitious fly ash.

In some embodiments of the present disclosure, a composition has less than about 95% cementitious fly ash, less than about 90% cementitious fly ash, less than about 85% cementitious fly ash, less than about 80% cementitious fly ash, less than about 75% cementitious fly ash, less than about 70% cementitious fly ash. In additional embodiments of the present disclosure, a masonry grout composition has greater than about 70% cementitious fly ash, greater than about 75% cementitious fly ash, greater than about 80% cementitious fly ash, greater than about 85% cementitious fly ash, greater than about 90% cementitious fly ash.

In an embodiment of the presently disclosed composition, the water is standard city potable water. In another embodiment, the water used in the composition is substantially purified of additional minerals or other impurities. In still another embodiment of the present disclosure, the water is non-potable water. In additional embodiments, the water is selected based on its natural impurities, i.e., specific mineral content like calcium, magnesium, iron, or similar water minerals.

The water content of the presently disclosed composition may vary depending on desired flowability, setting time and final compressive strength. In an embodiment of the present disclosure, a composition has a the water content of between about 10% and about 30%, between about 15% and about 25%, between about 10% and about 20%, between about 15% and about 30%. In additional embodiments, a composition has greater than about 10% water, greater than about 15% water, greater than about 20% water, greater than about 25% water, or greater than about 30% water. In other embodiments, a composition has less than about 30% water, less than about 25% water, less than about 20% water, less than about 15% water, less than about 10% water. Any water included with additional ingredients, e.g., aqueous water retarders, foaming agents, etc. under the circumstances encountered in the field by the inventors has been negligible in comparison to the primary batch water and therefore has not been included in the above calculations. Depending on the actual water content of the additional ingredients used it may be necessary to consider the additional water in the final water concentrations.

In some embodiments of the present disclosure, a composition will include at least one filler. In additional embodiments, a composition will include only one filler, while in other embodiments, a composition will contain only two fillers. In still additional embodiments, a composition will contain less than 3 fillers or less than 4 fillers. A filler in the present disclosure can be additional fly ash, e.g., type F fly ash as determined by ASTM C618 or equivalent standard. A filler can also be non-specification grade non-cementitious fly ash, e.g., a fly ash that does not meet the specifications determined by ASTM C618. In certain embodiments a filler can be sand, bottom ash, quarry fines, soil, gravel and Portland cement, rubber, aggregate, or recycled version thereof. Determination of the filler material can be based on economics, availability, city, county and/or state specifications, or on the desired properties of the composition, e.g., desired setting time, flowability, or final compressive strength.

In an embodiment, a composition of the present disclosure will have between about 20% and about 60% filler, between about 25% and about 55% filler, between about 30% and about 50% filler, between about 20% and about 40% filler, between about 20% and about 30%, between about 40% and about 60%, between about 30% and about 40% filler. In certain embodiments, a composition of the present disclosure will have less than about 60% filler, less than about 55% filler, less than about 50% filler, less than about 45% filler, less than about 40% filler, less than about 35% filler, less than about 30% filler, less than about 25% filler. In still other embodiments, a composition of the present disclosure will have greater than about 20% filler, greater than about 25% filler, greater than about 30% filler, greater than about 35% filler, greater than about 40% filler, greater than about 50% filler, or greater than about 55% filler.

Masonry grout compositions will comprise a set retarder in some embodiments. A set retarder is a compound capable of delaying the set time of the composition. In certain embodiments, delaying the set time is necessary to allow a masonry grout composition to completely fill a void before setting. An example of a set retarder may be citric acid or borax, or a combination thereof. In certain embodiments, the set retarder is liquid while in other embodiments the set retarder is a powder. An appropriate set retarder will be well known to a person of ordinary skill in the art.

In an embodiment, the concentration of set retarder is between about 0.01% and about 3%, between about 0.01% and about 2% between about 0.05% and about 2.5%, between about 0.1% and about 2%, between about 0.5% and about 1.5%, between about 0.0001% and about 1.0%. In some embodiments, the set retarder is greater than about 0.001%, is greater than about 0.01% is greater than about 0.05%, is greater than about 0.1%, is greater than about 0.5%, is greater than about 1.0%, is greater than about 1.5%, or is greater than about 2.0%. In certain embodiments, the set retarder is less than about 3.0%, less than about 2.5%, less than about 2.0%, less than about 1.5%, less than about 1.0%, less than about 0.5%, less than about 0.3%, less than about 0.1%, less than about 0.01%, less than about 0.001%.

Compositions of the present disclosure will have a range of possible set times based on the desired application. In some embodiments, the set time of the masonry grout composition is determined by measuring penetration resistance with a pocket penetrometer (e.g., with a resistance of 4 psi as typically used in standard ASTM WK 27337) or cement setting time standard ASTM C403. In an embodiment of the present disclosure, the set time for a composition can be between about 10 minutes and about 60 minutes, between about 15 minutes and about 50 minutes, between about 15 minutes and about 30 minutes, between about 20 minutes hours and about 40 minutes, between about 10 minutes and 30 minutes, between about 30 minutes and 60 minutes. In additional embodiments, a composition has a set time of less than about 60 minutes, of less than about 50 minutes, of less than about 40 minutes, of less than about 30 minutes, of less than about 20 minutes, of less than about 1 hour. In other embodiments, a composition has a set time of greater than about 10 minutes, of greater than about 20 minutes, of greater than about 25 minutes, of greater than about 30 minutes, of greater than about 35 minutes, of greater than about 40 minutes, of greater than about 50 minutes, of greater than about 60 minutes.

Masonry grout compositions of the present disclosure will have a range of compressive strengths at various times after the addition of a composition to a void depending on the desired properties of the composition.

In certain embodiments, the compressive strength is measured at 1 hour, 2 hours, 4 hours, 1 day, 3 days, 7 days and 28 days where the 28 day measurement is considered the final compressive strength. In other embodiments, the compressive strength is measured more often at smaller intervals or less often at larger intervals. In some embodiments, the compressive strength is measured at 90 days. In an embodiment, the compressive strength or bearing penetration or capacity resistance of a composition is measured at 1 hour, 2 hours, 4 hours, 7 days, and 28 days after backfilling using ASTM WK 27337 or C403. In additional embodiments, the flexural strength is measured using ASTM C78.

In an embodiment, the compressive strength of a composition of the present disclosure at 1 hour will be between about 150 psi and about 450 psi, between about 200 psi and about 400 psi, between about 250 psi and about 350 psi. In additional embodiments, the compressive strength of the composition at 1 hour will be greater than about 150 psi, will be greater than about 200 psi, will be greater than about 250 psi, will be greater than about 300 psi, will be greater than about 350 psi. In an embodiment, the compressive strength of the composition of the present disclosure will be less than about 450 psi at 1 hour, less than about 400 psi at 1 hour, less than about 350 psi at 1 hour, less than about 300 psi at 1 hour, less than about 250 psi at 1 hour, less than about 250 psi at 1 hour.

In an embodiment, the compressive strength of a composition of the present disclosure at 1 day will be between about 500 psi and about 1800 psi, 700 psi and about 1600 psi, between about 800 psi and about 1400 psi, between about 600 psi and about 1000 psi, between about 1200 psi and about 1800 psi. In additional embodiments, the compressive strength of the composition at 1 day will be greater than about 500 psi, will be greater than about 700 psi, will be greater than about 1000 psi, will be greater than about 1200 psi, will be greater than about 1400 psi, will be greater than about 1600 psi. In an embodiment, the compressive strength of a composition of the present disclosure at 1 day will be less than about 1800 psi, less than about 1600 psi, less than about 1400 psi, less than about 1200 psi, less than about 1000 psi, or less than about 800 psi, less than about 700 psi.

In an embodiment, the compressive strength of a composition of the present disclosure at 7 days will be between about 1000 psi and about 2000 psi, 1100 psi and about 1800 psi, between about 1200 psi and about 1600 psi, between about 100 psi and about 1500 psi, between about 1500 psi and about 2000 psi. In additional embodiments, the compressive strength of the composition at 7 days will be greater than about 500 psi, will be greater than about 700 psi, will be greater than about 1000 psi, will be greater than about 1200 psi, will be greater than about 1400 psi, will be greater than about 1600 psi, will be greater than 1800 psi. In an embodiment, the compressive strength of a composition of the present disclosure at 7 days will be less than about 2000 psi, less than about 1800 psi, less than about 1600 psi, less than about 1400 psi, less than about 1200 psi, less than about 1000 psi, or less than about 800 psi, less than about 700 psi.

In an embodiment, the compressive strength of a composition of the present disclosure at 28 day will be between about 1500 psi and about 3000 psi, between about 3000 psi and about 5000 psi, between about 3500 psi and about 4500 psi, between about 2500 psi and about 3500 psi, between about 4000 psi and about 6000 psi. In additional embodiments, the compressive strength of the composition at 28 days will be greater than about 2500 psi, will be greater than about 3000 psi, will be greater than about 3500 psi, will be greater than about 4000 psi, will be greater than about 4500 psi, will be greater than about 5000 psi, or will be greater than about 5500 psi. In certain embodiments, the compressive strength of the composition at 28 days will be less than about 6000 psi, less than about 5500 psi, less than about 5000 psi, less than about 4500 psi, less than about 4000 psi, less than about 3500 psi, or less than about 3000 psi.

In certain embodiments of the present disclosure, a suitable masonry grout composition can be defined by the water to fly ash ratio, e.g., when using no filler, when using non-cementitious fly ash filler, or other suitable filler like ground rubber. In certain embodiments, the water to fly ash ratio will be a water to cementitious fly ash plus additional non-cementitious fly ash filler ratio.

In certain embodiments, a composition can have a range of water to fly ash ratios depending on the water demand of the fly ash (or included filler), the desired flowability, the desired setting time and the desired final compressive strength. In certain embodiments, the water to fly ash ratio of a composition (W/FA) is between about 0.10 and about 0.30, between about 0.15 and about 0.25, between about 0.2 and about 0.25, between about 0.2 and about 0.3, between about 0.1 and about 0.2 or between about 0.05 and about 0.2. In additional embodiments, the water to fly ash ratio of a composition is greater than about 0.1, greater than about 0.15, greater than about 0.2, greater than about 0.25. In other embodiments, the water to fly ash ratio is less than about 0.35, less than about 0.3, less than about 0.25, less than about 0.2, less than about 0.15, less than about 0.1.

In certain embodiments of the present disclosure, a masonry grout composition does not include one or more of the following: does not include a water reducer, does not include Portland cement, does not include a set retarder, does not include any cementitious material other than cementitious fly ash, does not include a filler, does not include aggregate, does not include gravel, does not include $CaCO_3$ or lime other than that present in the cementitious fly ash and/or filler, or does not include sand. Furthermore, a composition of the present disclosure does not include native soils in some embodiments.

In certain embodiments, the flowability of a composition can be determined by a slump test C143 or a slump flow as determined by C1611 or spread as determined by D6103. In some embodiments, the masonry grout composition meets or exceeds the performance requirements of ASTM C476.

The density of the masonry grout composition is important in certain embodiments. In embodiments, a composition of the present disclosure has a unit weight of between about 110 pcf and about 150 pcf, of between about 120 pcf and about 145 pcf, between about 125 pcf and about 135 pcf, between about 115 pcf and about 140 pcf, between about 115 pcf and about 135 pcf, between about 125 pcf and 150 pcf, between about 120 pcf and 150 pcf. In other embodiments, the unit weight of a composition is greater than about 90 pcf, greater than about 100 pcf, greater than about 110 pcf, greater than about 120 pcf, greater than about 130 pcf, greater than about 140 pcf, or greater than about 150 pcf. In still other embodiments, a composition has a unit weight of less than about 160 pcf, of less than about 150 pcf, of less than about 140 pcf, of less than about 130 pcf, of less than about 120 pcf, of less than about 110 pcf, of less than about 100 pcf or of less than about 90 pcf.

The present disclosure also contemplates a method of determining a masonry grout for construction comprising: identifying at least one fly ash for use in the composition; determining a water demand of each fly ash within the composition; calculating a water demand for the composition; determining a compressive strength for the composition; determining the amount of air content necessary for the composition to set is less than 60 minutes and has a compressive strength of between 100 and 500 psi after 1 hour and 2500 and 6000 psi after 24 hours.

The determination of suitable fly ash, water demand, compressive strength, air content, density, time to finish the construction project, and the concentration of set retarder can be accomplished as discussed elsewhere in this application.

The present disclosure also contemplates a method of filling a void between retaining walls with masonry grout composition comprising: mixing cementitious fly ash and filler to a predetermined ratio; and adding water to the mix of cementitious fly ash and filler to make a wet mixture, wherein the composition sets is less than 60 minutes and has a compressive strength of between 100 and 500 psi after 1 hour and 2500 and 6000 psi after 24 hours.

Although embodiments of the present disclosure have been described with respect to backfilling a trench to prevent ice lens formation and quicker return to use of the backfilled area, it should be appreciated that the principles of the present disclosure can also be applied to filling voids due to pipe abandonment, annular spaces, undercut areas, and other void filling applications. It should also be appreciated that the principles of the present disclosure can also be applied to providing structural support for utilities, replacement of unstable subgrade during pavement repairs and similar applications.

The foregoing description of the exemplary embodiments of the disclosure has been presented for the purposes of illustration and description. They are not intended to be exhaustive or to limit the disclosure to the precise forms disclosed. Many modifications and variations are possible in light of the above teaching. It is intended that the scope of the disclosure be limited not with this detailed description, but rather by the claims appended hereto.

EXAMPLES

The weight of the ingredients in the following examples have been normalized to provide one cubic yard of final composition. That is, the actual amounts used in the examples have been proportionally increased or decreased based on the final volume achieved to one cubic yard. For example, if a laboratory batch of 25 lbs cementitious fly ash and 8 lbs of water yielded a final volume of 0.01 cubic yard, the example would be reported below as 2,500 lbs fly ash and 800 lbs water.

Example 1

A 1.5:1 (non-cementitious/cementitious) mix composition of the following components was prepared using a mixing truck: 685 lbs of cementitious fly ash ASTM C618 class C from Excel Energy Pawnee Station; 1031 lbs of non-cementitious fly ash from Excel Energy Cherokee Station; 652 lbs of city water; and 4.7 cubic feet of cellular foam from GEO-FOAM SNP (synthetic non-permeable foam), C796 and C869.

The composition had the following physical properties: Time to set was approximately 15 minutes; the spread (ASTM D6103) was 9.5 inches; the slump-cone spread was approximately 26 inches; the air content was 18%; the unit weight was 88 pcf; and the water/fly ash ratio was 0.38.

The composition has the following compressive strengths: 30 psi at four hours; 40 psi at one day; 166 psi at seven days; and 274 psi at 28 days. The composition had a removability modulus of 1.42.

Example 2

A 1.5:1 (non-cementitious/cementitious) mix composition of the following components was prepared using a mixing truck: 644 lbs of cementitious fly ash ASTM C618 class C from Excel Energy Pawnee Station; 970 lbs of non-cementitious fly ash from Excel Energy Cherokee Station; 613 lbs of city water; and 6.1 cubic feet of cellular foam from GEO-FOAM SNP (synthetic non-permeable foam), C796 and C869.

The composition had the following physical properties: Time to set was approximately 15 minutes; the spread (ASTM D6103) was 14 inches; the slump-cone spread was approximately 35 inches; the air content was 23%; the unit weight was 83 pcf; and the water/fly ash ratio was 0.38.

The composition has the following compressive strengths: 19 psi at four hours; 32 psi at one day; 91 psi at seven days; and 151 psi at 28 days. The composition had a removability modulus of 0.96.

Example 3

A 2:1 (non-cementitious/cementitious) mix composition of the following components was prepared in a laboratory: 572 lbs of cementitious fly ash ASTM C618 class C from Excel Energy Pawnee Station; 1145 lbs of non-cementitious fly ash from Excel Energy Cherokee Station; 687 lbs of city water; and 4 cubic feet of cellular foam from GEOFOAM SNP (synthetic non-permeable foam), C796 and C869.

The composition had the following physical properties: The spread (ASTM D6103) was 10 inches; the slump-cone spread was approximately 26 inches; the air content was 15%; the unit weight was 86 pcf; and the water/fly ash ratio was 0.40.

The composition has the following compressive strengths: 22 psi at seven days; and 142 psi at 28 days. The composition had a removability modulus of 0.99.

Example 4

A 3:1 (non-cementitious/cementitious) mix composition of the following components was prepared in the laboratory: 390 lbs of cementitious fly ash ASTM C618 class C from Excel Energy Pawnee Station; 1171 lbs of non-cementitious fly ash from Excel Energy Cherokee Station; 734 lbs of city water, and 4.1 cubic feet of cellular foam from GEOFOAM SNP (synthetic non-permeable foam), C796 and C869.

The composition had the following physical properties: The spread (ASTM D6103) was 10 inches; the slump-cone spread was approximately 26 inches; the air content was 15%; the unit weight was 85 pcf; and the water/fly ash ratio was 0.47.

The composition has the following compressive strengths: 55 psi at seven days; and 123 psi at 28 days. The composition had a removability modulus of 0.90.

Example 5

A composition of the following components was prepared in the laboratory: 732 lbs of cementitious fly ash ASTM C 618 class C from Excel Energy Pawnee Station; 932 lbs of non-cementitious fly ash from Excel Energy Cherokee Station; 699 lbs of city water; and 4.9 cubic feet of cellular foam from GEOFOAM SNP (synthetic non-permeable foam), C796 and C869.

The composition had the following physical properties: The spread (ASTM D6103) was 11 inches; the slump-cone spread was approximately 28 inches; the air content was 18.2%; the unit weight was 87.5 pcf; and the water/fly ash ratio was 0.42.

The composition has the following compressive strengths: 5 psi at four hours; 38 psi at one day; 126 psi at seven days; and 157 psi at 28 days. The composition had a removability modulus of 1.06.

Example 6

In example 6, the following compositions were prepared for comparison as displayed in Table 2 and 3.

TABLE 2

The comparison of 9 different compositions with values in pounds per cubic yard unless otherwise indicated, e.g., air.

| Mix. No. | | Cementitious fly ash | Non-cementitious fly ash | Additional Filler (e.g., Sand) | Water | Total | % Air |
|---|---|---|---|---|---|---|---|
| 1 | Truck | 685 | 1031 | | 652 | 2368 | 18 |
| 2 | Truck | 644 | 970 | | 613 | 2227 | 23 |
| 3 | Lab | 572 | 1145 | | 687 | 2404 | 15 |
| 4 | Lab | 390 | 1171 | | 734 | 2295 | 15 |
| 5 | Lab | 732 | 932 | | 699 | 2363 | 18 |
| 6 | Lab | 1350 | | | 405 | 1755 | 46 |
| 7 | Lab | 831 | | | 249 | 1080 | 67 |
| 8 | Lab | 1170 | | | 585 | 1755 | 40 |
| 9 | Lab | 720 | | | 360 | 1080 | 63 |

TABLE 3

Is an extension of Table 2 with the same compositions as Table 2 but with values in percent by weight and including the 28 day compressive strenth data and RE for each composition.

| Mix. No. | | Cementitious fly ash | Non-cementitious fly ash | Additional Filler (e.g., Sand) | Water | % Air | 28 day Compressive Strength (PSI) | RE |
|---|---|---|---|---|---|---|---|---|
| 1 | Truck | 29% | 44% | 0% | 28% | 18 | 275 | 1.42 |
| 2 | Truck | 29% | 44% | 0% | 28% | 23 | 151 | 0.96 |
| 3 | Lab | 24% | 48% | 0% | 29% | 15 | 142 | 0.99 |
| 4 | Lab | 17% | 51% | 0% | 32% | 15 | 123 | 0.90 |
| 5 | Lab | 31% | 39% | 0% | 30% | 18 | 157 | 1.06 |
| 6 | Lab | 77% | 0% | 0% | 23% | 46 | 552 | 1.29 |
| 7 | Lab | 77% | 0% | 0% | 23% | 67 | 120 | 0.29 |
| 8 | Lab | 67% | 0% | 0% | 33% | 40 | 355 | 1.00 |
| 9 | Lab | 67% | 0% | 0% | 33% | 63 | 81 | 0.25 |

Mix numbers 1 through 5 of Example 6 (e.g., Table 1 and Table 2) are compositions comprising cementitious fly ash, non-cementitious fly ash, water and cellular foam to provide air content. Mix numbers 6 through 9 are compositions containing no filler, no non-cementitious fly ash or otherwise, with water and cellular foam.

Example 7

Compressive strength testing for two types of cellular annular grouts were performed, one with Portland cement, the others with Class C fly ash (no Portland cement), with and without water reducers. Sufficient cellular foam was added to achieve the project specified density of 55 pcf, +/5 pcf; the minimum strength was specified as 300 psi at 28 days. Borax was added for sufficient set-retardation in mix numbers 2, 4 and 5. The test results are summarized in table 4 below. Mix number 1 of Table 4 is traditional Portland cement.

TABLE 4

Comparison of densities and compressive strength for five different annular grout compositions.

| Mix No. | Material description | Density (pcf) | 7-day (psi) | 28-day (psi) |
|---|---|---|---|---|
| 1 | Traditional Portland Cement | 53.3 | 550 | 544 |
| 2 | Class C fly ash, with a water retarder and Borax as a set retarder | 55.0 | 560 | 586 |
| 3 | 50% Portland (dry ingredient weight, 50% Type F fly ash (dry ingredient weight) | — | 290 | — |
| 4 | Class C fly ash with borax as a set retarder | 52.2 | 252 | 489 |
| 5 | Class C fly ash with borax as a set retarder | 47.0 | 238 | 305 |

Example 8

The compressive strength of different compositions of the present disclosure were tested at 1 day, 3 days, 7 days, and 28 days. As shown in Table 5, cementitious fly ash compositions of the present disclosure perform similarly to traditional Portland cement at lower water to cementitious material, i.e., fly ash, ratios.

TABLE 5

Cementitious fly ashes can perform similar to traditional Portland cement at lower water to cementitious material ratios.

| Mix No. | Water to Fly Ash Ratio | 1 Day (psi) | 3 Day (psi) | 7-day (psi) | 28-day (psi) |
|---|---|---|---|---|---|
| 1 | Pawnee Cementitious Fly Ash 0.21 W/FA | 2540 | 3890 | 4620 | 5710 |
| 2 | Pawnee Cementitious Fly Ash 0.23 W/FA | 2490 | 4270 | 4870 | 6190 |
| 3 | Pawnee Cementitious Fly Ash 0.45 W/FA | 900 | 1060 | 1330 | 2015 |
| 4 | Pawnee Cementitious Fly Ash 0.50 W/FA | 300 | 800 | 990 | 1480 |
| 5 | Holcim Cementitious Fly Ash 0.45 W/FA | 1380 | 4560 | 6430 | 5440 |
| 6 | Holcim Cententitious Fly Ash 0.50 W/FA | 1050 | 3710 | 5440 | 8040 |

Example 9

The effect of a set retarder, i.e., borax, was tested on compositions of the present disclosure. As shown in Table 6, the effect of borax, by percent, are displayed with time of set in minutes and time to achieve 63 psi in minutes for a 0.25 W/FA composition for use in pavement patching. The borax dosage is expressed as a percentage of the fly ash weight. The 63 psi (4.5 tons/square-foot) gives an indication of when cars and light trucks could drive over the patch, without damage to the surface or breaking the slab in flexure. The compressive strength required for heavy trucks will vary based on municipalities and state regulations. For example, one municipality requires 1800 psi and the Colorado Department of Transportation requires 2500 psi for traditional concrete prior to opening to traffic.

TABLE 6

The effectiveness of a set retarder on different compositions for use as a pavement patch

| Mix No. | % Borax | Set Time (min) | Time to 63 psi (min) | Ratio of 63 psi/ Set Time |
|---|---|---|---|---|
| 1 | 0.0 | 4-5 | 7 | 1.6 |
| 2 | 0.1 | 7 | 10 | 1.4 |
| 3 | 0.2 | 12 | — | — |
| 4 | 0.25 | 19 | 32 | 1.7 |
| 5 | 0.3 | 30 | 42 | 1.4 |
| 6 | 0.4 | 70 | 127 | 1.8 |

Example 10

The amount of chemical shrinkage was tested by comparing two different water to cement ratios for traditional Portland cement (Mix. Nos. 1 and 2) with two different water to fly ash ratios of the present disclosure (Mix Nos. 3 and 4). Chemical shrinkage is the volumetric change in a composition that occurs at the time of composition set, i.e., transitioning from fluid to solid. Volume is measured when the composition remains flowable and again immediately after setting. The change in volume reflects the % chemical shrinkage. As shown in Table 7, traditional Portland cement compositions undergo a substantial chemical shrinkage, e.g., Mix Nos. 1 and 2 of Table 7. By comparison, compositions of the present disclosure have dramatically reduced chemical shrinkage, e.g., Mix Nos. 3 and 4. Also shown in Table 7 is the effect even a small change in water to cement ratio has on the % chemical shrinkage. For example, in Mix No. 1 of Table 7, a 0.45 water to cement ratio has a % chemical shrinkage of 1.22. A change to 0.50 water to cement mixture results in a % chemical shrinkage of 2.02, see, e.g., Mix No. 2 of Table 7. By contrast, a change from 0.22 water to fly ash ratio to 0.50 water to fly ash ratio only results in a change of 0.02% chemical shrinkage, compare Mix Nos. 3 and 4 of Table 7.

TABLE 7

Chemical shrinkage of traditional Portland cement compared with compositions of the present disclosure.

| Mix No. | Composition | % Chemical Shrinkage |
|---|---|---|
| 1 | Traditional Portland Cement Water to Cement Ratio = 0.45 | 1.22% |
| 2 | Traditional Portland Cement Water to Cement Ration = 0.50 | 2.02 % |
| 3 | Composition of the Present Disclosure Water to Fly Ash Ratio (no filler) = 0.22 | 0.03% |
| 4 | Composition of the Present Disclosure Water to Fly Ash Ratio (no filler) = 0.50 | 0.0.5% |

Example 11

The amount of drying shrinkage was tested by comparing Portland cement (Mix. Nos. 1) with two different water to fly ash ratios of the present disclosure (Mix Nos. 2 and 3). Drying shrinkage is the volumetric change in a composition that occurs from the time of setting to 28 days. Volume is measured when after the composition sets and again at 28 days. The change in volume reflects the % drying shrinkage as shown in Table 8.

TABLE 8

Drying shrinkage of traditional Portland cement compared with compositions of the present disclosure.

| Mix No. | Composition | % Drying Shrinkage |
|---|---|---|
| 1 | Traditional Portland-cement concrete | 0.04% to 0.06% |
| 2 | Ratio of Cementitious Fly Ash and Water = 0.21 | 0.002% |
| 3 | Ratio of Cementitious Fly Ash and Water (Aggregate added to 50% by volume) = 0.23 | 0.001% |

What is claimed is:

1. A low density annular grout composition for filling voids consisting essentially of:
   between 30% and 85% air by volume;
   between 50% and 90% class C fly ash by weight;
   between 20% and 40% water by weight; and
   between 0.01% and 2% set retarder by weight,
   wherein the composition has compressive strength of between 100 and 600 psi at seven days, a compressive strength of less than 1500 psi at 28 days, and a density of between 20 and 75 pcf.

2. The composition of claim 1, wherein the air is between 40% and 65% by volume of the composition.

3. The composition of claim 1, wherein the class C fly ash is between 70% and 80% by weight of the composition.

4. The composition of claim 1, wherein the water is between 20% and 30% by weight of the composition.

5. The composition of claim 1, wherein the set retarder is between 0.01% and 1.0% by weight of the composition.

6. The composition of claim 1, wherein
the air is between 40% and 65% by volume;
the class C fly ash is between 60% and 80% by weight;
the water is between 20% and 35% by weight; and
the set retarder is between 0.01% and 1.0% by weight.

7. The composition of claim 1 or 6, wherein the water to class C fly ash ratio in the composition is between 0.15 to 0.40.

8. The composition of claim 1, or 6, wherein the volume of air results from an air entraining agent.

9. The composition of claim 8, wherein the air entraining agent is a cellular foam.

10. A low density annular grout composition for filling voids consisting essentially of:
between 30% and 85% air by volume;
between 30% and 90% class C fly ash by weight;
between 0.1% and 50% class F fly ash by weight;
between 20% and 40% water by weight; and
between 0.01% and 2% set retarder by weight,
wherein the composition has compressive strength of between 100 and 600 psi at seven days, a compressive strength of less than 1500 psi at 28 days, and a density of between 20 and 75 pcf.

11. The composition of claim 10, wherein the air is between 40% and 65% by volume of the composition.

12. The composition of claim 10, wherein the class C fly ash is between 70% and 80% by weight of the composition.

13. The composition of claim 10, wherein the water is between 20% and 30% by weight of the composition.

14. The composition of claim 10, wherein the set retarder is between 0.01% and 1.0% by weight of the composition.

15. The composition of claim 10, wherein the class F fly ash is between 10% and 40% by weight of the composition.

16. The composition of claim 10, wherein the air is between 40% and 65% by volume;
the class C fly ash is between 60% and 80% by weight;
the class F fly ash is between 10% and 40% by weight;
the water is between 20% and 35% by weight; and
the set retarder is between 0.01% and 1.0% by weight.

17. The composition of claim 10 or 16, wherein the water to class C fly ash ratio in the composition is between 0.15 to 0.40.

18. The composition of claim 10 or 16, wherein the volume of air results from an air entraining agent.

19. The composition of claim 18, wherein the air entraining agent is a cellular foam.

* * * * *